(12) United States Patent
Nakache et al.

(10) Patent No.: US 8,283,355 B2
(45) Date of Patent: Oct. 9, 2012

(54) PYRIMIDINE DERIVATIVES AS POSH AND POSH-AP INHIBITORS

(75) Inventors: Philippe Nakache, Ness Ziona (IL); Itzchak Angel, Ness Ziona (IL); Nurit Livnah, Mazkeret Batya (IL); Maxim Borovitov, St. Petersburg (RU)

(73) Assignee: Proteologics, Ltd., Rehovot (IL)

( * ) Notice: Subject to any disclaimer, the term of this patent is extended or adjusted under 35 U.S.C. 154(b) by 548 days.

(21) Appl. No.: 12/312,416

(22) PCT Filed: Nov. 7, 2007

(86) PCT No.: PCT/IL2007/001356
§ 371 (c)(1),
(2), (4) Date: Aug. 13, 2009

(87) PCT Pub. No.: WO2008/056356
PCT Pub. Date: May 15, 2008

(65) Prior Publication Data
US 2010/0179178 A1    Jul. 15, 2010

Related U.S. Application Data

(60) Provisional application No. 60/857,378, filed on Nov. 7, 2006, provisional application No. 60/959,831, filed on Jul. 17, 2007.

(51) Int. Cl.
*A61K 31/505* (2006.01)
*C07D 239/02* (2006.01)

(52) U.S. Cl. ........................ 514/275; 544/297

(58) Field of Classification Search ............. 514/275; 544/297
See application file for complete search history.

(56) References Cited

U.S. PATENT DOCUMENTS

| 6,767,909 | B2 | 7/2004 | Joutsamo et al. |
| 2005/0214751 | A1 | 9/2005 | Reiss et al. |
| 2006/0014807 | A1* | 1/2006 | Lin ............... 514/357 |
| 2006/0111278 | A1 | 5/2006 | Thim et al. |

FOREIGN PATENT DOCUMENTS

| EP | 1422228 | 5/2004 |
| WO | WO 96/04242 | 2/1996 |
| WO | WO 2004/031158 | 4/2004 |

OTHER PUBLICATIONS

El-Shaaer et al., "Synthesis of Some New Heterobicyclic Compounds Bearing Chromon-3-yl Moiety and Related Compounds as Antimicrobial Agents", *Mans. Sci. Bull. (A. Chem.)*, 24(1)(1):171-185 (1997).
Li J. et al., "Strategy for Discovering Chemical Inhibitors of Human Cyclophilin A: Focused Library Design, Virtual Screening, Chemical Synthesis and Bioassay", *J. of Comb. Chem.*, 8(3):326-337 (2006).
International Search Report for PCT/IL07/01356 dated Feb. 2, 2009.

* cited by examiner

*Primary Examiner* — James O Wilson
*Assistant Examiner* — Ebenezer O Sackey
(74) *Attorney, Agent, or Firm* — Ropes & Gray LLP

(57) ABSTRACT

Pyrimidine deriviatives are ubiquination inhibitors that inhibit the ubiquitin ligase activity, particularly of POSH polypeptides, are useful for the treatment of viral infections and neurological disorders.

16 Claims, 4 Drawing Sheets

US 8,283,355 B2

PYRIMIDINE DERIVATIVES AS POSH AND POSH-AP INHIBITORS

CROSS-REFERENCE TO RELATED APPLICATIONS:

This application is a national stage filing under 35 U.S.C. 371 of International Application PCT/IL2007/001356 filed Nov. 7, 2007, which claims the benefit of U.S. Provisional Application No. 60/959,831 filed Jul. 17, 2007 and U.S. Provisional Patent Application Ser. No. 60/857,378 filed Nov. 7, 2006. The teachings of all of the referenced applications are incorporated by reference in their entirety. International Application PCT/IL2007/001356 was published under PCT Article 21 (2) in English.

FIELD OF THE INVENTION

The present invention relates to small pyrimidine derivatives, which are inhibitors of the ubiquitin ligase activity of a human polypeptide, particularly to POSH inhibitors, and to compositions and methods for treatment of viral infections and neurological conditions, disorders or diseases.

SEQUENCE LISTING

The instant application contains a Sequence Listing which has been submitted via EFS-Web and is hereby incorporated by reference in its entirety. Said ASCII copy, created on Mar. 15, 2010, is named PROL4931.txt, and is 57,273 bytes in size.

BACKGROUND OF THE INVENTION

Potential drug target validation involves determining whether a DNA, RNA or protein molecule is implicated in a disease process and is therefore a suitable target for development of new therapeutic drugs. Drug discovery, the process by which bioactive compounds are identified and characterized, is a critical step in the development of new treatments for human diseases. The landscape of drug discovery has changed dramatically due to the genomics revolution. DNA and protein sequences are yielding a host of new drug targets and an enormous amount of associated information.

The identification of genes and proteins involved in various disease states or key biological processes, such as inflammation and immune response, is a vital part of the drug design process. Many diseases and disorders could be treated or prevented by decreasing the expression of one or more genes involved in the molecular etiology of the condition if the appropriate molecular target could be identified and appropriate antagonists developed. For example, cancer, in which one or more cellular oncogenes become activated and result in the unchecked progression of cell cycle processes, could be treated by antagonizing appropriate cell cycle control genes. Furthermore many human genetic diseases, such as Huntington's disease, and certain prion conditions, which are influenced by both genetic and epigenetic factors, result from the inappropriate activity of a polypeptide as opposed to the complete loss of its function. Accordingly, antagonizing the aberrant function of such mutant genes would provide a means of treatment. Additionally, infectious diseases such as HIV have been successfully treated with molecular antagonists targeted to specific essential retroviral proteins such as HIV protease or reverse transcriptase. Drug therapy strategies for treating such diseases and disorders have frequently employed molecular antagonists which target the polypeptide product of the disease gene(s). However the discovery of relevant gene or protein targets is often difficult and time consuming.

One area of particular interest is the identification of host genes and proteins that are co-opted by viruses during the viral life cycle. The serious and incurable nature of many viral diseases, coupled with the high rate of mutations found in many viruses, makes the identification of antiviral agents a high priority for the improvement of world health. Genes and proteins involved in a viral life cycle are also appealing as a subject for investigation because such genes and proteins will typically have additional activities in the host cell and may play a role in other non-viral disease states.

Viral maturation involves the proteolytic processing of the Gag proteins and the activity of various host proteins. It is believed that cellular machineries for exo/endocytosis and for ubiquitin conjugation may be involved in the maturation. In particular, the assembly, maturation, budding and subsequent release of retroid viruses, RNA viruses and envelope viruses, such as various retroviruses, rhabdoviruses, lentiviruses, and filoviruses may involve the Gag polyprotein. After its synthesis, Gag is targeted to the plasma membrane where it induces budding of nascent virus particles.

The role of ubiquitin in virus assembly was suggested by Dunigan et al. (1988, Virology 165, 310; Meyers et al. 1991, Virology 180, 602), who observed that mature virus particles were enriched in unconjugated ubiquitin. More recently, it was shown that proteasome inhibitors suppress the release of HIV-1, HIV-2 and virus-like particles derived from SIV and RSV Gag. Also, inhibitors affect Gag processing and maturation into infectious particles (Schubert et al 2000, PNAS 97, 13057; Harty et al. 2000, PNAS 97, 13871; Strack et al. 2000, PNAS 97, 13063; Patnaik et al. 2000, PNAS 97, 13069).

It is well known in the art that ubiquitin-mediated proteolysis is the major pathway for the selective, controlled degradation of intracellular proteins in eukaryotic cells. Ubiquitin modification of a variety of protein targets within the cell appears to be important in a number of basic cellular functions such as regulation of gene expression, regulation of the cell-cycle, modification of cell surface receptors, biogenesis of ribosomes, and DNA repair. One major function of the ubiquitin-mediated system is to control the half-lives of cellular proteins. The half-life of different proteins can range from a few minutes to several days, and can vary considerably depending on the cell-type, nutritional and environmental conditions, as well as the stage of the cell-cycle.

Targeted proteins undergoing selective degradation, presumably through the actions of a ubiquitin-dependent proteosome, are covalently tagged with ubiquitin through the formation of an isopeptide bond between the C-terminal glycyl residue of ubiquitin and a specific lysyl residue in the substrate protein. This process is catalyzed by a ubiquitin-activating enzyme (E1) and a ubiquitin-conjugating enzyme (E2), and in some instances may also require auxiliary substrate recognition proteins (E3s). Following the linkage of the first ubiquitin chain, additional molecules of ubiquitin may be attached to lysine side chains of the previously conjugated moiety to form branched multi-ubiquitin chains.

The conjugation of ubiquitin to protein substrates is a multi-step process. In an initial ATP requiring step, a thioester is formed between the C-terminus of ubiquitin and an internal cysteine residue of an E1 enzyme. Activated ubiquitin may then be transferred to a specific cysteine on one of several E2 enzymes. Finally, these E2 enzymes donate ubiquitin to protein substrates, typically with the assistance of a E3 protein, also known as a ubiquitin ligase enzyme. In certain instances, substrates are recognized directly by the ubiquitin-conjugated E2 enzyme. Ubiquitin (ub) protein ligases (E3's) are functionally defined as proteins that facilitate the covalent linkage (conjugation) of one or multiple ubiquitin molecules to a substrate protein in the presence of E1 (ub-activating enzyme) and an E2 (ub carrier protein). In the absence of a protein substrate, E3's can catalyze self-ubiquitination, that is, transfer of activated ubiquitin from E2 to a lysine residue acceptor site on the E3 polypeptide, a reaction termed self-ubiquitination. Similar to trans ubiquitination, self-ubiquitination is dependent on the presence of E1, E2 and an intact E3 functional module i.e. RING finger or HECT domain (Lorick K L et al., Proc Natl Acad Sci USA. 1999 96:11364-9; Kao W H et al., J. Virol. 2000 74:6408-6417).

It is also known that the ubiquitin system plays a role in a wide range of cellular processes including intracellular transport, cell cycle progression, apoptosis, and turnover of many membrane receptors. In viral infections, the ubiquitin system is involved not only with assembly, budding and release, but also with repression of host proteins such as p53, which may lead to a viral-induced neoplasm. The HIV Vpu protein interacts with an E3 protein that regulates IκB degradation, and is thought to promote apoptosis of infected cells by indirectly inhibiting NF-κB activity (Bour et al. (2001) J Exp Med 194:1299-311; U.S. Pat. No. 5,932,425). The ubiquitin system regulates protein function by both monoubiquitination and polyubiquitination. Polyubiquitination is primarily associated with protein degradation.

POSH (Plenty of SH3 domains) proteins play a role in a wide range of cellular processes including protein degradation, intracellular transport, cell cycle progression, apoptosis, and turnover of many membrane receptors. The essential function of POSH, a ubiquitin ligase, and "POSH proteins" (proteins that inherently include in their amino acid sequence a RING domain and at least one SH3 domain) in viral infection and the use of POSH inhibition to inhibit viral infections and, in particular, HIV infection, were broadly described in U.S. application Ser. No. 10/293,965, filed Nov. 12, 2002; PCT/US02/36366, filed Nov. 12, 2002, published as WO 03/095972; PCT/US02/24589, filed Jul. 31, 2002; WO 03/078601, WO 03/060067, EP 1310552, and EP 02257796, filed Nov. 11, 2002. All these applications are hereby incorporated by reference herein in their entirety as if fully disclosed herein.

A ubiquitin ligase, such as POSH, may participate in biological processes including, for example, one or more of the various stages of a viral lifecycle, such as viral entry into a cell, production of viral proteins, assembly of viral proteins and release of viral particles from the cell. In the patent applications mentioned hereinabove, it has been described that certain POSH polypeptides are involved in viral maturation, including the production, post-translational processing, assembly and/or release of proteins in a viral particle. Accordingly, viral infections may be ameliorated by inhibiting an activity (e.g. ubiquitin ligase activity or target protein interaction) of POSH.

In addition, as described in the application PCT/US2004/10582, filed on Apr. 5, 2004, herein incorporated by reference in its entirety, several proteins interact with POSH and may be used to identify candidate therapeutics. One of these POSH-associated proteins (POSH-APs) is HERPUD1, known to be associated with neurological disorders, and in particular with Alzheimer's disease.

It would be beneficial to identify compounds as small molecules that bind POSH proteins and inhibit POSH protein activity and, more specifically, compounds that inhibit POSH protein-mediated ubiquitination.

Throughout this specification, various scientific publications and patents or published patent applications are referenced. The disclosure of all these publications in their entireties is hereby incorporated by reference into this specification in order to more fully describe the state of the art to which this invention pertains. Citation or identification of any reference in this section or any other part of this application shall not be construed as an admission that such reference is available as prior art to the invention.

SUMMARY OF THE INVENTION

In one aspect, the present invention provides a small molecule, which is a pyrimidine derivative of the formula I depicted hereinafter. In preferred embodiments, the compounds of formula I are the compounds herein designated Compounds 1, 2, 3, 4, 5, 6 and 7.

In one aspect, the present invention relates to the use of compounds of the general formula I, for the preparation of a medicament. In preferred embodiments, the compounds used are the compounds herein designated Compounds 1, 2, 3, 4, 5, 6 and 7.

In a preferred embodiment, a compound of formula I is used according to the invention for inhibition of the ubiquitin ligase activity of a human polypeptide.

In another aspect, the present invention relates to a method for inhibiting the ubiquitin ligase activity of a human polypeptide, which comprises administering to a subject in need a compound of formula I in an amount effective for inhibiting the ubiquitin ligase activity of said human polypeptide.

In a preferred embodiment, said human polypeptide contains a RING domain and, more preferably, at least one SH3 domain. In a most preferred embodiment, said polypeptide is a human POSH polypeptide.

The compounds of the general formula I were found to inhibit POSH protein-mediated ubiquitination, and are herein designated "POSH inhibitors".

POSH polypeptides have been identified as playing a role in various stages of a virus lifecycle, including viral maturation, and also in neurological disorders. Thus, inhibition of a POSH polypeptide activity, in particular, POSH protein-mediated ubiquitination, will abolish such activities and will lead to treatment of a viral infection and, eventually, to viral death, or to treatment of a neurological condition, disorder or disease.

In one embodiment, the medicament prepared according to the invention using a compound of formula I, is for the treatment of viral infections.

In another embodiment, the medicament is for the treatment of neurological conditions, disorders or diseases.

In a further aspect, the present invention relates to a method for treatment of a patient suffering from a viral infection, particularly a viral infection caused by a retroid virus, an RNA virus and an envelop virus, including HIV, Ebola, HBV, HCV and HTLV, which comprises administering to said patient an effective amount of at least one compound of the general formula I hereinafter.

In another aspect, the present invention provides a process for the synthesis of Compounds 1 and 2.

DETAILED DESCRIPTION OF THE INVENTION

Figure 1:
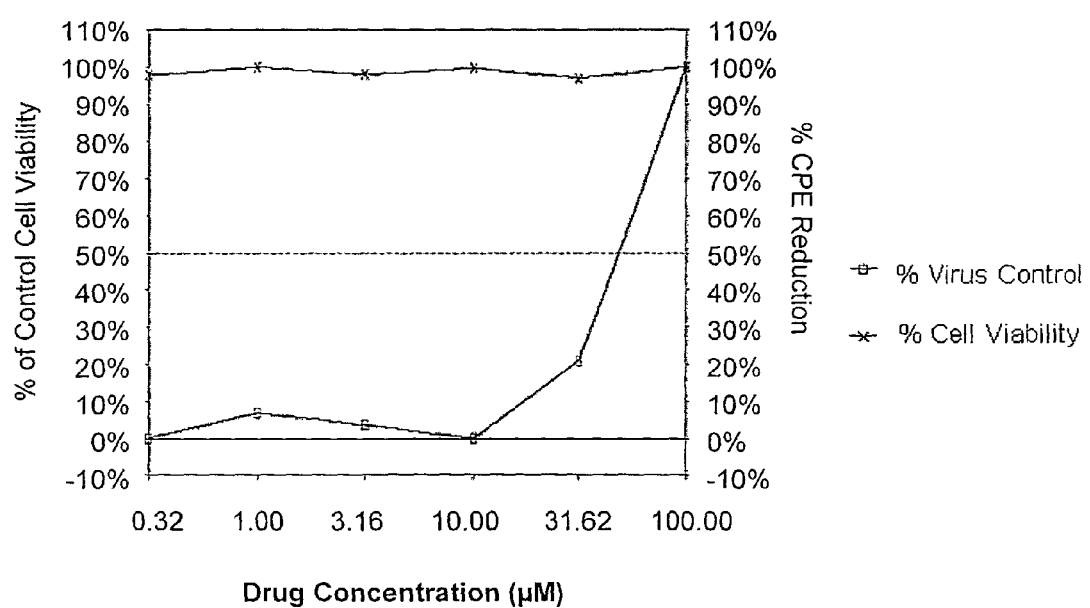
FIG. 1 is a graph showing the antiviral effect of Compound 1 on CEM-SS cells infected with HIV-1$_{IIIB}$ virus, and the cytotoxic effect of Compound 1 on uninfected CEM-SS cells.

It was found, according to the present invention, that certain pyrimidine derivatives act as ubiquitination inhibitors, and are capable of inhibiting POSH protein-mediated ubiquitination.

Thus, according to one aspect, the present invention provides a compound of the general formula I:

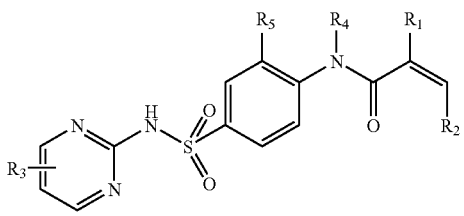

wherein $R_1$ is alkyl, aryl, heteroaryl, —$COR_6$, —$COOR_6$, —$NR_7R_8$, —$CONR_7R_8$ or —$NR_9COR_{10}$;

$R_2$ is aryl or heteroaryl;

$R_3$ represents H or one to three radicals selected from lower alkyl, lower alkoxy, halogen, —$NR_5R_6$, —$COOR_4$ or —$CONR_5R_6$;

$R_4$ is H, alkyl, aryl, carbocyclyl, acyl, →O or heterocyclyl;

$R_5$ is H, halogen, alkyl, aryl, heteroaryl, —$OR_6$, —$SR_6$, —$COR_6$, —$COOR_6$, —$NR_7R_8$, —$CONR_7R_8$ or —$NR_9COR_{10}$; or $R_4$, the nitrogen atom to which it is attached and $R_5$ form a 5-6 membered heterocyclic ring;

$R_6$ is H, hydrocarbyl or heterocyclyl;

$R_7$ and $R_8$ each independently is H, hydrocarbyl or heterocyclyl, or $R_7$ and $R_8$ together with the nitrogen atom to which they are attached form a 5-6 saturated heterocyclic ring, optionally containing 1 or 2 further heteroatoms selected from N, S and/or O, and wherein said further N atom is optionally substituted by lower alkyl, aralkyl, haloalkyl or hydroxyalkyl;

$R_9$ is H, lower alkyl or phenyl;

$R_{10}$ is aryl or heteroaryl;

wherein said hydrocarbyl, heterocyclyl, aryl and heteroaryl is optionally substituted by one or more radicals selected from lower alkyl, halogen, aryl, heterocyclyl, heteroaryl, nitro, epoxy, epithio, —$OR_6$, —$SR_6$, —$COR_6$, —$COOR_6$, —$NR_7R_8$, —$CONR_7R_8$, nitro, —$NR_7$—$COR_6$, —$SO_3R_6$, —$SO_2R_6$, —$SO_2NR_7R_8$ and —$NR_7SO_2R_6$, wherein $R_6$, $R_7$ and $R_8$ are as defined above;

or an enantiomer or a pharmaceutically acceptable salt thereof

In one preferred embodiment, in the compounds of formula I, $R_1$ is $NR_9COR_{10}$, $R_2$ is an optionally substituted heteroaryl and $R_3$ is H or one to three alkyl radicals, and $R_4$-$R_{10}$ are as defined above.

Without limiting the scope to further possible definitions, as used herein in the specification, the terms hereinbelow are defined as follows:

The term "hydrocarbyl" means a radical derived from a hydrocarbon that may be acyclic or cyclic, saturated, unsaturated or aromatic, hydrocarbyl radical, of 1-20 carbon atoms, preferably of 1 to 10, more preferably 1 to 6, most preferably 2-3 carbon atoms, and includes alkyl, alkenyl, alkynyl, cycloalkyl, cycloalkenyl, aralkyl and aryl.

The "alkyl", "alkenyl", or "alkynyl" radical is a "$C_1$-$C_{10}$ alkyl", preferably "$C_1$-$C_4$ alkyl", "$C_2$-$C_{10}$ alkenyl", preferably "$C_2$-$C_4$ alkenyl" or "$C_2$-$C_{10}$ alkynyl", preferably "$C_2$-$C_4$ alkynyl", respectively, that may be straight or branched and may be interrupted by one or more heteroatoms selected from O, S and/or N, and/or substituted by one or more radicals selected from the group consisting of halogen, aryl, heterocyclyl, heteroaryl, nitro, epoxy, epithio, —OR, —SR, —COR, —COOR—NRR', —CONRR', —NRCOR'—$SO_3R'$, —$SO_2R$, —$SO_2NRR'$ and —$NRSO_2R$, wherein R and R', independently, each is H, hydrocarbyl or heterocyclyl, or R and R' together with the nitrogen atom to which they are attached form a saturated 5-7 membered heterocyclic ring, optionally containing 1 or 2 further heteroatoms selected from N, S and/or O, and wherein said further N atom is optionally substituted by hydrocarbyl.

The term "lower alkyl", refers to a "$C_1$-$C_4$ alkyl" that may be straight or branched alkyl radical having 1-4 carbon atoms and may be interrupted by one or more heteroatoms selected from O, S and/or N, and/or substituted as defined above. Lower alkyls include for example methyl, ethyl, n-propyl, isopropyl, n-butyl, isobutyl, tert-butyl. In one preferred embodiment the lower alkyl is methyl.

Any "$C_2$-$C_4$ alkenyl" is a straight or branched unsaturated radical having 2-4 carbon atoms and one or two double bonds, e.g. alkadienyl radical, wherein the alkenyl radical has preferably a terminal double bond, and includes for example vinyl, prop-2-en-1-yl, but-3-en-1-yl. Any "$C_2$-$C_4$ alkynyl" is a straight or branched unsaturated radical having 2-4 carbon atoms and one or more triple bonds and includes, for example, ethynyl, propynyl, butynyl. All alkyl, alkenyl, and alkynyl radicals may be substituted as defined herein.

The term "carbocyclyl" herein includes the terms "cycloalkyl" and "cycloalkenyl", which refer to a "$C_5$-$C_6$ cycloalkyl" or "$C_5$-$C_6$ cycloalkenyl", respectively, namely, 5-6 completely saturated or partially unsaturated carbocyclic groups and include cyclopentyl, cyclohexyl, cyclopentenyl and cyclohexenyl, that may be substituted by one or more radicals selected from the group consisting of halogen, hydrocarbyl, heterocyclyl, nitro, epoxy, epithio, OR, —SR, —COR, —COOR—NRR', —CONRR', —NRCOR'—$SO_3R$, —$SO_2R$, —$SO_2NRR'$ and —$NRSO_2R$, wherein R and R', independently, each is H, hydrocarbyl or heterocyclyl, or R' and R" together with the nitrogen atom to which they are attached form a saturated heterocyclic ring, optionally containing 1 or 2 further heteroatoms selected from N, S and/or O, and wherein said further N atom is optionally substituted by hydrocarbyl.

The term "aryl" refers to a "$C_6$-$C_{14}$" aromatic carbocyclic group having 6 to 14 carbon atoms, preferably 6 to 10 carbon atoms, consisting of a single, bicyclic or tricyclyc ring, such as phenyl, naphthyl and antracenyl, that may be substituted by one or more radicals as defined herein above.

The term "heterocyclyl" means a radical derived from saturated or partially unsaturated (non-aromatic) monocyclic, bicyclic or tricyclic heterocycle, of 3 to 12, preferably 5 to 10, more preferably 5 to 6, ring members, of which ring members one to three is a heteroatom selected from O, S and/or N. Non-limiting examples of non-aromatic heterocyclyl include dihydrofuryl, tetrahydrofuryl, dihydrothienyl, pyrrolydinyl, pyrrolynyl, dihydropyridyl, piperidinyl, piperazinyl, morpholino, 1,3-dioxanyl, and the like. The heterocyclyl radical may be substituted by one or more radicals as defined herein above. It is to be understood that when a polycyclic heterocyclyl ring is substituted, the substitutions may be in any of the carbocyclic and/or heterocyclic rings.

The term "hereroaryl" as used herein, mean a radical derived from a mono- or poly-cyclic heteroaromatic ring containing one to three heteroatoms selected from the group consisting of O, S and N. Particular examples are pyrrolyl, furyl, thienyl, pyrazolyl, imidazolyl, oxazolyl, thiazolyl, pyridyl, quinolinyl, isoquinolinyl, pyridazinyl, pyrimidinyl, pyrazinyl, 1,3,4-triazinyl, 1,2,3-triazinyl, 1,3,5-triazinyl, benzofuryl, isobenzofuryl, indolyl, imidazo[1,2-a]pyridyl, benzimidazolyl, benzthiazolyl and benzoxazolyl, benzodiazepinyl, and other radicals derived from further polycyclic heteroaromatic rings. The heteroaryl radical may be substituted by one or more radicals as defined herein above. It is to be understood that when a polycyclic heteroaryl ring is substituted, the substitutions may be in any of the carbocyclic and/or heterocyclic rings. In one preferred embodiment the heteroaryl is thienyl.

The term "halogen" refers to fluoro, chloro, bromo or iodo. In preferred embodiments, the halogen is chloro.

The groups —$NR_7R_8$ or —NRR' or may be —$NH_2$, when $R_7$ (or R) and $R_8$ (or R') are both hydrogen, or secondary amino when $R_7$ (or R) is H and $R_8$ (or R') is $C_1$-$C_4$ alkyl, or tertiary amino when $R_7$ (or R) and $R_8$ (or R') are each $C_1$-$C_4$ alkyl, or $R_7$ or $R_8$ (R and R', respectively) together with the nitrogen atom to which they are attached may form a saturated, preferably a 5- or 6-membered, heterocyclic ring, optionally containing 1 or 2 further heteroatoms selected from nitrogen, oxygen and/or sulfur. Such rings may be substituted by lower alkyl, aralkyl, haloalkyl or hydroxyalkyl, preferably at a further N atom. Examples of such rings include, without being limited to, pyrrolidino, piperidino, morpholino, thiomorpholino, piperazino, N-alkylpiperazino, e.g. N-methylpiperazino, and diazepino.

Any alkoxy, alkylthio or alkanoyl groups formed by the radicals $OR_6$ (or OR), $SR_6$, (or SR), $COR_6$ (or COR), when $R_6$ (or R) is alkyl, are $C_1$-$C_4$ alkoxy, $C_1$-$C_4$ alkylthio and $C_2$-$C_4$ alkanoyl groups, respectively. Examples of alkoxy are methoxy, ethoxy, propyloxy, butoxy, and the like, and examples of allylthio are the same but replacing the —O— by —S—, and examples of alkanoyl are acetyl, propanoyl, butanoyl, and the like. All alkoxy, thioalkyl, and alkanoyl radicals may be substituted as defined above. In one preferred embodiment, the $C_1$-$C_4$ alkoxy is methoxy.

According to a preferred embodiment, the present invention provides a compound of the formula Ia or Ib:

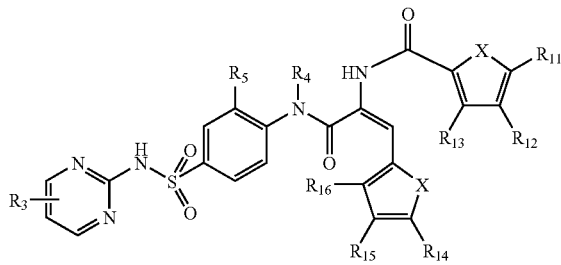
(Ia)

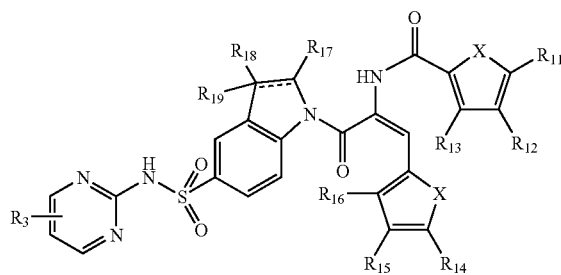
(Ib)

wherein
X is O, S or NH;
$R_3$ is H or one to three ($C_1$-$C_4$) alkyls;
$R_4$ is H or ($C_1$-$C_4$) allyl;
$R_5$ is H or optionally substituted ($C_1$-$C_6$) alkyl;
and $R_{11}$ to $R_{19}$, each independently is selected from H, lower alkyl, halogen, aryl, heterocyclyl, heteroaryl, nitro, epoxy, epithio, —$OR_6$, —$SR_6$, —$COR_6$, —$COOR_6$, —$NR_7R_8$, —$CONR_7R_8$, nitro, —$NR_7$—$COR_6$, —$SO_3R_6$, —$SO_2R_6$, —$SO_2NR_7R_8$ and —$NR_7SO_2R_6$, wherein $R_6$, $R_7$ and $R_8$ each independently is H, alkyl, aryl or heterocyclyl, or $R_7$ and $R_8$ together with the nitrogen atom to which they are attached form a saturated heterocyclic ring, optionally containing 1 or 2 further heteroatoms selected from N, S and/or O, and wherein said further N atom is optionally substituted by lower alkyl, optionally substituted by phenyl, halogen or hydroxy; and the dotted line in formula Ib represents an optional double bond.

In a more preferred embodiment, the compound is of formula Ia, wherein X is S, $R_3$ is H or one to three methyl groups, $R_4$ is H, $R_5$ is H or methyl and $R_{11}$ to $R_{16}$ are H.

In one most preferred compound of formula Ia provided by the present invention are the compounds herein identified as Compounds 1, 2, 3 and 4, wherein Compound 1 is:

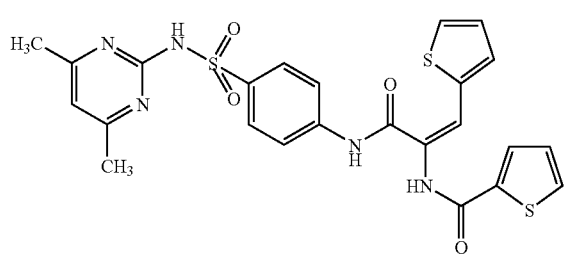

Compound 2 is:

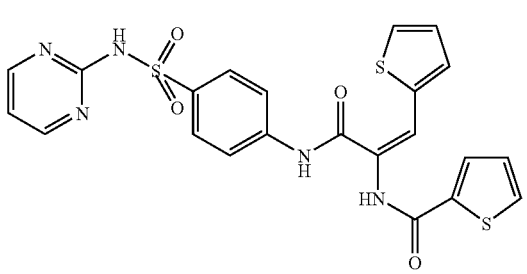

Compound 3 is:

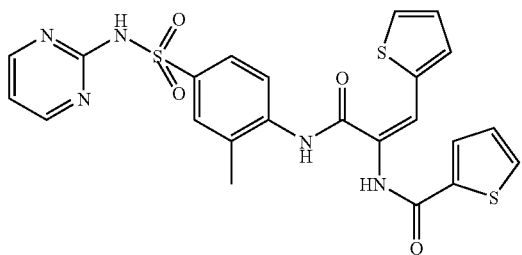

and Compound 4 is:

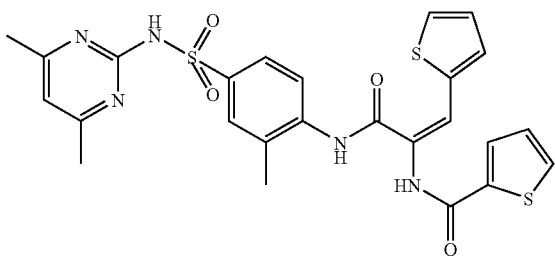

According to another more preferred embodiment, the present invention provides a compound of the formula Ib, wherein X is S, $R_3$ is H or one to three methyl groups and $R_{11}$ to $R_{19}$ are H. In a most preferred embodiments, the compounds is herein identified as Compound 5, 6 and 7, wherein Compound 5 is:

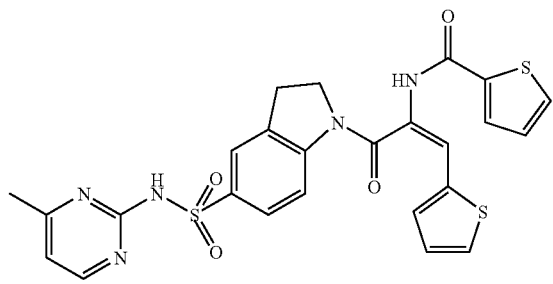

Compound 6 is:

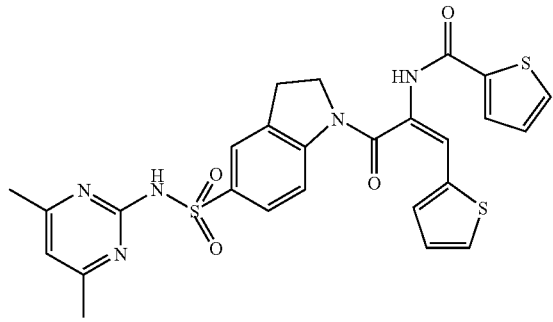

and Compound 7 is:

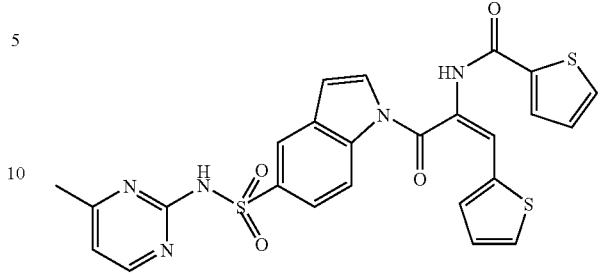

Also contemplated by the present invention are salts of the compounds of formula I, both salts formed by any carboxy or sulfo groups present in the molecule and a base as well as acid addition and/or base salts.

Pharmaceutically acceptable salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, ethylenediamine, N-methylglucamine, and procaine (see, for example, Berge S. M., et al., "Pharmaceutical Salts," (1977) J. of Pharmaceutical Science, 66:1-19). The salts can also be pharmaceutically acceptable quaternary salts such as a quaternary salt of the formula —NRR'R"+Z'— wherein R, R' and R" each is independently hydrogen, alkyl or benzyl and Z is a counterion, including chloride, bromide, iodide, O-alkyl, toluenesulfonate, methylsulfonate, sulfonate, phosphate, carboxylate, acetate or trifluoroacetate.

Pharmaceutically acceptable acid addition salts of the compounds include salts derived from inorganic acids such as hydrochloric, nitric, phosphoric, sulfuric, hydrobromic, hydriodic, phosphorous, and the like, as well as salts derived from organic acids such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, acetate, trifluoroacetate and the like. Also contemplated are salts of amino acids such as arginate and the like and gluconate or galacturonate (see, for example, Berge S. M., et al., "Pharmaceutical Salts," (1977) J. of Pharmaceutical Science, 66:1-19).

The acid addition salts of said basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention.

Compounds 1 and 2 were prepared, in accordance with the present invention, using a three-step reaction procedure as described herein in Examples 7 and 8 and Schemes 1 and 2. The first two steps are known, but the third one is new and involves mixing of 2-(2-thienyl)-4-(2-thienylmethylene)oxazol-5(4H)-one (azalactone, Intermediate 2 in Scheme 1) with 4-amino-N-(4,6-dimethylpyrimidin-2-yl)benzenesulfonamide or with 4-amino-N'-(2-pyrimidinyl)-1-benzenesulfonamide in glacial acetic acid and stirring under reflux.

As used herein, the terms "POSH", "POSH protein(s)" or "POSH polypeptide(s)" are used interchangeably and refer to a polypeptide that includes in its amino acid sequence a RING domain and at list one SH3 domain. In some instances, the POSH protein may have 3 or 4 SH3 domains.

The terms "POSH-mediated ubiquitination" or "POSH protein-mediated ubiquitination" are used interchangeably and refer to any ubiquitination process that requires the involvement of a POSH protein.

The terms "ubiquitination inhibitor", "POSH inhibitor" or "POSH protein inhibitor" are used interchangeably and refer to a pyrimidine derivative of formula I herein that inhibits a POSH activity as defined in PCT/US02/36366 (WO 03/095972), hereby incorporated in its entirety as if fully disclosed herein, including POSH protein-mediated ubiquitination.

POSH polypeptides are known to play a role in various stages of a virus lifecycle, including viral maturation, and also in neurological disorders. Therefore, inhibition of a POSH polypeptide activity, in particular, POSH protein-mediated ubiquitination, by the POSH inhibitors provided by the present invention, may abolish such activities and will lead to treatment of a viral infection and, eventually, to viral death, or to treatment of a neurological condition, disorder or disease.

Thus, in another aspect, the invention relates to the use of a ubiquitination inhibitor for the preparation of a medicament, wherein said ubiquitination inhibitor is a pyrimidine derivative of the general formula I above.

In a preferred embodiment, the POSH polypeptide inhibitors of the general formulas I inhibit the ubiquitin ligase activity of a POSH polypeptide, preferably a human POSH polypeptide. In another preferred embodiments, the POSH inhibitors inhibit POSH selfubiquitination, particularly the RING-finger dependent ubiquitination of the human POSH polypeptide. In a more preferred embodiment, the POSH inhibitors inhibit POSH selectively and do not inhibit the FINGER-dependent ubiquitination of other ubiquitin E3 ligases such as Mdm2 and c-Cbl that have no SH3 domain.

In a preferred embodiment, in the ubiquitination inhibitors used for the preparation of the medicament, $R_1$ is $NR_9COR_{10}$, $R_2$ is an optionally substituted heteroaryl and $R_3$ is H or one to three alkyl radicals. More preferably the inhibitors are of the formula Ia or Ib, most preferably the compounds used are Compounds 1, 2, 3, 4, 5, 6 and 7.

In a most preferred embodiment, the invention provides the use of ubiquitination inhibitors of a general formula I for the preparation of a medicament exhibiting antiviral activity, for treatment of a viral infection, preferably viral infection caused by a retroid virus such as an RNA virus, an envelope virus, or a lentivirus, including primate lentivirus group, most preferably viral infections caused by infection is caused by a virus selected from the group consisting of human immunodeficiency virus (HIV), human immunodeficiency virus type-1 (HIV-1), human immunodeficiency virus type-2 (HIV-2), hepatitis B virus (HBV), hepatitis C virus (HCV), Ebola virus, and human T-cell leukemia Virus (HTLV). In preferred embodiments, the compounds are as defined above in the preferred embodiments for the use of compounds of formula I, most preferably Compounds 1, 2 and 5.

In still another aspect, the present invention relates to a method for treatment of a patient suffering from a viral infection, which comprises administering to said patient an effective amount of at least one pyrimidine derivative of a general formula I hereinabove.

According to the invention, it is envisaged that the POSH protein inhibitors will be useful for the treatment of any viral infection.

In view of the teachings herein, one of skill in the art will understand that the methods and compositions of the invention are applicable to a wide range of viruses such as for example retroid viruses, RNA viruses, and envelope viruses.

The term "envelope virus" as used herein refers to any virus that uses cellular membrane and/or any organelle membrane in the viral release process.

In a preferred embodiment, the present invention is applicable to retroid viruses. In a more preferred embodiment, the present invention is further applicable to retroviruses (retroviridae). In another more preferred embodiment, the present invention is applicable to lentivirus, including primate lentivirus group. In a most preferred embodiment, the present invention is applicable to Human Immunodeficiency virus (HIV), Human Immunodeficiency virus type-1 (HIV-1), Human Immunodeficiency virus type-2 (HIV-2), Hepatitis B Virus (HBV), and Human T-cell Leukemia Virus (HTLV).

While not intended to be limiting, relevant retroviruses include: C-type retrovirus which causes lymphosarcoma in Northern Pike, the C-type retrovirus which infects mink, the caprine lentivirus which infects sheep, the Equine Infectious Anemia Virus (EIAV), the C-type retrovirus which infects pigs, the Avian Leukosis Sarcoma Virus (ALSV), the Feline Leukemia Virus (FeLV), the Feline Aids Virus, the Bovine Leukemia Virus (BLV), the Simian Leukemia Virus (SLV), the Simian Immuno-deficiency Virus (SIV), the Human T-cell Leukemia Virus type-I (HTLV-I), the Human T-cell Leukemia Virus type-II (HTLV-II), Human Immunodeficiency virus type-2 (HIV-2) and Human Immunodeficiency virus type-1 (HIV-1).

The method and compositions of the present invention are further applicable to RNA viruses, including ssRNA negative-strand viruses and ssRNA positive-strand viruses. The ssRNA positive-strand viruses include Hepatitis C Virus (HCV). In a preferred embodiment, the present invention is applicable to mononegavirales, including filoviruses. Filoviruses further include Ebola viruses and Marburg viruses.

Other RNA viruses include picornaviruses such as enterovirus, poliovirus, coxsaclievirus and hepatitis A virus, the caliciviruses, including Norwalk-like viruses, the rhabdoviruses, including rabies virus, the togaviruses including alphaviruses, Semliki Forest virus, denguevirus, yellow fever virus and rubella virus, the orthomyxoviruses, including Type A, B, and C influenza viruses, the bunyaviruses, including the Rift Valley fever virus and the hantavirus, the filoviruses such as Ebola virus and Marburg virus, and the paramyxoviruses, including mumps virus and measles virus. Additional viruses that may be treated include herpes viruses.

In a preferred feature according to a preferred embodiment of the invention, the viral infection is caused by a retroid virus.

In another preferred feature according to a preferred embodiment of the invention, the viral infection is caused by an RNA virus.

In a further preferred feature according to a preferred embodiment of the invention, the viral infection is caused by an envelope virus.

In still another preferred feature according to a preferred embodiment of the invention, the viral infection is caused by a human immunodeficiency virus (HIV), particularly HIV-1 or HIV-2.

In still a further preferred feature according to a preferred embodiment of the invention, the viral infection is caused by Ebola virus.

In still another preferred feature according to a preferred embodiment of the invention, the viral infection is caused by hepatitis B virus (HBV).

In still another preferred feature according to a preferred embodiment of the invention, the viral infection is caused by hepatitis C virus (HCV).

In still another preferred feature according to a preferred embodiment of the invention, the viral infection is caused by a human T-cell leukemia virus (HTLV) such as HTLV type 1 (HTLV-1).

In a most preferred embodiment of the present invention, the compound used for the treatment of viral infections, preferably of viral infections caused by a HIV virus, are the compound herein identified as Compounds 1, 2 and 5.

In another most preferred embodiment, the invention provides pharmaceutical compositions for treatment of neurological conditions, disorders or diseases comprising a pharmaceutically acceptable carrier and a pyrimidine derivative of a general formula I. In preferred embodiments, the compounds are as defined above in the preferred embodiments for the pharmaceutical compositions.

In still another aspect, the present invention relates to a method for treatment of a patient suffering from a neurological condition, disorder or disease, which comprises administering to said patient an effective amount of at least one pyrimidine derivative of a general formula I hereinabove.

According to the present invention, any neurological condition, disorder or disease may be treated with the compounds of formula I including, without limitation, Alzheimer's disease, Parkinson's disease, Huntington's disease, Pick's disease, cerebral vascular disease, depression or schizophrenia.

In a preferred feature according to a preferred embodiment of the invention, the neurological disease is Alzheimer's disease. According to this feature, the present invention provides a method of inhibiting amyloid polypeptide production in a cell comprising administering a small molecule agent that inhibits the ubiquitin ligase activity of a human polypeptide or protein, wherein said small molecule compound is a pyrimidine derivative of formula I hereinabove. In another embodiment, the invention provides a method of inhibiting the transport of amyloid precursor protein (APP) in a cell comprising inhibiting the ubiquitin ligase activity of a polypeptide with a small molecule, wherein said small molecule compound is a pyrimidine derivative of formula I.

The pharmaceutical compositions for use in accordance with the present invention may be formulated in conventional manner using one or more physiologically acceptable carriers or excipients. Thus, the compounds and their physiologically acceptable salts and solvates may be formulated by conventional methods as described, for example, in Remington's Pharmaceutical Sciences, Meade Publishing Co., Easton, Pa., for administration by a variety of routes of administration, including systemic and topical or localized administration.

For systemic administration, injection is preferred, including intramuscular, intravenous, intraperitoneal, and subcutaneous. For injection, the compounds of the invention can be formulated in liquid solutions, preferably in physiologically compatible buffers such as Hank's solution or Ringer's solution. In addition, the compounds may be formulated in solid form and redissolved or suspended immediately prior to use. Lyophilized forms are also included.

For oral administration, the pharmaceutical compositions may take the form of, for example, tablets or capsules prepared by conventional means with pharmaceutically acceptable excipients such as binding agents; fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., ationd oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound. For buccal administration the compositions may take the form of tablets or lozenges formulated in conventional manner. For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetra-fluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays or using suppositories. For topical administration, the compounds of the invention are formulated into ointments, salves, gels, or creams as generally known in the art. A wash solution can be used locally to treat an injury or inflammation to accelerate healing.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

POSH intersects with and regulates a wide range of key cellular functions that may be manipulated by affecting the level of and/or activity of POSH polypeptides or POSH-AP polypeptides. Many features of POSH, and particularly human POSH, are described in PCT patent publications WO03/095971A2 and WO03/078601A2, the teachings of which are incorporated by reference herein.

As described in the above-referenced publications, native human POSH is a large polypeptide containing a RING domain and four SH3 domains. POSH is a ubiquitin ligase (also termed an "E3" enzyme); the RING domain mediates ubiquitination of, for example, the POSH polypeptide itself. POSH interacts with a large number of proteins and participates in a host of different biological processes. As demonstrated in this disclosure, POSH associates with a number of different proteins in the cell. POSH co-localizes with proteins that are known to be located in the trans-Golgi network, implying that POSH participates in the trafficking of proteins in the secretory system. The term "secretory system" should be understood as referring to the membrane compartments and associated proteins and other molecules that are involved in the movement of proteins from the site of translation to a location within a vacuole, a compartment in the secretory pathway itself, a lysosome or endosome or to a location at the plasma membrane or outside the cell. Commonly cited examples of compartments in the secretory system include the endoplasmic reticulum, the Golgi apparatus and the cis and trans Golgi networks.

In addition, Applicants have demonstrated that POSH is necessary for proper secretion, localization or processing of a variety of proteins, including phospholipase D, HIV Gag, HIV Nef, Rapsyn and Src. Many of these proteins are myristoylated, indicating that POSH plays a general role in the processing and proper localization of myristoylated proteins. Accordingly, in certain aspects, POSH may play a role in the processing and proper localization of myristolyated proteins. N-myristoylation is an acylation process, which results in covalent attachment of myristate, a 14-carbon saturated fatty acid to the N-terminal glycine of proteins (Farazi et al., J. Biol. Chem. 276: 39501-04 (2001)). N-myristoylation occurs co-translationaly and promotes weak and reversible protein-membrane interaction. Myristoylated proteins are found both in the cytoplasm and associated with membrane. Membrane association is dependent on protein configuration, i.e., surface accessibility of the myristoyl group may be regulated by protein modifications, such as phosphorylation, ubiquitination etc. Modulation of intracellular transport of myristoylated proteins in the application includes effects on transport and localization of these modified proteins.

An "E1" is a ubiquitin activating enzyme. In a preferred embodiment, E1 is capable of transferring ubiquitin to an E2. In a preferred embodiment, E1 forms a high energy thiolester bond with ubiquitin, thereby "activating" the ubiquitin. An "E2" is a ubiquitin carrier enzyme (also known as a ubiquitin conjugating enzyme). In a preferred embodiment, ubiquitin is transferred from E1 to E2. In a preferred embodiment, the transfer results in a thiolester bond formed between E2 and ubiquitin. In a preferred embodiment, E2 is capable of transferring ubiquitin to a POSH polypeptide.

In certain embodiments, the agents of the invention identified are antiviral agents, optionally interfering with viral maturation, and preferably where the virus is a retroid virus, an RNA virus and an envelope virus.

In certain preferred embodiments, an antiviral agent interferes with the ubiquitin ligase (catalytic) activity of POSH (e.g. POSH auto-ubiquitination or transfer to a target protein).

In additional certain preferred embodiments, an antiviral agent interferes with the interaction between POSH and a POSH-AP (adaptor) polypeptide, for example an antiviral agent may disrupt or render irreversible the interaction between a POSH polypeptide and POSH-AP polypeptide such as another POSH polypeptide (as in the case of a POSH dimer, a heterodimer of two different POSH polypeptides, homomultimers and heteromultimers); a GTPase (eg. Rac, Rac1, Rho, Ras); an E2 enzyme and ubiquitin, or optionally, a cullin; a clathrin; AP-1; AP-2; an HSP70; an HSP90, Brca1, Bard1, Nef, PAK1, PAK2, PAK family, Vav, Cdc42, PI3K (e.g. p85 or p110), Nedd4, src (src family), a Gag, particularly an HIV Gag (e.g. p160), Tsg101, VASP, RNB6, WASP, N-WASP and KIAA0674, similar to Spred-2, as well as, in certain embodiments, proteins known to be associated with clathrin-coated vesicles and or proteins involved in the protein sorting pathway.

In yet additional embodiments, agents of the invention interfere with the signaling of a GTPase, such as Rac or Ras, optionally disrupting the interaction between a POSH polypeptide and a Rac protein.

In certain embodiments, agents of the invention modulate the ubiquitin ligase activity of POSH and may be used to treat certain diseases related to ubiquitin ligase activity.

In other certain embodiments, the invention discloses assays to identify, optimize or otherwise assess agents that decrease a ubiquitin-related activity of a POSH polypeptide. Ubiquitin-related activities of POSH polypeptides may include the self-ubiquitination activity of a POSH polypeptide, generally involving the transfer of ubiquitin from an E2 enzyme to the POSH polypeptide, and the ubiquitination of a target protein (e.g., HERPUD1), generally involving the transfer of a ubiquitin from a POSH polypeptide to the target protein. In certain embodiments, a POSH activity is mediated, at least in part, by a POSH RING domain.

In still other certain embodiments, an assay comprises forming a mixture comprising a POSH polypeptide, an E2 polypeptide and a source of ubiquitin (which may be the E2 polypeptide pre-complexed with ubiquitin). Optionally the mixture comprises an E1 polypeptide and optionally the mixture comprises a target polypeptide, such as, for example, HERPUD1. Additional components of the mixture may be selected to provide conditions consistent with the ubiquitination of the POSH polypeptide. One or more of a variety of parameters may be detected, such as POSH-ubiquitin conjugates, E2-ubiquitin thioesters, free ubiquitin and target polypeptide-ubiquitin complexes.

The term "detect" is used herein to include a determination of the presence or absence of the subject of detection (e.g. POSH-ubiquitin, E2-ubiquitin, etc.), a quantitative measure of the amount of the subject of detection, or a mathematical calculation of the presence, absence or amount of the subject of detection, based on the detection of other parameters. The term "detect" includes the situation wherein the subject of detection is determined to be absent or below the level of sensitivity. Detection may comprise detection of a label (e.g. fluorescent label, radioisotope label, and other described below), resolution and identification by size (e.g. SDS-PAGE, mass spectroscopy), purification and detection, and other methods that, in view of this specification, will be available to one of skill in the art. For instance, radioisotope labeling may be measured by scintillation counting, or by densitometry after exposure to a photographic emulsion, or by using a device such as a Phosphorimager. Likewise, densitometry may be used to measure bound ubiquitin following a reaction with an enzyme label substrate that produces an opaque product when an enzyme label is used. In a preferred embodiment, an assay comprises detecting the POSH-ubiquitin conjugate.

In certain embodiments, an assay comprises forming a mixture comprising a POSH polypeptide, a target polypeptide and a source of ubiquitin (which may be the POSH polypeptide pre-complexed with ubiquitin). Optionally the mixture comprises an E1 and/or E2 polypeptide and optionally the mixture comprises an E2-ubiquitin thioester. Additional components of the mixture may be selected to provide conditions consistent with the ubiquitination of the target polypeptide. One or more of a variety of parameters may be detected, such as POSH-ubiquitin conjugates and target polypeptide-ubiquitin conjugates. In a preferred embodiment, an assay comprises detecting the target polypeptide-ubiquitin conjugate, such as, for example, detecting ubiquitinated HERPUD1. In another preferred embodiment, an assay comprises detecting the POSH-ubiquitin conjugate.

An assay described above may be used in a screening assay to identify agents that modulate a ubiquitin-related activity of a POSH polypeptide. A screening assay will generally involve adding a test agent to one of the above assays, or any other assay designed to assess a ubiquitin-related activity of a POSH polypeptide. The parameter(s) detected in a screening assay may be compared to a suitable reference. A suitable reference may be an assay run previously, in parallel or later that omits the test agent. A suitable reference may also be an average of previous measurements in the absence of the test agent. In general the components of a screening assay mixture may be added in any order consistent with the overall activity to be assessed, but certain variations may be preferred. For example, in certain embodiments, it may be desirable to pre-incubate the test agent and the E3 (e.g. the POSH polypeptide), followed by removing the test agent and addition of other components to complete the assay. In this manner, the effects of the agent solely on the POSH polypeptide may be assessed. In certain preferred embodiments, a screening assay for an antiviral agent employs a target polypeptide comprising an L domain, and preferably an HIV L domain.

In certain embodiments, an assay is performed in a high-throughput format. For example, one of the components of a mixture may be affixed to a solid substrate and one or more of the other components is labeled. For example, the POSH polypeptide may be affixed to a surface, such as a 96-well plate, and the ubiquitin is in solution and labeled. An E2 and E1 are also in solution, and the POSH-ubiquitin conjugate formation may be measured by washing the solid surface to remove uncomplexed labeled ubiquitin and detecting the ubiquitin that remains bound. Other variations may be used. For example, the amount of ubiquitin in solution may be detected.

In certain embodiments, the formation of ubiquitin complexes may be measured by an interactive technique, such as FRET, wherein a ubiquitin is labeled with a first label and the desired complex partner (e.g. POSH polypeptide or target polypeptide) is labeled with a second label, wherein the first and second label interact when they come into close proximity to produce an altered signal. In FRET, the first and second labels are fluorophores. FRET is described in greater detail below. The formation of polyubiquitin complexes may be performed by mixing two or more pools of differentially labeled ubiquitin that interact upon formation of a polyubiquitin (see, e.g. US Patent Publication 20020042083). High-throughput screening may be achieved by performing an interactive assay, such as FRET, in solution as well. In addition, if a polypeptide in the mixture, such as the POSH polypeptide or target polypeptide, is readily purifiable (e.g. with a specific antibody or via a tag such as biotin, FLAG, polyhistidine, etc.), the reaction may be performed in solution and the tagged polypeptide rapidly isolated, along with any polypeptides, such as ubiquitin, that are associated with the tagged polypeptide. Proteins may also be resolved by SDS-PAGE for detection.

In certain embodiments, the ubiquitin is labeled, either directly or indirectly. This typically allows for easy and rapid detection and measurement of ligated ubiquitin, making the assay useful for high-throughput screening applications. As described above, certain embodiments may employ one or more tagged or labeled proteins. A "tag" is meant to include moieties that facilitate rapid isolation of the tagged polypeptide. A tag may be used to facilitate attachment of a polypeptide to a surface. A "label" is meant to include moieties that facilitate rapid detection of the labeled polypeptide. Certain moieties may be used both as a label and a tag (e.g. epitope tags that are readily purified and detected with a well-characterized antibody). Biotinylation of polypeptides is well known, for example, a large number of biotinylation agents are known, including amine-reactive and thiol-reactive agents, for the biotinylation of proteins, nucleic acids, carbohydrates, carboxylic acids (see chapter 4, Molecular Probes Catalog, Haugland, 6th Ed. 1996, hereby incorporated by reference). A biotinylated substrate can be attached to a biotinylated component via avidin or streptavidin. Similarly, a large number of haptenylation reagents are also known.

In an alternative embodiment, a POSH polypeptide, E2 or target polypeptide is bound to a bead, optionally with the assistance of a tag. Following ligation, the beads may be separated from the unbound ubiquitin and the bound ubiquitin measured. In a preferred embodiment, POSH polypeptide is bound to beads and the composition used includes labeled ubiquitin. In this embodiment, the beads with bound ubiquitin may be separated using a fluorescence-activated cell sorting (FACS) machine. Methods for such use are described in U.S. patent application Ser. No. 09/047,119, which is hereby incorporated by reference in its entirety. The amount of bound ubiquitin can then be measured.

In a screening assay, the effect of a test agent may be assessed by, for example, assessing the effect of the test agent on kinetics, steady-state and/or endpoint of the reaction.

The components of the various assay mixtures provided herein may be combined in varying amounts. In a preferred embodiment, ubiquitin (or E2 complexed ubiquitin) is used at a final concentration of from 5 to 200 ng per 100 microliter reaction solution. Optionally E1 is used at a final concentration of from 1 to 50 ng per 100 microliter reaction solution. Optionally E2 is used at a final concentration of 10 to 100 ng per 100 microliter reaction solution, more preferably 10-50 ng per 100 microliter reaction solution. In a preferred embodiment, POSH polypeptide is used at a final concentration of from 1 ng to 500 ng per 100 microliter reaction solution.

Generally, an assay mixture is prepared so as to favor ubiquitin ligase activity and/or ubiquitination activity. Generally, this will be physiological conditions, such as 50-200 mM salt (e.g. NaCl, KCl), pH of between 5 and 9, and preferably between 6 and 8. Such conditions may be optimized through trial and error. Incubations may be performed at any temperature which facilitates optimal activity, typically between 4 and 40 degrees C. Incubation periods are selected fot optimum activity, but may also be optimized to facilitate high through put screening. Typically between 0.5 and 1.5 hours will be sufficient.

A variety of other reagents may be included in the compositions. These include reagents like salts, solvents, buffers, neutral proteins, e.g. albumin, detergents, etc. which may be used to facilitate optimal ubiquitination enzyme activity and/or reduce non-specific or background interactions.

Also reagents that otherwise improve the efficiency of the assay, such as protease inhibitors, nuclease inhibitors, antimicrobial agents, etc., may be used. The compositions will also preferably include adenosine tri-phosphate (ATP).

The mixture of components may be added in any order that promotes ubiquitin ligase activity or optimizes identification of candidate modulator effects. In a preferred embodiment, ubiquitin is provided in a reaction buffer solution, followed by addition of the ubiquitination enzymes. In an alternate preferred embodiment, ubiquitin is provided in a reaction buffer solution, a candidate modulator is then added, followed by addition of the ubiquitination enzymes.

In general, a test agent that decreases a POSH ubiquitin-related activity may be used to inhibit POSH function in vivo. The test agent may be modified for use in vivo, e.g. by addition of a hydrophobic moiety, such as an ester.

Certain embodiments of the invention relate to assays for identifying agents that bind to a POSH polypeptide or POSH-AP, such as HERPUD1, or optionally, a particular domain of POSH such as an SH3 or RING domain. In preferred embodiments, a POSH polypeptide is a polypeptide comprising the fourth SH3 domain of hPOSH (SEQ ID NO: 30 as described in). A wide variety of assays may be used for this purpose, including labeled in vitro protein-protein binding assays, electrophoretic mobility shift assays, immunoassays for protein binding, and the like. The purified protein may also be used for determination of three-dimensional crystal structure, which can be used for modeling intermolecular interactions and design of test agents. In one embodiment, an assay detects agents which inhibit interaction of one or more subject POSH polypeptides with a POSH-AP. In another embodiment, the assay detects agents, which modulate the intrinsic biological activity of a POSH polypeptide or POSH complex, such as an enzymatic activity, binding to other cellular components, cellular compartmentalization, and the like.

In one aspect, the invention provides methods and compositions for the identification of compositions that interfere with the function of POSH polypeptides or POSH-AP, such as HERPUD1. Given the role of POSH polypeptides in viral production, compositions that perturb the formation or stability of the protein-31' protein interactions between POSH polypeptides and the proteins that they interact with, such as POSH-APs, and particularly POSH complexes comprising a viral protein, are candidate pharmaceuticals for the treatment of viral infections.

While not wishing to be bound to mechanism, it is postulated that POSH polypeptides promote the assembly of protein complexes that are important in release of virions and other biological processes. Complexes of the invention may include a combination of a POSH polypeptide and one or more of the following POSH-APs: a POSH-AP; a POSH polypeptide (as in the case of a POSH dimer, a heterodimer of two different POSH, homomultimers and heteromultimers); Vpu; Cbl-b; PKA; UNC84; MSTP028; HERPUD1; GOCAP1; PTPN12; EIF3S3; SAR1; GOSR2; RALA; SIAH; SMINI; SMN2; SYNE1; TTC3; VCY2IP1; SAM68; gag-pol; a GTPase an E2 enzyme; ubiquitin, or optionally, a cullin; a clathrin; AP-1; AP-2; an HSP70; an HSP90, Brca1, Bard1, Nef, PAK1, PAK2, PAK family, Vav, Cdc42, PI3K (e.g. p85 or p110), Nedd4, src (src family), Tsg101, VASP, RNB6, WASP, N-WASP, a Gag, particularly an HIV Gag (e.g. p160); and KLAA0674, Similar to Spred-2, as well as, in certain embodiments, proteins known to be associated with clathrin-coated vesicles and or proteins involved in the protein sorting pathway.

The type of complex formed by a POSH polypeptide will depend upon the domains present in the protein. While not intended to be limiting, exemplary domains of potential interacting proteins are provided below. A RING domain is expected to interact with cullins, E2 enzymes, AP-1, AP-2, and/or a substrate for ubiquitylation (e.g. in some instances, a protein comprising a Gag L domain or a Gag polypeptide such as Gag-Pol, such as HIV p160). An SH3 domain may interact with Gag L domains and other proteins having the sequence motifs as disclosed in WO03/095971, the teachings of which are incorporated by reference herein.

In a preferred assay for an antiviral agent, the test agent is assessed for its ability to disrupt or inhibit the formation of a complex of a POSH polypeptide and a Rac polypeptide, particularly a human Rac polypeptide, such as Rac1.

A variety of assay formats will suffice and, in light of the present disclosure, those not expressly described herein will nevertheless be comprehended by one of ordinary skill in the art. Assay formats which approximate such conditions as formation of protein complexes, enzymatic activity, and even a POSH polypeptide-mediated membrane reorganization or vesicle formation activity, may be generated in many different forms, and include assays based on cell-free systems, e.g. purified proteins or cell lysates, as well as cell-based assays which utilize intact cells. Simple binding assays can also be used to detect agents, which bind to POSH. Such binding assays may also identify agents that act by disrupting the interaction between a POSH polypeptide and a POSH interacting protein, or the binding of a POSH polypeptide or complex to a substrate. Agents to be tested can be produced, for example, by bacteria, yeast or other organisms (e.g. natural products), produced chemically (e.g. small molecules, including peptidomimetics), or produced recombinantly. In a preferred embodiment, the test agent is a small organic molecule, e.g., other than a peptide or oligonucleotide, having a molecular weight of less than about 2,000 daltons.

In many drug-screening programs, which test libraries of compounds and natural extracts, high throughput assays are desirable in order to maximize the number of compounds surveyed in a given period of time. Assays of the present invention which are performed in cell-free systems, such as may be developed with purified or semi-purified proteins or with lysates, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifested in an alteration of binding affinity with other proteins or changes in enzymatic properties of the molecular target.

In preferred embodiments of the present assay, a reconstituted POSH complex comprises a reconstituted mixture of at least semi-purified proteins. By semi-purified, it is meant that the proteins utilized in the reconstituted mixture have been previously separated from other cellular or viral proteins. For instance, in contrast to cell lysates, the proteins involved in POSH complex formation are present in the mixture to at least 50% purity relative to all other proteins in the mixture, and more preferably are present at 90-95% purity. In certain embodiments of the subject method, the reconstituted protein mixture is derived by mixing highly purified proteins such that the reconstituted mixture substantially lacks other proteins (such as of cellular or viral origin), which might interfere with or otherwise alter the ability to measure POSH complex assembly and/or disassembly.

Assaying POSH complexes, in the presence and absence of a candidate inhibitor, can be accomplished in any vessel suitable for containing the reactants. Examples include microtitre plates, test tubes, and micro-centrifuge tubes.

In one embodiment of the present invention, drug screening assays can be generated which detect inhibitory agents on the basis of their ability to interfere with assembly or stability of the POSH complex. In an exemplary binding assay, the compound of interest is contacted with a mixture comprising a POSH polypeptide and at least one interacting polypeptide. Detection and quantification of POSH complexes provides a means for determining the compound's efficacy at inhibiting interaction between the two polypeptides. The efficacy of the compound can be assessed by generating dose response curves from data obtained using various concentrations of the test compound. Moreover, a control assay can also be performed to provide a baseline for comparison. In the control assay, the formation of complexes is quantitated in the absence of the test compound.

Complex formation between the POSH polypeptides and a substrate polypeptide may be detected by a variety of techniques, many of which are effectively described above. For instance, modulation of the formation of complexes can be quantitated using, detectably labeled proteins (e.g. radiolabeled, fluorescently labeled, or enzymatically labeled), by immunoassay, or by chromatographic detection. Surface plasmon resonance systems, such as those available from Biacore International AB (Uppsala, Sweden), may also be used to detect protein-protein interaction Often, it will be desirable to immobilize one of the polypeptides to facilitate separation of complexes from uncomplexed forms of one of the proteins, as well as to accommodate automation of the assay. In an illustrative embodiment, a fusion protein can be provided which adds a domain that permits the protein to be bound to an insoluble matrix. For example, GST-POSH fusion proteins can be adsorbed onto glutathione sepharose beads (Sigma Chemical, St. Louis, Mo.) or glutathione derivatized microtitre plates, which are then combined with a potential interacting protein, e.g. an 35S-labeled polypeptide, and the test compound and incubated under conditions conducive to complex formation. Following incubation, the beads are washed to remove any unbound interacting protein, and the matrix bead-bound radiolabel determined directly (e.g. beads placed in scintillant), or in the supernatant after the complexes are dissociated, e.g. when microtitre plate is used. Alternatively, after washing away unbound protein, the complexes can be dissociated from the matrix, separated by SDS-PAGE gel, and the level of interacting polypeptide found in the matrix-bound fraction quantitated from the gel using standard electrophoretic techniques.

In another embodiment, the POSH polypeptide and potential interacting polypeptide can be used to generate an interaction trap assay (see also, U.S. Pat. No. 5,283,317; Zervos et al. (1993) Cell 72:223-232; Madura et al. (1993) J Biol Chem 268:12046-12054; Bartel et al. (1993) Biotechniques 14:920-924; and Iwabuchi et al. (1993) Oncogene 8:1693-1696), for subsequently detecting agents which disrupt binding of the proteins to one and other.

In still further embodiments of the present assay, the POSH complex is generated in whole cells, taking advantage of cell culture techniques to support the subject assay. For example, as described below, the POSH complex can be constituted in a eukaryotic cell culture system, including mammalian and yeast cells. Often it will be desirable to express one or more viral proteins (eg. Gag or Env) in such a cell along with a subject POSH polypeptide. It may also be desirable to infect the cell with a virus of interest. Advantages to generating the subject assay in an intact cell include the ability to detect inhibitors which are functional in an environment more closely approximating that which therapeutic use of the inhibitor would require, including the ability of the agent to gain entry into the cell. Furthermore, certain of the in vivo embodiments of the assay, such as examples given below, are amenable to high-throughput analysis of candidate agents.

The components of the POSH complex can be endogenous to the cell selected to support the assay. Alternatively, some or all of the components can be derived from exogenous sources. For instance, fusion proteins can be introduced into the cell by recombinant techniques (such as through the use of an expression vector), as well as by microinjecting the fusion protein itself or mRNA encoding the fusion protein.

In many embodiments, a cell is manipulated after incubation with a candidate agent and assayed for a POSH activity. In certain embodiments a POSH activity is represented by production of virus like particles. As demonstrated herein, an agent that disrupts POSH activity can cause a decrease in the production of virus like particles. In certain embodiments, POSH activities may include, without limitation, complex formation, ubiquitination and membrane fusion events (eg. release of viral buds or fusion of vesicles). POSH complex formation may be assessed by immunoprecipitation and analysis of co-immunoprecipiated proteins or affinity purification and analysis of co-purified proteins. Fluorescence Resonance Energy Transfer (FRET)-based assays may also be used to determine complex formation. Fluorescent molecules having the proper emission and excitation spectra that are brought into close proximity with one another can exhibit FRET. The fluorescent molecules are chosen such that the emission spectrum of one of the molecules (the donor molecule) overlaps with the excitation spectrum of the other molecule (the acceptor molecule). The donor molecule is excited by light of appropriate intensity within the donor's excitation spectrum. The donor then emits the absorbed energy as fluorescent light. The fluorescent energy it produces is quenched by the acceptor molecule. FRET can be manifested as a reduction in the intensity of the fluorescent signal from the donor, reduction in the lifetime of its excited state, and/or re-emission of fluorescent light at the longer wavelengths (lower energies) characteristic of the acceptor. When the fluorescent proteins physically separate, FRET effects are diminished or eliminated. (U.S. Pat. No. 5,981,200).

For example, a cyan fluorescent protein (CFP) is excited by light at roughly 425-450 nm wavelength and emits light in the range of 450-500 nm. Yellow fluorescent protein (YFP) is excited by light at roughly 500-525 nm and emits light at 525-500 nm. If these two proteins are placed in solution, the cyan and yellow fluorescence may be separately visualized. However, if these two proteins are forced into close proximity with each other, the fluorescent properties will be altered by FRET. The bluish light emitted by CFP will be absorbed by YFP and re-emitted as yellow light. This means that when the proteins are stimulated with light at wavelength 450 nm, the cyan emitted light is greatly reduced and the yellow light, which is not normally stimulated at this wavelength, is greatly increased. FRET is typically monitored by measuring the spectrum of emitted light in response to stimulation with light in the excitation range of the donor and calculating a ratio between the donor-emitted light and the acceptor-emitted light. When the donor:acceptor emission ratio is high, FRET is not occurring and the two fluorescent proteins are not in close proximity. When the donor:acceptor emission ratio is low, FRET is occurring and the two fluorescent proteins are in close proximity. In this manner, the interaction between a first and second polypeptide may be measured.

The occurrence of FRET also causes the fluorescence lifetime of the donor fluorescent moiety to decrease. This change in fluorescence lifetime can be measured using a technique termed fluorescence lifetime imaging technology (FLIM) (Verveer et al. (2000) *Science* 290: 1567-1570; Squire et al. (1999) *J. Microsc.* 193: 36; Veiveer et al. (2000) *Biophys. J.* 78: 2127). Global analysis techniques for analyzing FLIM data have been developed. These algorithms use the understanding that the donor fluorescent moiety exists in only a limited number of states each with a distinct fluorescence lifetime. Quantitative maps of each state can be generated on a pixel-by-pixel basis.

To perform FRET-based assays, the POSH polypeptide and the interacting protein of interest are both fluorescently labeled. Suitable fluorescent labels are, in view of this specification, well known in the art. Examples are provided below, but suitable fluorescent labels not specifically discussed are also available to those of skill in the art. Fluorescent labeling may be accomplished by expressing a polypeptide as a fusion protein with a fluorescent protein, for example fluorescent proteins isolated from jellyfish, corals and other coelenterates. Exemplary fluorescent proteins include the many variants of the green fluorescent protein (GFP) of *Aequoria victoria*. Variants may be brighter, dimmer, or have different excitation and/or emission spectra. Certain variants are altered such that they no longer appear green, and may appear blue, cyan, yellow or red (termed BFP, CFP, YFP and RFP, respectively). Fluorescent proteins may be stably attached to polypeptides through a variety of covalent and noncovalent linkages, including, for example, peptide bonds (eg. expression as a fusion protein), chemical cross-linking and biotin-streptavidin coupling. For examples of fluorescent proteins, see U.S. Pat. Nos. 5,625,048; 5,777,079; 6,066,476; 6,124,128; Prasher et al. (1992) *Gene,* 111:229-233; Heim et al. (1994) *Proc. Natl. Acad. Sci., USA,* 91:12501-04; Ward et al. (1982) *Photochem. Photobiol.,* 35:803-808; Levine et al. (1982) *Comp. Biochem. Physiol.,* 72B:77-85; Tersikh et al. (2000) *Science* 290: 1585-88.

Other exemplary fluorescent moieties well known in the art include derivatives of fluorescein, benzoxadioazole, coumarin, eosin, Lucifer Yellow, pyridyloxazole and rhodamine. These and many other exemplary fluorescent moieties may be found in the *Handbook of Fluorescent Probes and Research Chemicals* (2000, Molecular Probes, Inc.), along with methodologies for modifying polypeptides with such moieties. Exemplary proteins that fluoresce when combined with a fluorescent moiety include, yellow fluorescent protein from *Vibrio fischeri* (Baldwin et al. (1990) *Biochemistry* 29:5509-15), peridinin-chlorophyll a binding protein from the dinoflagellate *Symbiodinium* sp. (Morris et al. (1994) *Plant Molecular Biology* 24:673:77) and phycobiliproteins from marine cyanobacteria such as Synechococcus, e.g., phycoerythrin and phycocyanin (Wilbanlcs et al. (1993) *J. Biol. Chem.* 268:1226-35). These proteins require flavins, peridinin-chlorophyll a and various phycobilins, respectively, as fluorescent co-factors.

FRET-based assays may be used in cell-based assays and in cell-free assays. FRET-based assays are amenable to high-throughput screening methods including Fluorescence Activated Cell Sorting and fluorescent scanning of microtiter arrays.

In general, where the screening assay is a binding assay (whether protein-protein binding, agent-protein binding, etc.), one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin etc. For the specific binding members, the complementary member would normally be labeled with a molecule that provides for detection, in accordance with known procedures.

In further embodiments, the invention provides methods for identifying targets for therapeutic intervention. A polypeptide that interacts with POSH or participates in a POSH-mediated process (such as viral maturation) may be used to identify candidate therapeutics. Such targets may be identified by identifying proteins that associate with POSH (POSH-APs) by, for example, immuno-precipitation with an anti-POSH antibody, in silico analysis of high-throughput binding data, two-hybrid screens, and other protein-protein interaction assays described herein or otherwise known in the art in view of this disclosure. Agents that bind to such targets or disrupt protein-protein interactions thereof, or inhibit a biochemical activity thereof may be used in such an assay.

In particular, the yeast two-hybrid screen makes use of chimeric genes, which express hybrid proteins. To illustrate, a first hybrid gene comprises the coding sequence for a DNA-binding domain of a transcriptional activator can be fused in frame to the coding sequence for a "bait" protein, e.g., a POSH polypeptide of sufficient length to bind to a potential interacting protein. The second hybrid protein encodes a transcriptional activation domain fused in frame to a gene encoding a "fish" protein, e.g., a potential interacting protein of sufficient length to interact with the POSH polypeptide portion of the bait fusion protein. If the bait and fish proteins are able to interact, e.g., form a POSH complex, they bring into close proximity the two domains of the transcriptional activator. This proximity causes transcription of a reporter gene, which is operably linked to a transcriptional regulatory site responsive to the transcriptional activator, and expression of the reporter gene can be detected and used to score for the interaction of the bait and fish proteins.

Targets that have been identified by such approaches include HERPUD1. Other targets that may be identified by such approaches include: Vpu; Cbl-b; PKA; UNC84; MSTP028; GOCAP1; PTPN12; EIF3S3; SAR1; GOSR2; RALA; SIAH; SMIN1; SMN2; SYNE1; TTC3; VCY21P1;

SAM68; Gag-Pol; a GTPase a GTPase (eg. Rac, Rac1, Rho, Ras); an E2 enzyme, a culiin; a clathrin; AP-1; AP-2; an HSP70; an HSP90, Brcal, Bardl, Nef, PAKI, PAK2, PAK family, Vav, Cdc42, PI3K (e.g. p85 or p110), Nedd4, src (src family), Tsg101, VASP, RNB6, WASP, N-WASP, a Gag, particularly an HIV Gag (e.g. p160); and KIAA0674, Similar to Spred-2, as well as, in certain embodiments, proteins known to be associated with clathrin-coated vesicles, proteins involved in the protein sorting pathway and proteins involved in a Rac signaling pathway.

A variety of other reagents may be included in the screening assay. These include reagents like salts, neutral proteins, e.g. albumin, detergents, etc that are used to facilitate optimal protein-protein binding and/or reduce nonspecific or background interactions. Reagents that improve the efficiency of the assay, such as protease inhibitors, nuclease inhibitors, anti-microbial agents, etc. may be used. The mixture of components are added in any order that provides for the requisite binding. Incubations are performed at any suitable temperature, typically between 4° and 40° C. Incubation periods are selected for optimum activity, but may also be optimized to facilitate rapid high-throughput screening.

In certain embodiments, a test agent may be assessed for its ability to perturb the localization of a POSH polypeptide, e.g. preventing POSH localization to the nucleus and/or the Golgi network.

In applicant's previous application PCT/US2004/10582 filed on Apr. 5, 2004, herein incorporated by reference in its entirety, the discovery of novel associations between POSH proteins and HERPUD1 proteins, and related methods and compositions were described. In said application, novel associations among certain disease states, POSH nucleic acids and proteins, and HERPUD1 nucleic acids and proteins, were also disclosed.

By identifying proteins associated with POSH, and particularly human POSH, the present application provides a conceptual link between the POSH-APs and cellular processes and disorders associated with POSH-APs, and POSH itself. Accordingly, in certain embodiments of the disclosure, agents that modulate a POSH-AP, such as HERPUD1, may now be used to modulate POSH functions and disorders associated with POSH function, such as neurological disorders. Likewise, in certain embodiments of the disclosure, agents that modulate POSH may now be used to modulate POSH-AP, such as HERPUD1, functions and disorders associated with POSH-AP function, such as disorders associated with HERPUD1 function, including HERPUD1-associated neurological disorders. Additionally, test agents may be screened for an effect on HERPUD1 and then further tested for effect on a POSH-AP function or a disorder associated with POSH-AP function. In the PCT application mentioned above, it was disclosed that a POSH polypeptide interacts with one or more HERPUD1 polypeptides.

The term "amyloid polypeptide" is used to refer to any of the various polypeptides that are significant components of amyloid plaque as well as precursors thereof. The amyloid beta A4 precursor protein ("APP") gives rise to smaller proteins, such as the roughly 40 amino acid beta-amyloid proteins that form a major component of the amyloid plaque associated with Alzheimer's disease, Down's syndrome (in older patients) and certain hereditary cerebral hemorrhage amyloidoses. APP has several isoforms generated by alternative splicing of a 19-exon gene: exons 1-13, 13a, and 14-18 (Yoshikai et al., 1990). The predominant transcripts are APP695 (exons 1-6, 9-18, not 13a), APP751 (exons 1-7, 9-18, not 13a), and APP770 (exons 1-18, not 13a). All of these encode multidomain proteins with a single membrane-spanning region. They differ in that APP751 and APP770 contain exon 7, which encodes a serine protease inhibitor domain. APP695 is a predominant form in neuronal tissue, whereas APP751 is the predominant variant elsewhere. Beta-amyloid is derived from that part of the protein encoded by parts of exons 16 and 17. All of the isoforms of APP and any of the smaller proteins derived therefrom are included in the term "amyloid polypeptide", as well as any of the various naturally occurring variations thereof and any artificially produced variants that retain one or more functional properties of the naturally occurring protein or that are useful as a proxy for monitoring the production of APP or a protein derived therefrom. The subset of amyloid polypeptides that are APP or derived therefrom may be referred to specifically as "APP amyloid polypeptides". Yoshikai et al. Gene 87: 257-263, 1990.

A "POSH-associated protein" or "POSH-AP" refers to a protein capable of interacting with and/or binding to a POSH polypeptide. Generally, the POSH-AP may interact directly or indirectly with the POSH polypeptide. A preferred POSH-AP of the application is HERPUD1. Examples of HERPUD1 polypeptides are provided throughout.

As described, a POSH polypeptide interacts with the POSH-AP HERPUD1, a "homocysteine-inducible, endoplasmic reticulum stress-inducible, ubiquitin-like domain member 1" protein. This interaction was identified by Applicants as described herein below in a yeast two-hybrid assay. HERPUD1 is synonymous with Herp or HERP, and the terms are used interchangeably herein. HERPUD1 is involved in the maturation of an envelope virus, such as HIV.

Certain HERPUD1 polypeptides are involved in JNK-mediated apoptosis, particularly in vascular endothelial cells, including cells that are exposed to high levels of homocysteine. Certain HERPUD1 polypeptides are involved in the Unfolded Protein Response, a cellular response to the presence of unfolded proteins in the endoplasmic reticulum. Certain HERPUD1 polypeptides are involved in the regulation of sterol biosynthesis. Accordingly, certain POSH polypeptides are involved in the Unfolded Protein Response and sterol biosynthesis.

In other aspects, certain HERPUD1 polypeptides enhance presenilin-mediated amyloid beta-protein generation. For example, HERPUD1 polypeptides, when overexpressed in cells, increase the level of amyloid beta generation, and it has been observed that HERPUD1 polypeptides interact with the presenilin proteins, presenilin-1 (PS-1) and presenilin-2 (PS-2) (See Sai, X. et al (2002) J. Biol. Chem. 277:12915-12920). Accordingly, in certain aspects, POSH polypeptides may modulate the level of amyloid beta generation. Additionally, POSH polypeptides may interact with presenilin 1 and presenilin 2. Therefore, it is believed certain POSH polypeptides modulate presenilin-mediated amyloid beta generation. The accumulation of amyloid beta is one hallmark of Alzheimer's disease. Accordingly, these POSH polypeptides may be involved in the pathogenesis of Alzheimer's disease. At sites such as late intracellular compartment sites including the trans-Golgi network, certain mutant presenilin-2 polypeptides up-regulate production of amyloid beta peptides ending at position 42 (Aβ42). (See Iwata, H. et al (2001) J. Biol. Chem. 276: 21678-21685). Accordingly, POSH polypeptides may regulate production of Aβ42 through mutant presenilin-2 at late intracellular compartment sites including the trans-Golgi network. Furthermore, elevated homocysteine levels have been found to be a risk factor associated with Alzheimer's disease and cerebral vascular disease. Some risk factors, such as elevated plasma homocysteine levels, may accelerate or increase the severity of several central nervous system (CNS) disorders. Elevated levels of plasma homocysteine were found in young male patients with schizophrenia suggesting that elevated homocysteine levels could be related to the pathophysiology of aspects of schizophrenia (Levine, J. et al (2002) Am. J. Psychiatry 159:1790-2). Epidemiological and experimental studies have linked increased homocysteine levels with neurodegenerative conditions, including Alzheimer's disease, Parkinson's disease, depression, and stroke (reviewed in Mattson, M P and Shea, T B (2003) Trends Neurosci 26:137-46).

Accordingly, certain POSH polypeptides may be involved in neurological disorders. Neurological disorders include disorders associated with increased levels of plasma homocysteine, increased levels of amyloid beta production, or aberrant presenilin activity. Neurological disorders include CNS disorders, such as Alzheimer's disease, cerebral vascular disease, and schizophrenia.

Certain POSH polypeptides may be involved in cardiovascular diseases, such as thromboembolic vascular disease, and particularly the disease characteristics associated with hyperhomocysteinemia. See, for example, Kokame et al. 2000 J. Biol. Chem. 275:32846-53; Zhang et al. 2001 Biochem Biophys Res Commun 289:718-24.

As described herein, POSH and HERPUD1 are involved in viral maturation, including the production, post-translational processing, assembly and/or release of proteins in a viral particle. Accordingly, viral infections may be ameliorated by inhibiting an activity of HERPUD1 or POSH (e.g., inhibition of ubiquitin ligase activity). In preferred embodiments, the virus is a retroid virus, an RNA virus or an envelope virus, including HIV, Ebola, HBV, HCV, HTLV, West Nile Virus (WNV) or Moloney Murine Leukemia Virus (MMuLV). Additional viral species are described in greater detail below. In certain instances, a decrease of a POSH function is lethal to cells infected with a virus that employs POSH in release of viral particles.

In certain aspects, the application describes an HPOSH interaction with Rac, a small GTPase and the POSH associated kinases MLK, MKK and JNK. Rho, Rac and Cdc42 operate together to regulate organization of the actin cytoskeleton and the MLK-MKK-JNK MAP kinase pathway (referred to herein as the "JNK pathway" or "Rac-JNK pathway" (Xu et al., 2003, EMBO J. 2: 252-61). Ectopic expression of mouse POSH ("mPOSH") activates the JNK pathway and causes nuclear localization of NF-κB. Overexpression of MPOSH in fibroblasts stimulates apoptosis. (Tapon et al. (1998) EMBO J. 17:1395-404). In Drosophila, POSH may interact with, or otherwise influence the signaling of, another GTPase, Ras. (Schnorr et al. (2001) Genetics 159: 609-22). The JNK pathway and NF-κB regulate a variety of key genes involved in, for example, immune responses, inflammation, cell proliferation and apoptosis. For example, NF-κB regulates the production of interleukin 1, interleukin 8, tumor necrosis factor and many cell adhesion molecules. NF-κB has both pro-apoptotic and anti-apoptotic roles in the cell (e.g., in FAS-induced cell death and TNF-alpha signaling, respectively). NF-κB is negatively regulated, in part, by the inhibitor proteins IκBα and IκBβ (collectively termed "IκB"). Phosphorylation of IκB permits activation and nuclear localization, of NF-κB. Phosphorylation of IκB triggers its degradation by the ubiquitin system.

In an additional embodiment, a POSH polypeptide promotes nuclear localization of NF-κB. By downregulating POSH, apoptosis may be diminished in certain cells, and this will generally be desirable in conditions characterized by excessive cell death, such as myocardial infarction, stroke, degenerative diseases of muscle and nerve (particularly Alzheimer's disease), and for organ preservation prior to transplant.

In a further embodiment, a POSH polypeptide associates with a vesicular trafficking complex, such as a clathrin- or coatomer-containing complex, and particularly a trafficking complex that localizes to the nucleus and/or Golgi apparatus.

As described in WO03/095971A2 and W003/078601A2, both herein incorporated by reference in their entirety, POSH polypeptides function as E3 enzymes in the ubiquitination system. Accordingly, downregulation or upregulation of POSH ubiquitin ligase activity can be used to manipulate biological processes that are affected by protein ubiquitination. Modulation of POSH ubiquitin ligase activity may be used to affect POSH and related biological processes, and likewise, modulation of POSH may be used to affect POSH ubiquitin ligase activity and related processes. Downregulation or upregulation may be achieved at any stage of POSH formation and regulation, including transcriptional, translational or post-translational regulation. For example, POSH transcript levels may be decreased by RNAi targeted at a POSH gene sequence. As another example, POSH ubiquitin ligase activity may be inhibited by contacting POSH with an antibody that binds to and interferes with a POSH RING domain or a domain of POSH that mediates interaction with a target protein (a protein that is ubiquitinated at least in part because of POSH activity).

As a further example, in a most preferred embodiment, small molecule inhibitors of POSH ubiquitin ligase activity are provided herein, consisting of compounds of the general formula I herein, more preferably, compounds of the formula Ia.

As another example, POSH activity may be increased by causing increased expression of POSH or an active portion thereof. POSH, and POSH-APs that modulate POSH ubiquitin ligase activity may participate in biological processes including, for example, one or more of the various stages of a viral lifecycle, such as viral entry into a cell, production of viral proteins, assembly of viral proteins and release of viral particles from the cell. POSH may participate in diseases characterized by the accumulation of ubiquitinated proteins, such as dementias (e.g., Alzheimer's and Pick's), inclusion body myositis and myopathies, polyglucosan body myopathy, and certain forms of amyotrophic lateral sclerosis. POSH may participate in diseases characterized by excessive or inappropriate ubiquitination and/or protein degradation.

In certain aspects, the application provides methods and compositions for treatment of POSH-associated diseases (disorders), including neurological disorders. In certain aspects, the application provides methods and compositions for treatment of POSH-AP-associated diseases (disorders), such as HERPUD1-associated disorders, including neurological and viral disorders, as well as neurological disorders associated with unwanted apoptosis, including, for example a variety of neurodegenerative disorders, such as Alzheimer's disease.

Preferred therapeutics of the application for the treatment of a neurological disorder can function by disrupting the biological activity of a POSH polypeptide or POSH complex associated with a neurological disorder. Certain therapeutics of the application function by disrupting the activity of POSH by inhibiting the ubiquitin ligase activity of a POSH polypeptide, such as, for example, by inhibiting the POSH-mediated ubiquitination of HERPUD1.

In certain embodiments, the application relates to methods of treating or preventing neurological disorders. In certain aspects, the invention provides methods and compositions for the identification of compositions that interfere with the function of a POSH or a POSH-AP, such as HERPUD1, which function may relate to aberrant protein processing associated with a neurodegenerative disorder, such as for example, the processing of amyloid beta precursor protein associated with Alzheimer's disease.

Neurological disorders include disorders associated with increased levels of amyloid polypeptides, such as for example, Alzheimer's disease. Neurological disorders also include Parkinson's disease, Huntington's disease, schizophrenia, Pick's disease, Niemann-Pick's disease, prion-associated diseases (e.g., Mad Cow disease), depression, and schizophrenia.

In certain aspects, the present application provides assays for identifying therapeutic agents, which either interfere with or promote POSH or POSH-AP function. In certain aspects, the present application also provides assays for identifying therapeutic agents, which either interfere with or promote the complex formation between a POSH polypeptide and a POSH-AP polypeptide. In preferred embodiments of the application, the application provides assays for identifying therapeutic agents, which either interfere with or promote POSH or POSH-AP (e.g., HERPUD1) function. In certain preferred aspects, the present application also provides assays for identifying therapeutic agents, which either interfere with or promote the complex formation between a POSH polypeptide and a HERPUD1 polypeptide.

In preferred embodiments, the application provides agents for the treatment of neurological disorders. In certain embodiments, the application provides assays to identify, optimize or otherwise assess agents that disrupt the interaction between a POSH polypeptide and a HERPUD1 polypeptide.

In certain preferred embodiments, an agent of the application is one that disrupts a complex comprising POSH and HERPUD1. Optionally, the agent is one that disrupts a complex comprising POSH and HERPUD1 without inhibiting POSH ubiquitin ligase activity, such as POSH auto-ubiquitination. In certain embodiments, an agent of the application is one that inhibits POSH-mediated ubiquitination of HERPUD1, optionally without inhibiting POSH auto-ubiquitination.

In certain embodiments, agents of the application are useful in treating or preventing neurological disorders. Treatment or prevention of a neurological disorder includes inhibition of the progression of a neurological disorder. In certain embodiments, an agent useful in the treatment or prevention of a neurological disorder or an agent that inhibits the progression of a neurological disorder interferes with the ubiquitin ligase catalytic activity of POSH (e.g., POSH ubiquitination of a target protein such as HERPUD1).

In other embodiments, agents disclosed herein inhibit or promote POSH and POSH-AP, such as HERPUD1, mediated cellular processes such as protein processing in the secretory pathway, for example, processing of amyloid polypeptides.

In certain embodiments, agents of the application are antiviral agents, optionally interfering with viral maturation, and preferably where the virus is an envelope virus, and optionally a retroid virus or an RNA virus. In certain embodiments, an antiviral agent interferes with the interaction between POSH and a POSH-AP polypeptide, for example an antiviral agent may disrupt an interaction between a POSH polypeptide and a HERPUD1 polypeptide.

In yet additional embodiments, agents of the application interfere with the signaling of a GTPase, such as Rac or Ras, optionally disrupting the interaction between a POSH polypeptide and a Rac protein.

In certain embodiments, agents of the application interfere with the trafficking of a protein through the secretory pathway.

An additional POSH-AP may be added to a POSH ubiquitination assay to assess the effect of the POSH-AP (e.g., HERPUD1) on POSH-mediated ubiquitination and/or to assess whether the POSH-AP (e.g., HERPUD1) is a target for POSH-mediated ubiquitination.

The present application discloses reconstituted protein preparations including a POSH polypeptide and one or more interacting polypeptides.

Additional bioassays for assessing POSH and POSH-AP activities may include assays to detect the improper processing of a protein that is associated with a neurological disorder. One assay that may be used is an assay to detect the presence, including an increase or a decrease in the amount, of a protein associated with a neurological disorder. For example, the use of RNAi may be employed to knockdown the expression of a POSH or POSH-AP polypeptide, such as HERPUD1, in cells (e.g., CHO cells, COS cells, or HeLa cells). The production of a secreted protein such as for example, amyloid beta, in the cell culture media, can then be assessed and compared to production of the secreted protein from control cells, which may be cells in which the POSH or POSH-AP activity (e.g., HERPUD1 activity) has not been inhibited. In some instances, a label may be incorporated into a secreted protein and the presence of the labeled secreted protein detected in the cell culture media. Proteins secreted from any cell type may be assessed, including for example, neural cells.

Bioassays for POSH or POSH-AP activities may include assays to detect the improper processing of a protein that is associated with a degenerative neurological disorder, such as Alzheimer's disease. One assay that may be used to detect POSH or POSH-AP activity associated with a neurological disorder is an assay to detect the presence, including an increase or a decrease in the amount, of amyloid polypeptides. One such assay includes assessing the effect of modulation of a POSH or POSH-AP on the production of amyloid polypeptides. For example, the use of RNAi may be employed to knockdown the expression of a POSH polypeptide or a POSH-AP (e.g., HERPUD1) in cells (e.g., HeLa cells) that express proteins associated with gamma-secretase activity, such as presenilin (e.g., presenilin 1), which enzymatic activity is involved in the proteolytic cleavage of amyloid beta precursor protein ("APP") to yield amyloid beta peptide. Optionally, other proteins associated with gamma-secretase may be expressed, such as, for example, nicastrin, Aph-1, and Pen-2. The production of amyloid polypeptides, e.g., in the cell culture media, can then be assessed and compared to the production of amyloid polypeptides from cells in which the POSH or POSH-AP activity has not been modulated. In certain embodiments, the levels of APP can be assessed and compared to the levels of APP in which POSH or POSH-AP activity has not been modulated.

Additional assays for POSH or POSH-AP activities include in vitro gamma-secretase assays, which may be employed to assess the effect of modulation of a POSH or POSH-AP (e.g., knockdown of POSH expression or knockdown of HERPUD1 expression by RNAi) on gamma-secretase activity in comparison to the gamma-secretase activity in cells in which the POSH or POSH-AP activity has not been modulated. For example, gamma-secretase activity in the cells in which POSH or POSH-AP activity has been modulated (e.g., by RNAi) may be monitored by incubating solubilized gamma-secretase from the cells with tagged (e.g., a FLAG epitope) APP-based substrate and detecting the substrates and cleavage products (e.g., amyloid beta peptide) by immunoblotting and comparing the results to those of control cells (cells in which the POSH or POSH-AP activity has not been modulated) manipulated in the same manner. The effect of modulation of an activity of a POSH polypeptide or a POSH-AP on amyloid polypeptide production may be assessed in any cell capable of producing amyloid polypeptides.

The effect of an agent that modulates the activity of POSH or a POSH-AP, such as HERPUD1, may be evaluated for effects on mouse models of various neurological disorders. For example, mouse models of Alzheimer's disease have been described. See, for example, U.S. Pat. No. 5,612,486 for "Transgenic Animals Harboring APP Allele Having Swedish Mutation", U.S. Pat. No. 5,850,003 (the '003 patent) for "Transgenic Rodents Harboring APP Allele Having Swedish Mutation," and U.S. Pat. No. 5,455,169 entitled "Nucleic Acids for Diagnosing and Modeling Alzheimer's Disease". Mouse models of Alzheimer's disease tend to produce elevated levels of beta-amyloid protein in the brain, and the increase or decrease of such protein in response to treatment with a test agent may be detected. In some instances, it may also be desirable to assess the effects of a test agent on cognitive or behavioral characteristics of a mouse model for Alzheimer's disease, as well as mouse models for other neurological disorders.

In a further embodiment, transcript levels may be measured in cells having higher or lower levels of POSH or POSH-AP activity, such as HERPUD1 activity, in order to identify genes that are regulated by POSH or POSH-APs. Promoter regions for such genes (or larger portions of such genes) may be operatively linked to a reporter gene and used in a reporter gene-based assay to detect agents that enhance or diminish POSH- or POSH-AP-regulated gene expression. Transcript levels may be determined in any way known in the art, such as, for example, Northern blotting, RT-PCR, microarray, etc. Increased POSH activity may be achieved, for example, by introducing a strong POSH expression vector. Decreased POSH activity may be achieved, for example, by RNAi, antisense, ribozyme, gene knockout, etc.

In certain embodiments, a test agent may be assessed for antiviral activity by assessing effects on an activity (function) of a POSH-AP, such as, for example, POSH. Activity (function) may be affected by an agent that acts at one or more of the transcriptional, translational or post-translational stages. For example, an siRNA directed to a POSH-AP encoding gene will decrease activity, as will a small molecule that interferes with a catalytic activity of a POSH-AP. In certain embodiments, the agent inhibits the activity of one or more POSH polypeptides.

The invention now being generally described, it will be more readily understood by reference to the following examples, which are included merely for purposes of illustration of certain aspects and embodiments of the present invention, and are not intended to limit the invention.

EXAMPLES

II Biological Section

Example 1

Selection of POSH Inhibitors by HTS TR-FRET Assay

In order to test compounds as inhibitors of POSH, a ubiquitin protein ligase (E3) containing a RING domain that mediates its own ubiquitination in a RING finger-dependent manner in the presence of E1 and E2, a HTS (high-throughput screening) homogeneous TR-FRET (Time-Resolved Fluorescence Resonance Energy Transfer) assay was conducted to monitor POSH autoubiquitination.

The assay employs an ubiquitin-activating enzyme (E1) and an ubiquitin-conjugating enzyme (E2), a fused GST-RING subunit of POSH protein and two fluorophore-conjugated detection reagents, namely anti-GSTXL665 and europium cryptate-labeled ubiquitin. This homogeneous assay is based on FRET between a $Eu^{3+}$ cryptate donor and a second fluorescent label (acceptor), allophycocyanin. Allophycocyanin, a 105 kDa phycobiliprotein, is crosslinked to ensure its stability. This chemically modified fluorophore, known as XL665, displays a set of photophysical properties matching those of $Eu^{3+}$ cryptates.

The ubiquitination of POSH by ubiquitin cryptate and binding of the anti-GST tagged XL665 brings the fluorophores into close proximity allowing FRET reaction to occur. The compounds that do not allow the FRET reaction to occur, are considered as inhibitors.

Self-ubiquitination of hPOSH was determined by homogenous time-resolved fluorescence resonance energy transfer assay (TR-FRET). The conjugation of ubiquitin cryptate to GST tagged hPOSH and the binding of anti-GST tagged XL665 bring the two fluorophores into close proximity, which allows the FRET reaction to occur. To measure hPOSH ubiquitination activity, GST tagged hPOSH (60 nM) was incubated in reaction buffer (40 mM Hepes-NaOH, pH 7.5, 1 mM DTT, 2 mM ATP, 5 mM MgCl2, (with recombinant E1 (8 nM), UbCH5c (500 nM), and ubiquitin-cryptate (15 nM) (CIS Bio International) for 30 minutes at 37° C. Reactions were stopped with 0.5M EDTA. Anti-GST-XL665 (CIS bio International) (50 nM) was then added to the reaction mixture for a further 45 minutes incubation at room temperature. Emission at 620 nm and 665 nM was obtained after excitation at 380 nm in a fluorescence reader (RUBYstar, BMG Labtechnologies). The generation of hPOSH-ubiquitin-cryptate adducts was then determined by calculating the fluorescence resonance energy transfer (FRET=(F)) using the following formula:

$$F=[(S665/S620-B665/B620)/(C665/C620-B665/B620)]$$

where: S=actual fluorescence, B=Fluorescence obtained in parallel incubation without cbl-b, C=Fluorescence obtained in reaction without added compounds.

In the first step, for evaluation and identification of POSH specific inhibitors, candidate compounds were added to the assay at various concentrations. The compounds that have blocked POSH autoubiquitination at a concentration of 10 μM (in DMSO solution), with inhibition rate of 90% or above, were designated as good inhibitor. The compounds (concentration of 1 μM) were again tested in an assay in the presence of both E1 and E2, but in the absence of the fused GST-RING subunit of POSH, and the compounds that inhibited E1+E2 ubiquitination above 70%, were removed. The compounds identified as good inhibitors of POSH autoubiquitination were subjected to optimization.

Compound 1 presented an IC50 of 2 μM in this in vitro assay.

Example 2

Assay for Virus Release—Compound 1 Inhibits Release of HIV-1 p24

The POSH inhibitor Compound 1 was tested for its efficiency of viral budding and GAG expression and processing in treated and untreated Jurkat cells. The concentration of extracellular GAG p24 was used as an indication of viral budding.

Jurkat cells were incubated with Compound 1 (5 µM) for either 1 or 3 days. The next day, cells were transfected with the plasmid pNLenv1 (2 µg/ml). Virus-like particle (VLP) release was determined one day after transfection as follows: the culture medium of virus-expressing cells was collected and centrifuged at 500×g for 10 minutes. The resulting supernatant was passed through a 0.45 µm-pore filter and the filtrate was centrifuged at 14,000×g for 2 hours at 4° C. The corresponding cells were washed three times with phosphate-buffered saline (PBS) and then solubilized by incubation on ice for 15 minutes in lysis buffer containing the following components: 50 nM Hepes-NaOH, (pH 7.5), 150 mM NaCl, 1.5 mM $MgCl_2$, 0.3% NP-40, 0.5% sodium deoxycholate, 1 mM EDTA, 1 mM EGTA and 1:200 dilution of protease inhibitor cocktail (EMD Biosciences, Inc.). The cell detergent extract was then centrifuged for 15 minutes at 14,000×g at 4° C. The VLP sample and a sample of the cleared cell extract, were resolved on a 12.5% SDS-polyacrylamide gel, then transferred onto nitrocellulose paper and subjected to immunoblot analysis with rabbit anti-CA antibodies (Seramun Diagnostica, GmbH), a secondary anti-rabbit horseradish peroxidase (HRP)-conjugated antibody and a HRP substrate. Enhanced Chemi-Luminescence (ECL) (Amersham Biosciences, Corp.) was then detected by fluorescence imaging (Typhoon Instrument, Amersham Biosciences, Corp.). Compound 1 presented an $IC_{50}$ of 48 µM in the virus release assay.

Example 3

POSH Protein-Protein Interactions by Yeast Two-Hybrid Assay

POSH-associated proteins were identified by using a yeast two-hybrid assay.

Procedure: Bait plasmid (GAL4-BD) was transformed into yeast strain AH109 (Clontech) and transformants were selected on defined media lacking tryptophan. Yeast strain Y187 containing pre-transformed Hela cDNA prey (GAL4-AD) library (Clontech) was mated according to the Clontech protocol with bait containing yeast and plated on defined media lacking tryptophan, leucine, histidine and containing 2 mM 3 amino triazol. Colonies that grew on the selective media were tested for beta-galactosidase activity and positive clones were further characterized. Prey clones were identified by amplifying cDNA insert and sequencing using vector derived primers.

Bait:
Plasmid vector: pGBK-T7 (Clontech)
Plasmid name: pPL269-pGBK-T7 GAL4 POSHdR
Protein sequence: Corresponds to aa 53-888 of POSH (RING domain deleted; SEQ ID NO: 1)
Library screened: Hela pretransformed library (Clontech).
The POSH-AP, HERPUD1 (Hs. 146393), was identified by yeast two-hybrid Examples of nucleic acid and amino acid sequences of HERPUD1 are provided below.

SEQ ID NO: 2—Human HERPUD1 cDNA sequence—var1 (public gi: 16507801)
SEQ ID NO: 3—Human HERPUD1 cDNA sequence—var2 (public gi: 10441910)
SEQ ID NO: 4—Human HERPUD1 cDNA sequence—var3 (public gi: 3005722)
SEQ ID NO: 5—Human HERPUD1 cDNA sequence—var4 (public gi: 21619176)
SEQ ID NO: 6—Human HERPUD1 cDNA sequence—var5 (public gi: 14249882)
SEQ ID NO: 7—Human HERPUD1 cDNA sequence—var6 (public gi: 12652674)
SEQ ID NO: 8—Human HERPUD1 cDNA sequence—var7 (public gi: 9711684)
SEQ ID NO: 9—Human HERPUD1 cDNA sequence—var8 (public gi: 3005718)
SEQ ID NO: 10—Human HERPUD1 cDNA sequence—var9 (public gi: 285960)
SEQ ID NO: 11—Human HERPUD1 cDNA sequence—var10 (public gi: 7661869)
SEQ ID NO: 12—Human HERPUD1 Protein sequence—var1 (public gi: 16507802)
SEQ ID NO: 13—Human HERPUD1 Protein sequence—var2 (public gi: 10441911)
SEQ ID NO: 14—Human HERPUD1 Protein sequence—var3 (public gi: 3005723)
SEQ ID NO: 15—Human HERPUD1 Protein sequence—var4 (public gi: 7661870)
SEQ ID NO: 16—Rat HERPUD1 cDNA sequence (public gi: 16758961)
SEQ ID NO: 17—Rat HERPUD1 Protein sequence (public gi: 16758962)
SEQ ID NO: 18—Mouse HERPUD1 cDNA sequence (public gi: 11612514)
SEQ ID NO: 19—Mouse HERPUD1 Protein sequence (public gi: 11612515)

Example 4

HERPUD1 Depletion by siRNA Reduces HIV Maturation

HeLa SS6 cells were transfeted with siRNA directed against HERPUD1 and with a plasmid encoding HIV proviral genome (pNLenv-1). Twenty-four hours post-HIV transfection, virus-like particles (VLP) secreted into the medium were isolated and reverse transcriptase activity was determined. HIV release of active RT is an indication for a release of processed and mature virus. When the levels of HERPUD1 were reduced, RT activity was inhibited by 80%, demonstrating the importance of HERPUD1 in HIV-maturation.

Experimental Outline

Cell Culture and Transfection

HeLa SS6 were kindly provided by Dr. Thomas Tuschl (the laboratory of RNA Molecular Biology, Rockefeller University, New York, N.Y.). Cells were grown in Dulbecco's modified Eagle's medium (DMEM) supplemented with 10% heat-inactivated fetal calf serum and 100 U/ml penicillin and 100 µg/ml streptomycin. For transfections, HeLa SS6 cells were grown to 50% confluency in DMEM containing 10% FCS without antibiotics. Cells were then transfected with the relevant double-stranded siRNA (50-100 nM) (HERPUD1: 5'-GGGAAGUUCUUCGGAACCUdTdT-3' (SEQ ID NO: 20) and 5'-dTdTCCCUUCAAGAAGCCUUGGA-5' (SEQ ID NO: 21) using lipofectamin 2000 (Invitrogen, Paisley, UK). A day following the initial transfection cells were split 1:3 in complete medium and co-transfected 24 hours later with HIV-1NLenv1 (2 µg per 6-well) (Schubert et al., J. Virol. 72:2280-88 (1998)) and a second portion of double-stranded siRNA.

Assay for Virus Release

Virus and virus-like particle (VLP) release was determined one day after transfection with the proviral DNA as previously described (Adachi et al., J. Virol. 59: 284-91 (1986); Fukumori et al., Vpr. Microbes Infect. 2: 1011-17 (2000); Lenardo et al., J. Virol. 76: 5082-93 (2002)). The culture medium of virus-expressing cells was collected and centrifuged at 500×g for 10 minutes. The resulting supernatant was passed through a 0.45 µm-pore filter and the filtrate was centrifuged at 14,000×g for 2 hours at 4° C. The resulting supernatant was removed and the viral-pellet was re-suspended in SDS-PAGE sample buffer. The corresponding cells were washed three times with phosphate-buffered saline (PBS) and then solubilized by incubation on ice for 15 minutes in lysis buffer containing the following components: 50 mM HEPES-NaOH, (pH 7.5), 150 mM NaCl, 1.5 mM $MgCl_2$, 0.5% NP-40, 0.5% sodium deoxycholate, 1 mM EDTA, 1 mM EGTA and 1:200 dilution of protease inhibitor cocktail (Calbiochem, La Jolla, Calif.). The cell detergent extract was then centrifuged for 15 minutes at 14,000×g at 4° C. The VLP sample and a sample of the cleared extract (normally 1:10 of the initial sample) were resolved on a 12.5% SDS-polyacrylamide gel, then transferred onto nitrocellulose paper and subjected to immunoblot analysis with rabbit anti-CA antibodies. The CA was detected either after incubation with a secondary anti-rabbit horseradish peroxidase-conjugated antibody and detected by Enhanced Chemi-Luminescence (ECL) (Amersham Pharmacia) or after incubation with a secondary anti-rabbit antibody conjugated to Cy5 (Jackson Laboratories, West Grove, Pa.) and detected by fluorescence imaging (Typhoon instrument, Molecular Dynamics, Sunnyvale, Calif.). The Pr55 and CA were then quantified by densitometry and the amount of released VLP was then determined by calculating the ratio between VLP-associated CA and intracellular CA and Pr55 as previously described (Schubert et al., J. Virol. 72:2280-88 (1998)).

Analysis of Reverse Transcriptase Activity in Supernatants

RT activity was determined in pelleted VLP (see above) by using an RT assay kit (Roche, Germany; Cat. No. 1468120). Briefly, VLP pellets, were resuspended in 40 µl RT assay lysis buffer and incubated at room temperature for 30 minutes. At the end of incubation 20 µl RT assay reaction mix was added to each sample and incubation continued at 37° C. overnight. Samples (60 µl) were than transferred to MTP strip wells and incubated at 37° C. for 1 hour. Wells were washed five times with wash buffer and DIG-POD added for a one-hour incubation at 37° C. At the end of incubation wells were washed five times with wash buffer and ABST substrate solution was added and incubated until color developed. The absorbance was read in an ELISA reader at 405 nm (reference wavelength 492 nm). The resulting signal intensity is directly proportional to RT activity; RT concentration was determined by plotting against a known amount of RT enzyme included in separate wells of the reaction.

Example 5

Amyloid Precursor Protein Levels are Reduced in Cells that have Reduced Levels of POSH HeLa SS6 cells that express reduced levels of POSH (H153) and control cells expressing scrambled RNAi (H187) were transfected with a plasmid expressing amyloid precursor protein (APP) and presenilin 1 (PS1). Cells were metabolic labeled and protein extracts were immunoprecipitated with anti-amyloid beta specific antibody, which recognize an epitope common to APP, C199 and Aβpolypeptides. A labeled protein was specifically precipitated by the antibody in H187-transfected cells (not shown). However, this polypeptide was not recognized in H153 cells (not shown) indicating that APP steady state levels are reduced in H153 and may be rapidly degraded in these cells.

Methlods

Cloning of pIRES-APP-PS1

Cloning was performed in two steps: Presenilin 1 (PS1) was first cloned from human brain library into pIREs (pIREs-PS1). Then APP-695 was obtained from amplifying two image clones (3639599 and 5582406) and mixing their PCR products in an additional PCR reaction to yield full-length APP695 that was further ligated into pIREs-PS1 to generate pIREs-APP-PS1.

Transfection, Metabolic Labeling and Immunoisolation of Amyloid Beta (Aβ)

Hela SS6 cells expressing POSH-specific RNAi or scrambled RNAi (H153 and H187, respectively) were transfected with pIREs-APP-PS1 (24 µg) using lipofectamin 2000 reagent (Invitrogen, LTD). Twenty-four hours post-transfection, cells were metabolic labeled with 1 mCi of $^{35}$S-methionine at 37° C. for an additional twenty-four hours. Media was collected from cells and spun at 3000 rpm for 10 min to pellet cell debris. Protease inhibitors and 2 mM 1, 10-phenanthroline were added to the cleared cell media. Cells were lysed in lysis buffer (50 mM Tris-HCl, pH 7.8, 150 mM sodium chloride, 1 mM EDTA, 0.5% NP-40, 0.5% sodium deoxycholate and protease inhibitors). Cell media and lysate were immunoprecipitated with anti-Aβ(1-17) antibody (6E10) (Chemicon) or a non-relevant (NR) antibody. Precipitated proteins were separated on 16% Tris-Tricine gel. Gel was dried and bands detected by phosphoimager (Typhoon Instrument, Amersham Biosciences, Corp.).

Example 6

Cytoprotection Assay: Protection Conferred by Compounds 1, 2 and 5 on Cells Infected by HIV-1 and HIV-2

For the HIV cytoprotection assay, CEM-SS cells were used and the viruses HIV-1IIIb, HIV-1RF, or HIV-2ROD.

Briefly, virus and cells were mixed in the presence of a test compounds and incubated for 6 days. The virus was pre-titered such that control wells exhibited 70 to 95% loss of cell viability due to virus replication. Therefore, antiviral effect or cytoprotection was observed when the compounds prevented virus replication. Each assay plate contained the following controls: cell control wells (cells only), virus control wells (cells plus virus), compound toxicity control wells (cells plus compound only), compound calorimetric control wells (compound only), as well as the experimental wells (compound plus cells plus virus). Cytoprotection and compound cytotoxicity were assessed by MTS (CellTiter® 96 Reagent, Promega, Madison Wis.) dye reduction, and the IC50 (concentration inhibiting virus replication by 50%), TC50 (concentration resulting in 50% cell death) and a calculated TI (therapeutic index TC50/IC50) were obtained. Each assay included the HIV reverse transcriptase inhibitor AZT as a positive control.

The IC50, TC50 and TI data obtained for cytoprotection by Compounds 1, 2 and 5 against infection with HIV-1IIIB are depicted in Table 1, and the antiviral activity and compound cytotoxicity of Compound 1 are shown FIG. 1. It is to be noted that Compound 5 was far more effective as anti-HIV-1IIIB agent compared to Compounds 1 and 2.

Figure 2:
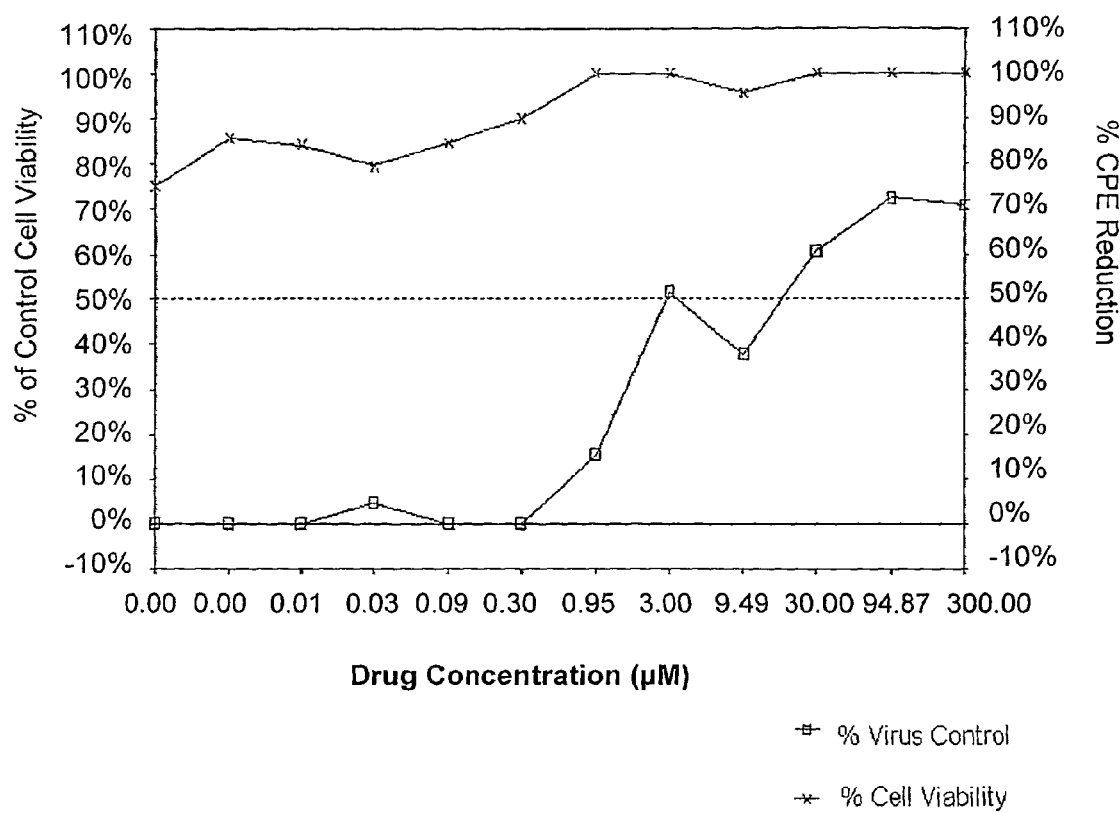
FIG. 2 is a graph showing the antiviral effect of Compound 5 on CEM-SS cells infected with HIV-1IIIB virus, and the cytotoxic effect of Compound 5 on uninfected CEM-SS cells.
Figure 3:
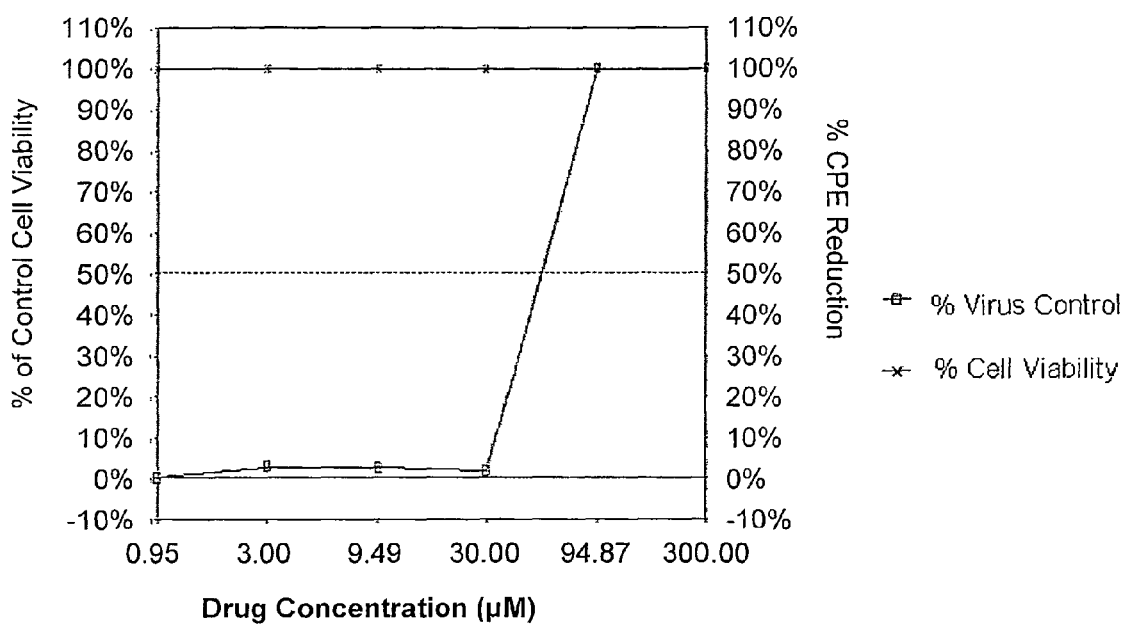
FIG. 3 is a graph showing the antiviral effect of Compound 1 on CEM-SS cells infected with HIV-2ROD virus, and its cytotoxic effect on uninfected CEM-SS cells.
Figure 4:
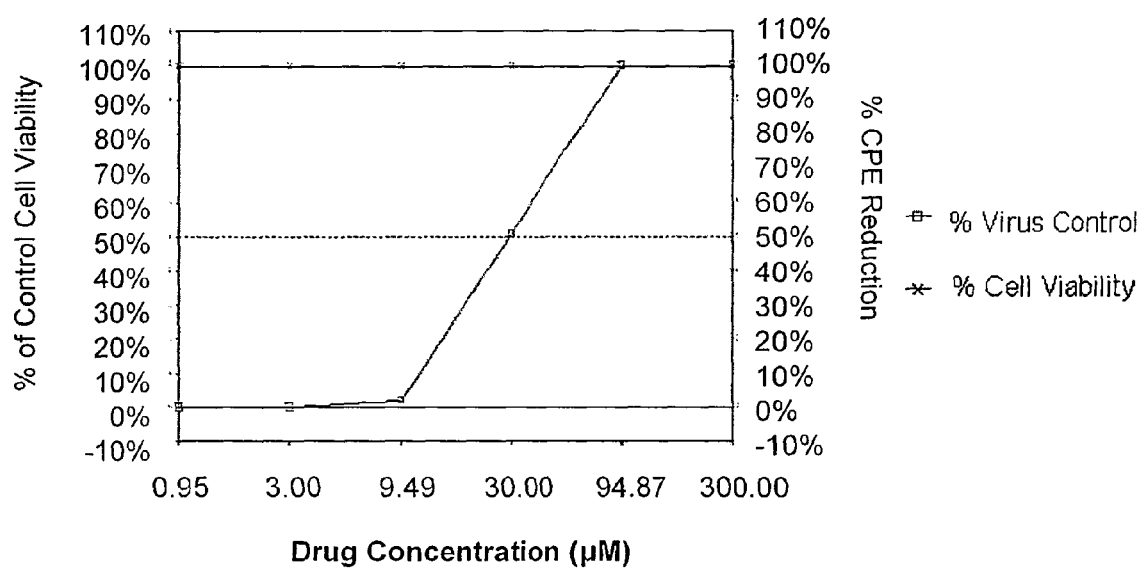
FIG. 4 is a graph showing the antiviral effect of Compound 2 on CEM-SS cells infected with HIV-2ROD virus, and the cytotoxic effect of Compound 2 on uninfected CEM-SS cells.

The cytoprotection assay data for both Compound 1 and Compound 2 against infection with HIV-2ROD are depicted in Table 2, and the antiviral activity and compound cytotoxicity are presented in FIGS. 2 and 3.

TABLE 1

Protection by Compounds 1 and 2 against HIV-1$_{IIIB}$ CEM-SS cells

| Compound | IC$_{50}$ | TC$_{50}$ | Antiviral Index (TI) |
|---|---|---|---|
| 1 | 48 μM | >100 μM | >2.07 |
| 2 | 3.99 μM | 114 μM | 28.5 |
| 5 | 2.85 μM | >300 μM | >105 |

TABLE 2

Protection of Compounds 1 and 2 against HIV-2$_{ROD}$ in CEM-SS cells

| Compound | IC$_{50}$ | TC$_{50}$ | Antiviral Index (TI) |
|---|---|---|---|
| 1 | 52.8 μM | >300 μM | >5.68 |
| 2 | 29.5 μM | >300 μM | >10.2 |

III Chemical Section

Example 7

Synthesis of Compound 1

The synthesis of Compound 1, started with the synthesis of Intermediates 1 and 2 depicted in Scheme 1, as follows:

(i) Synthesis of N-(thiophene-2-carbonyl)glycine (Intermediate 1). To a solution of glycine (7.0 g, 93 mmol) and potassium carbonate (13.8 g, 100 mmol) in water (100 ml), thiophene-2-carbonyl chloride (7.3 g, 50 mmol) was added over a period of 30 min with stirring. The resulting solution was stirred for 1 hr, washed with diethyl ether (2×30 ml) and acidified with conc. HCl. After cooling for 1 hr in an ice-bath, the precipitate was filtered off, washed with ice-water, and dried in air to yield 7.0 g (76%) of the acid Intermediate 1.

(ii) Synthesis of 2-(2-thienyl)-4-(2-thienylmethylene)oxazol-5(4H)-one (Intermediate 2). A suspension of the acid Intermediates 1 (7.0 g, 38 mmol), thiophene-2-carbaldehyde (5.1 g, 45 mmol), sodium acetate (3.1 g, 38 mmol) and acetic anhydride (11.6 g, 114 mmol) was heated on a steam-bath for 1 hr with stirring. The mixture became orange and solidified during the reaction. The cooled solid was stirred with water (50 ml) for 15 min and the resulting precipitate was filtered off, washed with ice-water and some ice-cooled ethanol, and dried in air to yield 6.2 g (63%) of the azalactone Intermediates 2 as an orange solid.

(iii) Synthesis of Compound 1. The suspension of azalactone 2 (2.8 g, 11 mmol) and 4-amino-N-(4,6-dimethylpyrimidin-2-yl)benzenesulfonamide (2.8 g, 10 mmol) in glacial acetic acid (40 ml) was stirred under reflux for 1 hr. The solids first dissolved and then resulted in a yellow precipitate. After cooling, the latter was filtered off, washed successively with glacial acetic acid, ethanol, and then with diethyl ether and dried in air to yield 3.7 g (69%) of Compound 1 as a light yellow powder.

$^1$H-NMR: 2.25 (s, 6H), 6.74 (s, 1H), 7.15 (m, 1H), 7.26 (m, 1H), 7.50 (m, 1H), 7.70 (s, 1H), 7.73 (s, 1H), 7.87 (m, 3H), 7.94 (m, 2H), 8.09 (m, 1H), 9.90 (s, 1H), 10.43 (s, 1H), 11.66 (s, 1H).

MS (EI): m/z=539 ($C_{24}H_{21}N_5O_4S_3$)

Elemental Analysis Calculated: C, 53.42; H, 3.92; N, 12.98%. Found: C, 53.21; H, 4.01; N, 12.77%.

Light yellow solid, Melting Point: >250° C. (AcOH, dec).

Example 8

Synthesis of Compound 2

For the synthesis of Compound 2, Intermediates 1 and 2 were first synthesized as described in Example 8 above. The synthesis of Compound 2 is depicted in Scheme 2.

A suspension of azalactone (1) (522 mg, 2 mmol) and 4-amino-N'-(2-pyrimidinyl)-1-benzenesulfonamide (500 mg, 2 mmol) in glacial acetic acid (7.3 ml) were stirred under reflux for 1 hr. The solid first dissolved, and then a yellow precipitate was formed. After cooling, the latter was filtered off, washed successively with glacial acetic acid, then with ethanol and diethyl ether, before being dried in vacuo at 100° C. to yield 680 mg (67%) of desired Compound 2.

1H-NMR: 7.02 (m, 1H), 7.15 (m, 1H), 7.26 (m, 1H), 7.52 (m, 1H), 7.69 (s, 1H), 7.73 (m, 1H), 7.94 (m, 5H), 8.09 (m, 1H), 8.50 (m, 1H) 9.97 (s, 1H), 10.46 (s, 1H), 11.69 (s, 1H)

MS (EI): Calculated: 511 Found: [M-H$_2$O]$^+$=493 ($C_{22}H_{17}N_5O_4S_3$)

Elemental Analysis Calculated: C, 51.65; H, 3.35; N, 13.69%. Found (1): C, 51.25, H, 3.47, N 13.57%. Found (2): C, 51.29; H, 3.53; N, 13.49%.

Light yellow solid, Melting Point: >250° C. (AcOH, dec).

Example 9

Synthesis of Compound 4

Compound 4 was synthesized in a similar manner to the synthesis of Compound 1, but is step using (iii) of the synthesis, Intermediate 2 was reacted with 4-amino-5-methyl-N-(4,6-dimethylpyrimidin-2-yl)benzenesulfonamide (2.8 g, 10 mmol). Compound 4 was obtained as light yellow powder in 71% yield.

Example 10

Synthesis of Compound 5

The synthesis of Compound 5, started with the synthesis of Intermediates 3-5 and then reaction with Intermediate 2 as depicted in Scheme 3, as follows:

(i) Synthesis of 1-Acetylindoline-5-sulfonyl chloride (Intermediate 3)

1-Acetylindoline (16.1 g, 100 mmol) was added to chlorosulfonic acid (40.4 g, 350 mmol) under stirring and in small portions over a period of 30 min. The resulting thick solution was stirred at 60° C. for 30 nin, cooled, and treated with crushed ice (200 g) as quickly as possible. The crude sulfonyl chloride (3) was filtered off, washed thoroughly with ice-water, dissolved in chloroform (200 ml), dried briefly with CaCl$_2$, concentrated, and crystallized from ether-hexane to yield 19.5 g (75%) of pure Intermediate 3.

(ii) Synthesis of 1-Acetyl-N-(4-methylpyrimidin-2-yl)indoline-5-sulfonamide (Intermediate 4)

A mixture of 3 (5.2 g, 20 mmol), 2-amino-4-methylpyrimidine (2.1 g, 19 mmol), pyridine (1.74 g, 22 mmol), and 1,2-dichloroethane (15 ml) was stirred at 45-50° C. for 5 hr. The volatiles were distilled off in vacuo and the residue was suspended in water (20 ml). The crude Intermediate 4 was filtered off, washed with water, and then with cold ethanol to give 3.63 g (52%) of a yellowish powder. This substance was used in the next step without further purification.

(iii) Synthesis of N-(4-Methylpyrimidin-2-yl)indoline-5-sulfonamide (Intermediate 5)

A solution of sulfonamide 4 (3.63 g, 10 mmol) in 8% NaOH (15 ml) was stirred at 95-100° C. for 3 hr, cooled and filtered. Then the filtrate was neutralized with 25% HCl. The precipitate formed, was filtered off and washed with water and ethanol. It was purified further by dissolving in 5% NaOH, followed by precipitating with 5% HCl. The precipitate was washed with water and ethanol and dried at 80° C. on air to yield 2.57 g (80%) of Intermediate 5.

(iv) Synthesis of Compound

A suspension of Intermediate 2 (1.4 g, 5.5 mmol), obtained in Example 7 (ii) above and Intermediate 5 (1.8 g, 5.5 mmol) in glacial acetic acid (30 ml) was stirred under reflux for 1 hr. The solids were first dissolved, and then a yellow precipitate was formed. After cooling, the latter was filtered off and washed successively with glacial acetic acid followed by ethanol. The crude product was purified further by dissolving in 5% NaOH followed by precipitating with 5% HCl to give 1.48 g (45%) of pure Compound 5 (N-(4-Methylpyrimidin-2-yl)-1-[3-(2-thienyl)-2-(2-thienylcarbonylamino)]propenoyl]-indoline-5-sulfonamide) as a nearly colorless powder (m.p. >250° C., dec).

¹H-NMR: 2.32 (s, 3H), 3.18 (m, 2H), 4.27 (m, 2H), 6.89 (d, 1H), 7.14 (t, 1H), 7.24 (m, 2H), 7.40 (m, 1H), 7.70 (d, 1H), 7.87 (m, 4H), 8.08 (d, 1H), 8.31 (d, 1H), 10.26 (s, 1H), 11.55 (s, 1H).

Example 11

Synthesis of Compound 7

Compound 7 was synthesized in a similar manner to the synthesis of Compound 5, but using 1-H indole as the starting material in step (i) of the synthesis. Compound 7 was obtained as a colorless powder in 50% yield.

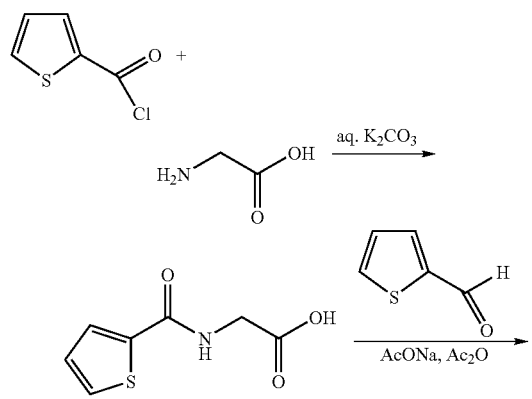

Scheme 1

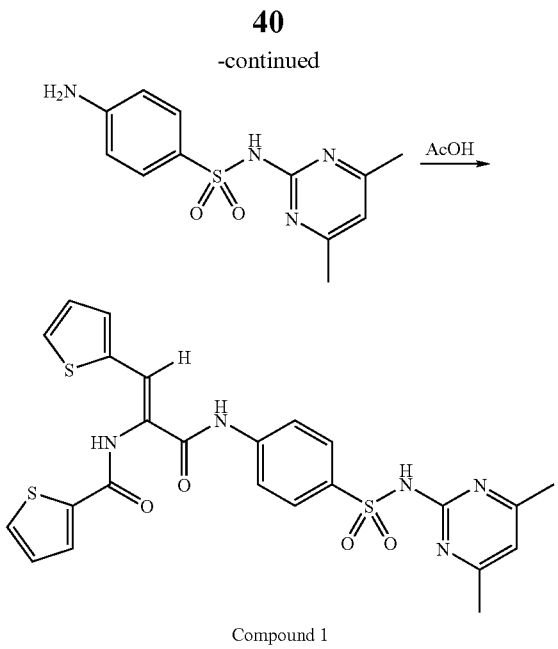

Scheme 2

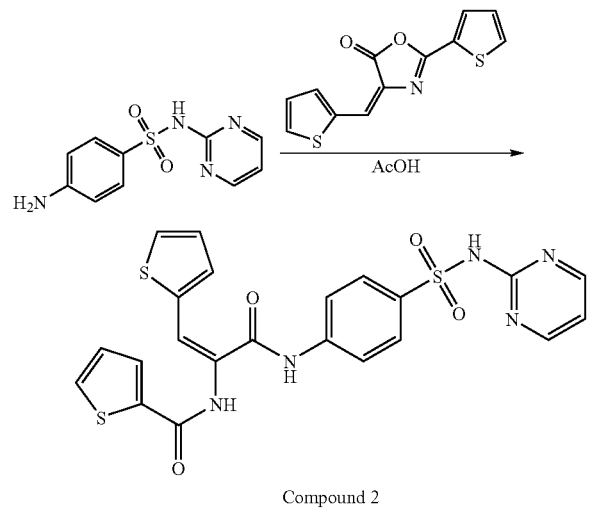

Scheme 3

-continued
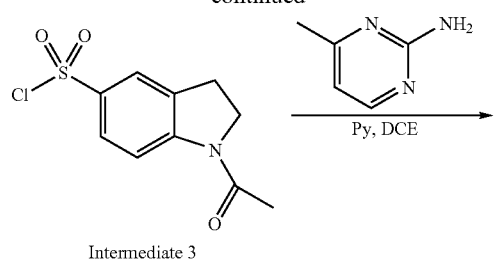
Intermediate 3
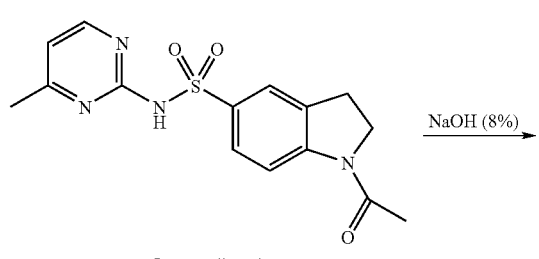
Intermediate 4
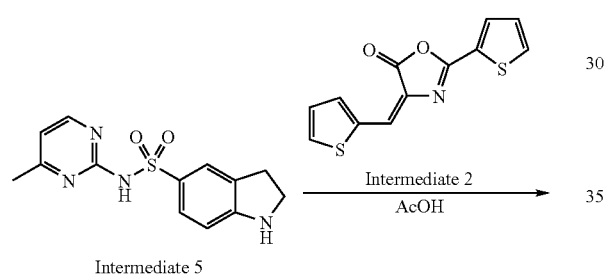
Intermediate 5
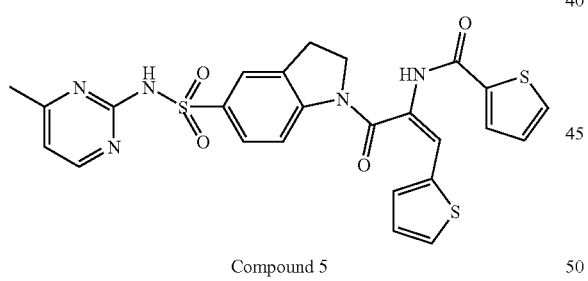
Compound 5
Appendix A
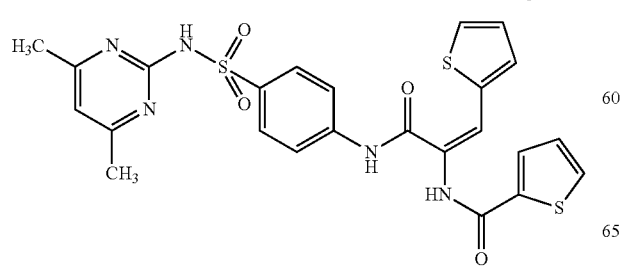
Compound 1
-continued
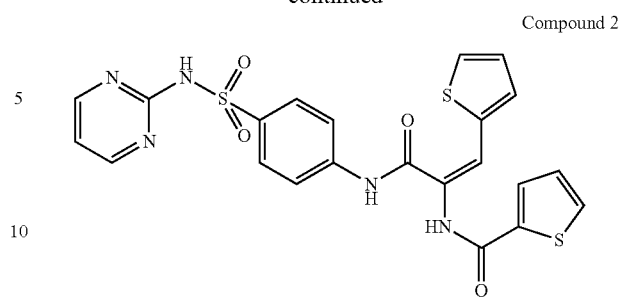
Compound 2
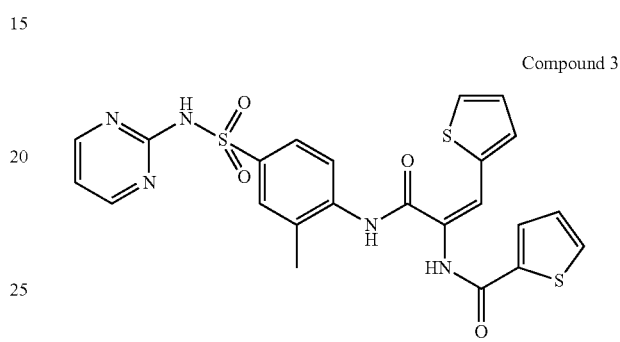
Compound 3
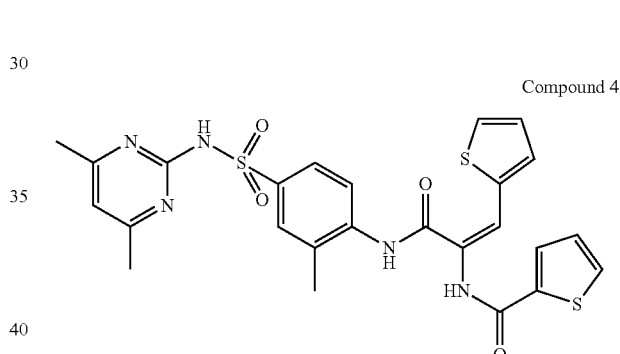
Compound 4
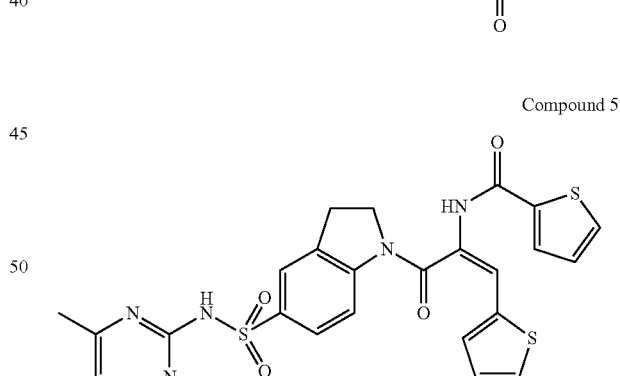
Compound 5
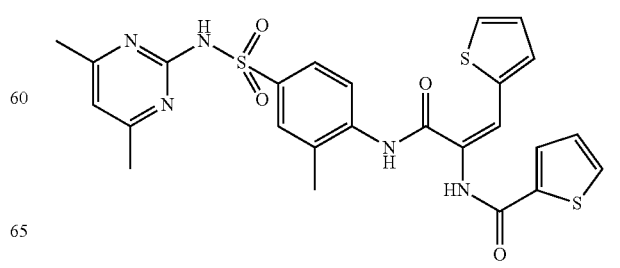
Compound 6

Compound 7

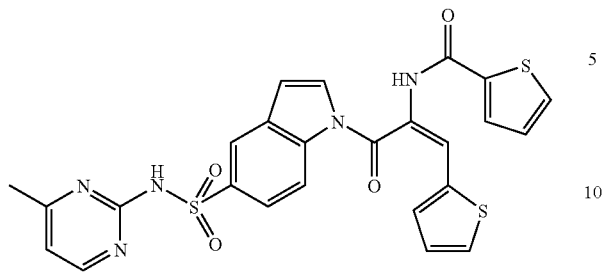

The invention claimed is:

1. A compound of the general formula I

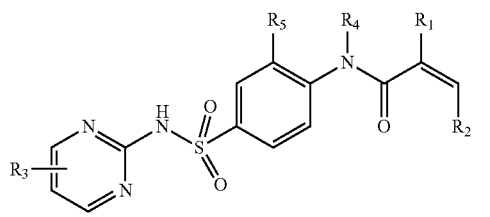

wherein
- $R_1$ is alkyl, aryl, heteroaryl, —$COR_6$, —$COOR_6$, —$NR_7R_8$, —$CONR_7R_8$ or —$NR_9COR_{10}$;
- $R_2$ is aryl or heteroaryl;
- $R_3$ represents H or one to three radicals selected from the group consisting of lower alkyl, lower alkoxy, halogen, —$NR_7R_8$, —$COOR_6$ and —$CONR_7R_8$;
- $R_4$ is H, alkyl, aryl, carbocyclyl, acyl, —OH or heterocyclyl;
- $R_5$ is H, halogen, alkyl, aryl, heteroaryl, —$OR_6$, —$SR_6$, —$COR_6$, —$COOR_6$, —$NR_7R_8$, —$CONR_7R_8$ or —$NR_9COR_{10}$; or $R_4$ and $R_5$ together with the carbon and nitrogen atoms to which they are attached form a 5-6 membered heterocyclic ring optionally containing a further double bond;
- $R_6$ is H, ($C_2$-$C_{20}$) hydrocarbyl or heterocyclyl;
- $R_7$ and $R_8$ are each independently H, hydrocarbyl or heterocyclyl; or $R_7$ and $R_8$ together with the nitrogen atom to which they are attached form a 5-6 membered saturated heterocyclic ring, optionally containing 1 or 2 further heteroatoms selected from the group consisting of N, S and O, and wherein said further N atom is optionally substituted by lower alkyl, aralkyl, haloalkyl or hydroxyalkyl;
- $R_9$ is H, lower alkyl or phenyl;
- $R_{10}$ is aryl or heteroaryl;
- wherein said hydrocarbyl, heterocyclyl, aryl and heteroaryl is optionally substituted by one or more radicals selected from the group consisting of lower alkyl, halogen, aryl, heterocyclyl, heteroaryl, nitro, epoxy, epithio, —$OR_6$, —$SR_6$, —$COR_6$, —$COOR_6$, —$NR_7R_8$, —$CONR_7R_8$, —$NR_7$—$COR_6$, —$SO_3R_6$, —$SO_2R_6$, —$SO_2NR_7R_8$ and —$NR_7SO_2R_6$, wherein $R_6$, $R_7$ and $R_8$ are as defined above;

or an enantiomer or a pharmaceutically acceptable salt thereof.

2. A compound according to claim 1, wherein:
- $R_1$ is $NR_9COR_{10}$;
- $R_2$ is a heteroaryl;
- $R_3$ is H or one to three lower alkyl radicals;
- $R_4$ is H, alkyl, carbocyclyl, aryl, acyl, —OH or heterocyclyl;
- $R_5$ is H, halogen, alkyl, aryl, heteroaryl, —$OR_6$, —$SR_6$, —$COR_6$, —$COOR_6$, —$NR_7R_8$, —$CONR_7R_8$ or —$NR_9COR_{10}$; or $R_4$, the nitrogen atom to which it is attached and $R_5$ form a 5-6 membered heterocyclic ring;
- $R_6$ is H, ($C_2$-$C_4$) alkyl, aryl or heterocyclyl;
- $R_7$ and $R_8$ each independently is H, alkyl, aryl or heterocyclyl, or $R_7$ and $R_8$ together with the nitrogen atom to which they are attached form a saturated 5-6 membered heterocyclic ring, optionally containing 1 or 2 further heteroatoms selected from the group consisting of N, S and O, and wherein said further N atom is optionally substituted by lower alkyl, aralkyl, haloalkyl or hydroxyalkyl;

$R_9$ is H, lower alkyl or phenyl;

$R_{10}$ is aryl or heteroaryl;

wherein said alkyl, carbocyclyl, heterocyclyl, aryl and heteroaryl is optionally substituted by one or more radicals selected from the group consisting of halogen, lower alkyl, aryl, heterocyclyl, nitro, epoxy, epithio, —$OR_6$, —$SR_6$, —$COR_6$, —$COOR_6$, —$NR_7R_8$, —$CONR_7R_8$, —$NR_7COR_6$, —$SO_3R_6$, —$SO_2R_6$, —$SO_2NR_7R_8$ and —$NR_7SO_2R_6$, wherein $R_7$ and $R_8$ are each independently H, hydrocarbyl or heterocyclyl; or $R_7$ and $R_8$ together with the nitrogen atom to which they are attached form a saturated 5-6 membered heterocyclic ring, optionally containing 1 or 2 further heteroatoms selected from the group consisting of N, S and O, and wherein said further N atom is optionally substituted by lower alkyl, aralkyl, haloalkyl or hydroxyalkyl.

3. The compound according to claim 1, wherein: (i) said hydrocarbyl is a straight or branched, acyclic or cyclic, saturated, unsaturated or aromatic, hydrocarbyl radical, of 1-20 carbon atoms, selected from the group consisting of an alkyl, alkenyl, alkynyl, carbocyclyl, aryl and an aralkyl radicals;

said alkyl is a straight or branched alkyl of 1 to 10 carbon atoms ($C_1$-$C_{10}$ alkyl), or a lower alkyl ($C_1$-$C_4$ alkyl) selected from the group consisting of methyl, ethyl, n-propyl, isopropyl, sec-butyl and tert-butyl, optionally interrupted by one or more heteroatoms selected from the group consisting of O, S and N, and/or substituted by one or more radicals selected from the group consisting of halogen, aryl, heteroaryl, heterocyclyl, nitro, epoxy, epithio, —OR, —SR, —COR, —COOR, —NRR', —CONRR', —NRCOR', —$SO_3R$, —$SO_2R$, —$SO_2NRR'$ and —$NRSO_2R$, wherein R and R' are each independently H, hydrocarbyl or heterocyclyl; or R and R' together with the nitrogen atom to which they are attached form a saturated 5-6 membered heterocyclic ring, optionally containing 1 or 2 further heteroatoms selected from the group consisting of N, S and O, said further N atom is optionally substituted by lower alkyl, aralkyl, haloalkyl or hydroxyalkyl;

said carbocyclyl is a saturated $C_5$-$C_6$ cycloalkyl or partially unsaturated $C_5$-$C_6$ cycloalkenyl radical selected from the group consisting of cyclopropyl, cyclobutyl, cyclopentyl, cyclopentenyl, cyclohexyl and cyclohexenyl, optionally substituted by one or more radicals selected from the group consisting of halogen, hydrocarbyl, heterocyclyl, nitro, epoxy, epithio, OR, —SR, —COR, —COOR, —NRR', —CONRR', —NRCOR', —$SO_3R$, —$SO_2R$, —$SO_2NRR'$ and —$NRSO_2R$, wherein R and R', are each independently H, hydrocarbyl or heterocyclyl, or R and R' together with the nitrogen atom to which they are attached form a saturated 5-6 membered heterocyclic ring, optionally containing 1 or 2 further heteroatoms selected from the group consisting of N, S and O, and wherein said further N atom is optionally substituted by lower alkyl, aralkyl, haloalkyl or hydroxyalkyl;

said aryl is a substituted or unsubstituted monocyclic, bicyclic or tricyclic aromatic carbocyclic radical of 6 to 14 carbon atoms, selected from the group consisting of phenyl, biphenyl, naphthyl, and anthracenyl;

(ii) said heterocyclyl is a saturated or partially unsaturated, optionally substituted, monocyclic, bicyclic or tricyclic heterocycle, of 3 to 12 ring members, of which one to three atoms is a heteroatom selected from the group consisting of O, S and N; and (iii) said heteroaryl is a substituted or unsubstituted mono- or poly-cyclic heteroaromatic ring containing one to three heteroatoms selected from the group consisting of O, S and N.

4. A compound according to claim 1, of the formula Ia or Ib:

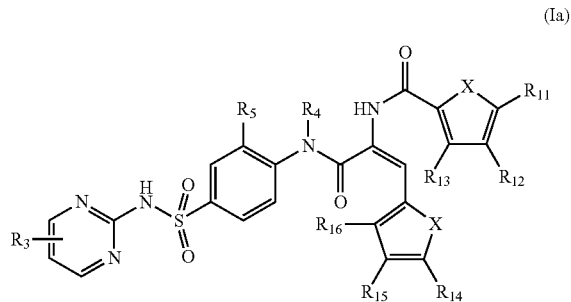

(Ia)

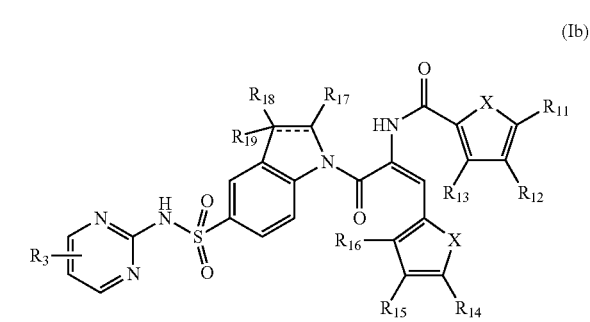

(Ib)

wherein

X is O, S or NH;

$R_3$ is H or one to three ($C_1$-$C_4$) alkyls;

$R_4$ is H or ($C_1$-$C_4$) alkyl;

$R_5$ is H or ($C_1$-$C_6$) alkyl;

and $R_{11}$ to $R_{19}$, each independently is selected from the group consisting of H, lower alkyl, halogen, aryl, heterocyclyl, heteroaryl, nitro, epoxy, epithio, —$OR_6$, —$SR_6$, —$COR_6$, —$COOR_6$, —$NR_7R_8$, —$CONR_7R_8$, —$NR_7$—$COR_6$, —$SO_3R_6$, —$SO_2R_6$, —$SO_2NR_7R_8$ and —$NR_7SO_2R_6$, wherein $R_6$, $R_7$ and $R_8$ are each independently H, alkyl, aryl or heterocyclyl; or $R_7$ and $R_8$ together with the nitrogen atom to which they are attached form a saturated 5-6 membered heterocyclic ring, optionally containing 1 or 2 further heteroatoms selected from the group consisting of N, S and O, and wherein said further N atom is optionally substituted by lower alkyl, optionally substituted by phenyl, halogen or hydroxy; and the dotted line in formula Ib represents an optional double bond.

5. The compound of formula Ia according to claim 4, wherein X is S, $R_3$ is H or one to three methyl groups, $R_4$ is H, $R_5$ is H or methyl and $R_{11}$ to $R_{16}$ are H, selected from the group consisting of:

Compound 1 of the formula:

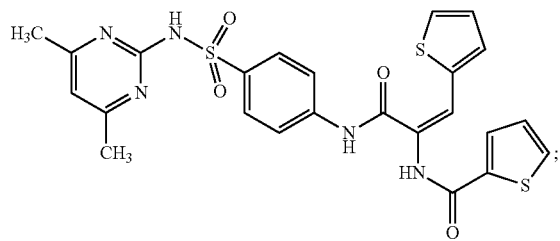

Compound 2 of the formula:

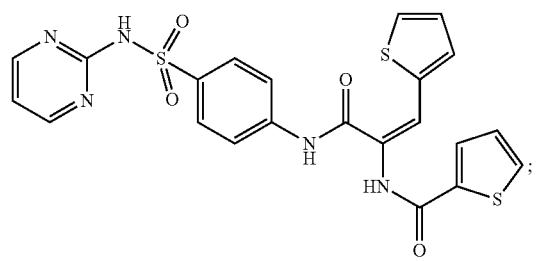

Compound 3 of the formula:

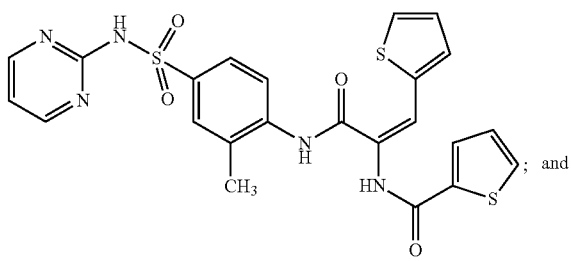

Compound 4 of the formula:

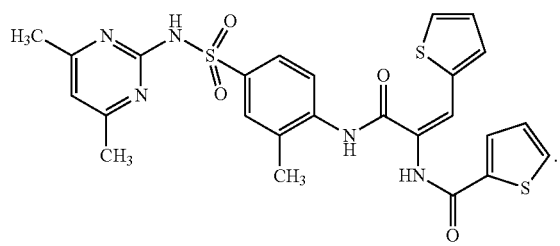

6. The compound of formula Ib according to claim 4, wherein X is S, $R_3$ is H or one to three methyl groups and $R_{11}$ to $R_{19}$ are H, selected from the group consisting of:

Compound 5 of the formula:

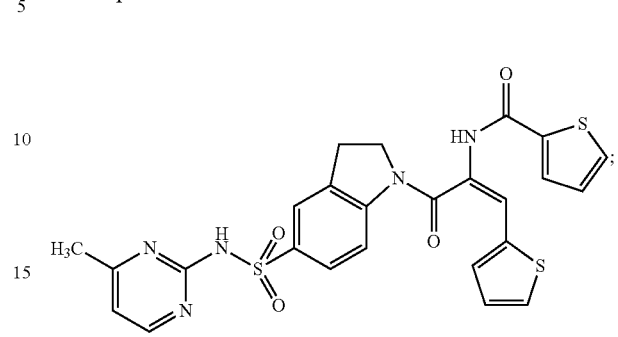

Compound 6 of the formula:

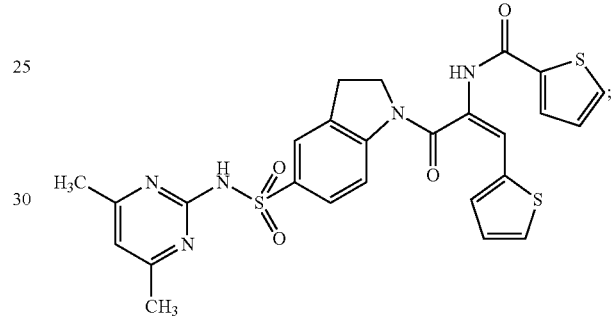

and

Compound 7 of the formula:

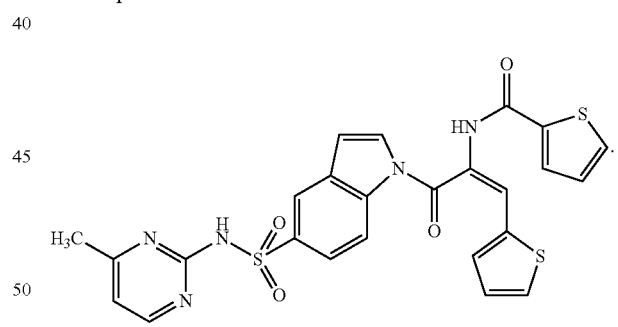

7. A method for treatment of a viral infection, which comprises administering to a subject in need a compound of formula I according to claim 1 in an amount effective for inhibiting said viral infection.

8. The method according to claim 7, wherein said viral infection is caused by an envelope virus such as an RNA virus or a retroid virus.

9. The method according to claim 8, wherein said retroid virus is a lentivirus selected from the group consisting of human immunodeficiency virus type-1 (HIV-1), human immunodeficiency virus type-2 (HIV-2), hepatitis B virus (HBV), hepatitis C virus (HCV), Ebola virus, and human T-cell leukemia Virus (HTLV).

10. The method for treatment of a viral infection caused by HIV-1 or HIV-2 in a subject according to claim 9, comprising administering to said subject an anti-HIV-1 or anti-HIV-2 effective amount of a compound selected from the group consisting of:

Compound 1

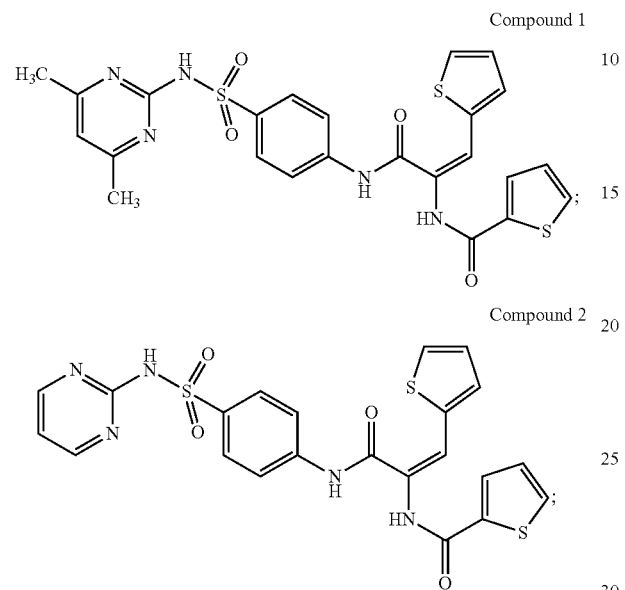

and

Compound 5

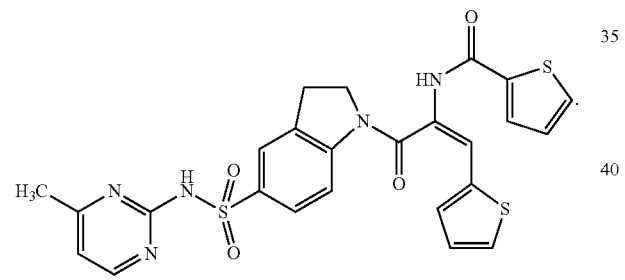

11. A pharmaceutical composition comprising a compound of the general formula I according to claim 1 and a pharmaceutically acceptable carrier.

12. The pharmaceutical composition according to claim 11, comprising a compound selected from the group consisting of:

Compound 1

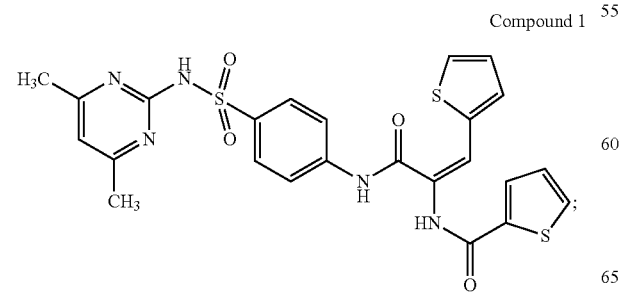

-continued

Compound 2

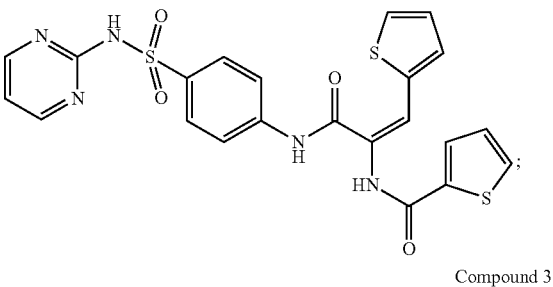

Compound 3

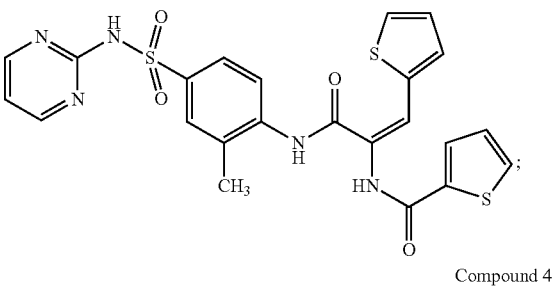

Compound 4

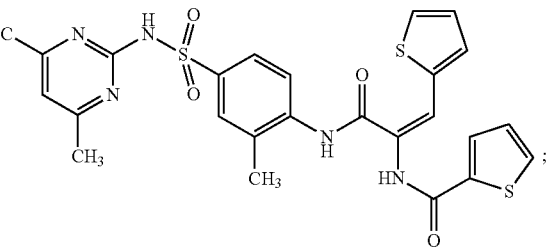

Compound 5

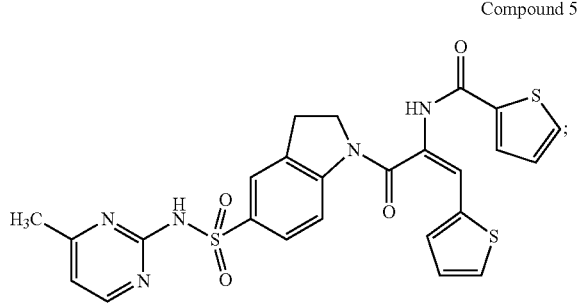

Compound 6

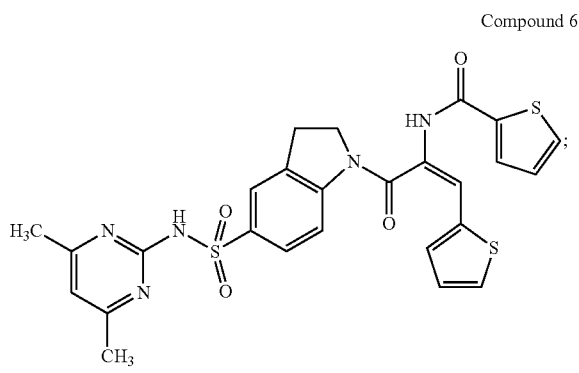

and

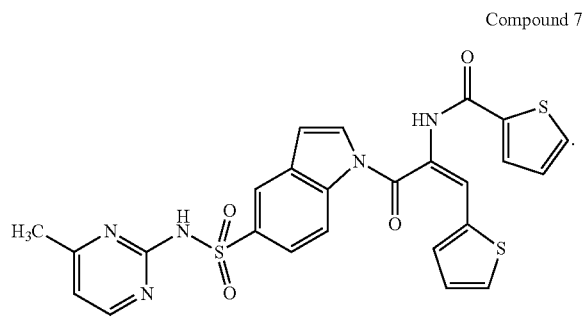

Compound 7

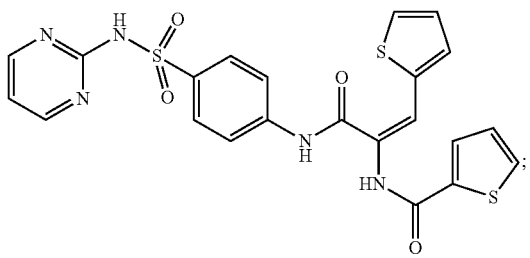

Compound 2

13. The pharmaceutical composition according to claim 11, for treatment of a viral infection.

14. The pharmaceutical composition according to claim 13, for treatment of a viral infection caused by an envelope virus selected from an RNA virus or a retroid virus.

15. The pharmaceutical composition according to claim 14, wherein said retroid virus is a lentivirus selected from the group consisting of human immunodeficiency virus type-1 (HIV-1), human immunodeficiency virus type-2 (HIV-2), hepatitis B virus (HBV), hepatitis C virus (HCV), Ebola virus, and human T-cell leukemia Virus (HTLV).

16. The pharmaceutical composition according to claim 15, comprising a compound selected from the group consisting of:

and

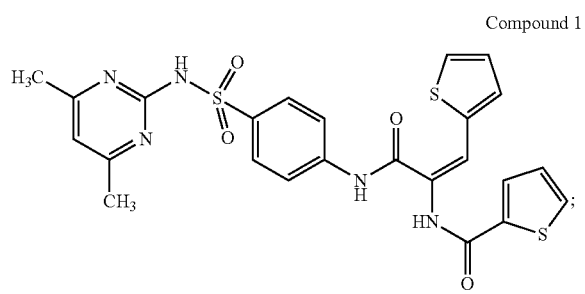

Compound 1

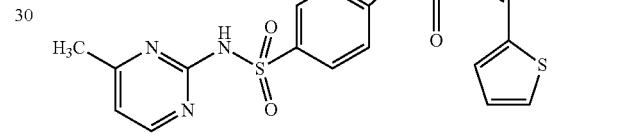

Compound 5 for treatment of a viral infection caused by HIV-1 or HIV-2.

* * * * *

SEQUENCE LISTING

<160> NUMBER OF SEQ ID NOS: 21

<210> SEQ ID NO 1
<211> LENGTH: 836
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Arg Thr Leu Val Gly Ser Gly Val Glu Glu Leu Pro Ser Asn Ile Leu
1               5                   10                  15

Leu Val Arg Leu Leu Asp Gly Ile Lys Gln Arg Pro Trp Lys Pro Gly
            20                  25                  30

Pro Gly Gly Gly Ser Gly Thr Asn Cys Thr Asn Ala Leu Arg Ser Gln
        35                  40                  45

Ser Ser Thr Val Ala Asn Cys Ser Ser Lys Asp Leu Gln Ser Ser Gln
    50                  55                  60

Gly Gly Gln Gln Pro Arg Val Gln Ser Trp Ser Pro Val Arg Gly
65                  70                  75                  80

Ile Pro Gln Leu Pro Cys Ala Lys Ala Leu Tyr Asn Tyr Glu Gly Lys
                85                  90                  95

Glu Pro Gly Asp Leu Lys Phe Ser Lys Gly Asp Ile Ile Ile Leu Arg
            100                 105                 110

Arg Gln Val Asp Glu Asn Trp Tyr His Gly Glu Val Asn Gly Ile His
        115                 120                 125

Gly Phe Phe Pro Thr Asn Phe Val Gln Ile Ile Lys Pro Leu Pro Gln
    130                 135                 140

Pro Pro Pro Gln Cys Lys Ala Leu Tyr Asp Phe Glu Val Lys Asp Lys
145                 150                 155                 160

Glu Ala Asp Lys Asp Cys Leu Pro Phe Ala Lys Asp Asp Val Leu Thr
                165                 170                 175

Val Ile Arg Arg Val Asp Glu Asn Trp Ala Glu Gly Met Leu Ala Asp
            180                 185                 190

Lys Ile Gly Ile Phe Pro Ile Ser Tyr Val Glu Phe Asn Ser Ala Ala
        195                 200                 205

Lys Gln Leu Ile Glu Trp Asp Lys Pro Pro Val Pro Gly Val Asp Ala
    210                 215                 220

Gly Glu Cys Ser Ser Ala Ala Ala Gln Ser Ser Thr Ala Pro Lys His
225                 230                 235                 240

Ser Asp Thr Lys Lys Asn Thr Lys Lys Arg His Ser Phe Thr Ser Leu

```
                    245                 250                 255
Thr Met Ala Asn Lys Ser Ser Gln Ala Ser Gln Asn Arg His Ser Met
                260                 265                 270
Glu Ile Ser Pro Pro Val Leu Ile Ser Ser Ser Asn Pro Thr Ala Ala
                275                 280                 285
Ala Arg Ile Ser Glu Leu Ser Gly Leu Ser Cys Ser Ala Pro Ser Gln
                290                 295                 300
Val His Ile Ser Thr Thr Gly Leu Ile Val Thr Pro Pro Ser Ser
305                 310                 315                 320
Pro Val Thr Thr Gly Pro Ser Phe Thr Phe Pro Ser Asp Val Pro Tyr
                325                 330                 335
Gln Ala Ala Leu Gly Thr Leu Asn Pro Pro Leu Pro Pro Pro Leu
                340                 345                 350
Leu Ala Ala Thr Val Leu Ala Ser Thr Pro Gly Ala Thr Ala Ala
                355                 360                 365
Ala Ala Ala Ala Gly Met Gly Pro Arg Pro Met Ala Gly Ser Thr Asp
                370                 375                 380
Gln Ile Ala His Leu Arg Pro Gln Thr Arg Pro Ser Val Tyr Val Ala
385                 390                 395                 400
Ile Tyr Pro Tyr Thr Pro Arg Lys Glu Asp Glu Leu Glu Leu Arg Lys
                405                 410                 415
Gly Glu Met Phe Leu Val Phe Glu Arg Cys Gln Asp Gly Trp Phe Lys
                420                 425                 430
Gly Thr Ser Met His Thr Ser Lys Ile Gly Val Phe Pro Gly Asn Tyr
                435                 440                 445
Val Ala Pro Val Thr Arg Ala Val Thr Asn Ala Ser Gln Ala Lys Val
                450                 455                 460
Pro Met Ser Thr Ala Gly Gln Thr Ser Arg Gly Val Thr Met Val Ser
465                 470                 475                 480
Pro Ser Thr Ala Gly Gly Pro Ala Gln Lys Leu Gln Gly Asn Gly Val
                485                 490                 495
Ala Gly Ser Pro Ser Val Val Pro Ala Ala Val Val Ser Ala Ala His
                500                 505                 510
Ile Gln Thr Ser Pro Gln Ala Lys Val Leu Leu His Met Thr Gly Gln
                515                 520                 525
Met Thr Val Asn Gln Ala Arg Asn Ala Val Arg Thr Val Ala Ala His
                530                 535                 540
Asn Gln Glu Arg Pro Thr Ala Val Thr Pro Ile Gln Val Gln Asn
545                 550                 555                 560
Ala Ala Gly Leu Ser Pro Ala Ser Val Gly Leu Ser His His Ser Leu
                565                 570                 575
Ala Ser Pro Gln Pro Ala Pro Leu Met Pro Gly Ser Ala Thr His Thr
                580                 585                 590
Ala Ala Ile Ser Ile Ser Arg Ala Ser Ala Pro Leu Ala Cys Ala Ala
                595                 600                 605
Ala Ala Pro Leu Thr Ser Pro Ser Ile Thr Ser Ala Ser Leu Glu Ala
                610                 615                 620
Glu Pro Ser Gly Arg Ile Val Thr Val Leu Pro Gly Leu Pro Thr Ser
625                 630                 635                 640
Pro Asp Ser Ala Ser Ser Ala Cys Gly Asn Ser Ser Ala Thr Lys Pro
                645                 650                 655
Asp Lys Asp Ser Lys Lys Glu Lys Lys Gly Leu Leu Lys Leu Leu Ser
                660                 665                 670
```

Gly Ala Ser Thr Lys Arg Lys Pro Arg Val Ser Pro Pro Ala Ser Pro
            675                 680                 685

Thr Leu Glu Val Glu Leu Gly Ser Ala Glu Leu Pro Leu Gln Gly Ala
        690                 695                 700

Val Gly Pro Glu Leu Pro Pro Gly Gly His Gly Arg Ala Gly Ser
705                 710                 715                 720

Cys Pro Val Asp Gly Asp Gly Pro Val Thr Thr Ala Val Ala Gly Ala
                725                 730                 735

Ala Leu Ala Gln Asp Ala Phe His Arg Lys Ala Ser Ser Leu Asp Ser
            740                 745                 750

Ala Val Pro Ile Ala Pro Pro Arg Gln Ala Cys Ser Ser Leu Gly
        755                 760                 765

Pro Val Leu Asn Glu Ser Arg Pro Val Val Cys Glu Arg His Arg Val
770                 775                 780

Val Val Ser Tyr Pro Pro Gln Ser Glu Ala Glu Leu Glu Leu Lys Glu
785                 790                 795                 800

Gly Asp Ile Val Phe Val His Lys Lys Arg Glu Asp Gly Trp Phe Lys
            805                 810                 815

Gly Thr Leu Gln Arg Asn Gly Lys Thr Gly Leu Phe Pro Gly Ser Phe
        820                 825                 830

Val Glu Asn Ile
        835

<210> SEQ ID NO 2
<211> LENGTH: 1502
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
agagacgtga acggtcgttg cagagattgc gggcggctga acgccgcct gcctggcacc      60 taggagcgca gcggagcccc gacaccgccg ccgccgccat ggagtccgag accgaacccg    120
agcccgtcac gctcctggtg aagagcccca accagcgcca ccgcgacttg agctgagtg     180 gcgaccgcgg ctggagtgtg gccacctca aggcccacct gagccgcgtc taccccgagc    240
gtccgcgtcc agaggaccag aggttaattt attctgggaa gctgttgttg atcaccaat    300 gtctcaggga cttgcttcca aaggaaaaac ggcatgtttt gcatctggtg tgcaatgtga    360
agagtccttc aaaaatgcca gaaatcaacg ccaaggtggc tgaatccaca gaggagcctg    420
ctggttctaa tcggggacag tatcctgagg attcctcaag tgatggttta aggcaaaggg    480
aagttcttcg gaacctttct tcccctggat gggaaaacat ctcaaggcat acgttgggt    540 ggtttccatt tagaccgagg ccggttcaga acttcccaaa tgatggtcct cctcctgacg    600
ttgtaaatca ggaccccaac aataacttac aggaaggcac tgatcctgaa actgaagacc    660
ccaaccacct ccctccagac agggatgtac tagatggcga gcagaccagc ccctccttta    720
tgagcacagc atggcttgtc ttcaagactt tctttgcctc tcttcttcca gaaggccccc    780
cagccatcgc aaactgatgg tgtttgtgct gtagctgttg gaggctttga caggaatgga    840
ctggatcacc tgactccagc tagattgcct ctcctggaca tggcaatgat gagtttttaa    900
aaaacagtgt ggatgatgat atgctttgt gagcaagcaa aagcagaaac gtgaagccgt    960
gatacaaatt ggtgaacaaa aaatgccaa ggcttctcat gtctttattc tgaagagctt    1020
taatatatac tctatgtagt ttaataagca ctgtacgtag aaggccttag gtgttgcatg    1080

```
tctatgcttg aggaactttt ccaaatgtgt gtgtctgcat gtgtgtttgt acatagaagt    1140
catagatgca gaagtggttc tgctggtacg atttgattcc tgttggaatg tttaaattac    1200
actaagtgta ctactttata taatcaatga aattgctaga catgttttag caggactttt    1260
ctaggaaaga cttatgtata attgcttttt aaaatgcagt gctttacttt aaactaaggg    1320
gaactttgcg gaggtgaaaa cctttgctgg gttttctgtt caataaagtt ttactatgaa    1380
tgaccctgaa aaaaaaaaa aaaaaaaaaa aaaaaaaaaa aaaaaaaaaa aaaaaaaaa    1440 aaaaaaaaaa aaaaaaaaaa aaaaaaaaaa aaaaaaaaaa aaaaaaaaaa aaaaaaaaaa    1500
aa                                                                   1502

<210> SEQ ID NO 3
<211> LENGTH: 2217
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
gctgtgtggc ccaggctttt ctcaaactcc tgagggcaag cgatcctccc acctcagcct      60
cctgagtagc tgggactaca ggcatgtgcc actagacctg gctctaaaga catatatgac     120
acacgaaacc atttattttt catttcacaa tgtttattca catatatggt attagtattc     180
taatgtagtg atgcactcta aatttgcatt atatttccta gaacatctga acagagcata     240
ggaaattccc tattttgcca ttatcagttc taacaaaaat cttaaaagca ctttatcatt     300
tcatttccct gcactgtaat ttttttaaat gatcaaaaac agtatcatac caaggcttac     360
ttatattgga atactatttt agaaagttgt gggctgggtt gtatttataa atcttgttgg     420
tcagatgtct gcaatgagta aatttagcac cattatcagg aagctttctc accaatgaca     480
acttcattgg aagattttaa tgaaagtgta gcatactcta gggaaaaaat atgaatattt     540
tagcatctat gtattgaaaa ttatgttgaa taaatgtcag actattttt acataacgtt      600 gcttctgttt aattttgtca cgttcagagg tgggggtag gagatgtaag cccttgacag      660
caaaataatt ccttttgctt gatttcagac agttgcatca gctcctttgt tctgtgttca     720
tgttacactt atttaggtgg ctgaatccac agaggagcct gctggttcta atcggggaca     780
gtatcctgag gattcctcaa gtgatggttt aaggcaaagg gaagttcttc ggaacctttc     840 ttccctgga tgggaaaaca tctcaaggcc tgaagctgcc cagcaggcat tccaaggcct      900
gggtcctggt ttctccggtt acacaccta tgggtggctt cagcttcct ggttccagca      960 gatatatgca cgacagtact acatgcaata tttagcagcc actgctgcat caggggcttt    1020
tgttccacca ccaagtgcac aagagatacc tgtggtctct gcacctgctc cagcccctat    1080
tcacaaccag tttccagctg aaaaccagcc tgccaatcag aatgctgctc ctcaagtggt    1140
tgttaatcct ggagccaatc aaaatttgcg gatgaatgca caagtggcc ctattgtgga     1200 agaagatgat gaaataaatc gagattggtt ggattggacc tattcagcag ctacattttc    1260
tgtttttctc agtatcctct acttctactc ctccctgagc agattcctca tggtcatggg    1320
ggccaccgtt gttatgtacc tgcatcacgt tgggtggttt ccatttagac cgaggccggt    1380
tcagaacttc ccaaatgatg gtcctcctcc tgacgttgta aatcaggacc caacaataa    1440 cttacaggaa ggcactgatc ctgaaactga agaccccaac cacctccctc agacaggga    1500 tgtactagat ggcgagcaga ccagccctc ctttatgagc acagcatggc ttgtcttcaa    1560
gactttcttt gcctctcttc ttccagaagg ccccccagcc atcgcaaact gatggtgttt   1620
```

| | |
|---|---|
| gtgctgtagc tgttggaggc tttgacagga atggactgga tcacctgact ccagctagat | 1680 |
| tgcctctcct ggacatggca atgatgagtt tttaaaaaac agtgtggatg atgatatgct | 1740 |
| tttgtgagca agcaaaagca gaaacgtgaa gccgtgatac aaattggtga acaaaaaatg | 1800 |
| cccaaggctt ctcatgtctt tattctgaag agctttaata tatactctat gtagtttaat | 1860 |
| aagcactgta cgtagaaggc cttaggtgtt gcatgtctat gcttgaggaa cttttccaaa | 1920 |
| tgtgtgtgtc tgcatgtgtg tttgtacata gaagtcatag atgcagaagt ggttctgctg | 1980 |
| gtacgatttg attcctgttg gaatgtttaa attacactaa gtgtactact ttatataatc | 2040 |
| aatgaaattg ctagacatgt tttagcagga cttttctagg aaagacttat gtataattgc | 2100 |
| ttttaaaat gcagtgcttt actttaaact aaggggaact ttgcggaggt gaaaaccttt | 2160 |
| gctgggtttt ctgttcaata aagttttact atgaatgaca aaaaaaaaaa aaaaaaa | 2217 |

<210> SEQ ID NO 4
<211> LENGTH: 1684
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 4

| | |
|---|---|
| ggccacctca aggcccacct gagccgcgtc taccccgagc gtccgcgtcc agaggaccag | 60 |
| aggttaattt attctgggaa gctgttgttg gatcaccaat gtctcaggga cttgcttcca | 120 |
| aaggaaaaac ggcatgtttt gcatctggtg tgcaatgtga agagtccttc aaaaatgcca | 180 |
| gaaatcaacg ccaaggtggc tgaatccaca gaggagcctg ctggttctaa tcggggacag | 240 |
| tatcctgagg attcctcaag tgatggttta aggcaaaggg aagttcttcg gaacctttct | 300 |
| tccctggat gggaaaacat ctcaaggcct gaagctgccc agcaggcatt ccaaggcctg | 360 |
| ggtcctggtt tctccggtta cacaccctat gggtggcttc agcttttctg gttccagcag | 420 |
| atatatgcac gacagtacta catgcaatat ttagcagcca ctgctgcatc aggggctttt | 480 |
| gttccaccac caagtgcaca agagataccc tgtggtctctg cacctgctcc agcccctatt | 540 |
| cacaaccagt ttccagctga aaccagcct gccaatcaga atgctgctcc tcaagtggtt | 600 |
| gttaatcctg gagccaatca aaatttgcgg atgaatgcac aaggtggccc tattgtggaa | 660 |
| gaagatgatg aaataaatcg agattggttg gattggacct attcagcagc tacatttttct | 720 |
| gttttttctca gtatcctcta cttctactcc tccctgagca gattcctcat ggtcatgggg | 780 |
| gccaccgttg ttatgtacct gcatcacgtt gggtggtttc catttagacc gaggccggtt | 840 |
| cagaacttcc caaatgatgg tcctcctcct gacgttgtaa atcaggaccc caacaataac | 900 |
| ttacaggaag gcactgatcc tgaaactgaa gaccccaacc acctccctcc agacagggat | 960 |
| gtactagatg gcgagcagac cagcccctcc tttatgagca cagcatggct tgtcttcaag | 1020 |
| actttctttg cctctcttct tccagaaggc cccccagcca tcgcaaactg atggtgtttg | 1080 |
| tgctgtagct gttggaggct ttgacaggaa tggactggat cacctgactc cagctagatt | 1140 |
| gcctctcctg gacatggcaa tgatgagttt ttaaaaaaca gtgtggatga tgatatgctt | 1200 |
| ttgtgagcaa gcaaaagcag aaacgtgaag ccgtgataca aattggtgaa caaaaaatgc | 1260 |
| ccaaggcttc tcatgtcttt attctgaaga gctttaatat atactctatg tagtttaata | 1320 |
| agcactgtac gtagaaggcc ttaggtgttg catgtctatg cttgaggaac ttttccaaat | 1380 |
| gtgtgtgtct gcatgtgtgt ttgtacatag aagtcataga tgcagaagtg gttctgctgg | 1440 |

| | |
|---|---|
| tacgatttga ttcctgttgg aatgtttaaa ttacactaag tgtactactt tatataatca | 1500 |
| atgaaattgc tagacatgtt ttagcaggac ttttctagga aagacttatg tataattgct | 1560 |
| ttttaaaatg cagtgcttta ctttaaacta aggggaactt tgcggaggtg aaaacctttg | 1620 |
| ctgggttttc tgttcaataa agttttacta tgaatgaccc tgaaaaaaaa aaaaaaaaa | 1680 |
| aaaa | 1684 |

<210> SEQ ID NO 5
<211> LENGTH: 1878
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5

| | |
|---|---|
| ccacgcgtcc gggtcgttgc agagattgcg ggcggctgag acgccgcctg cctggcacct | 60 |
| aggagcgcag cggagccccg acaccgccgc cgccgccatg gagtccgaga ccgaacccga | 120 |
| gcccgtcacg ctcctggtga agagccccaa ccagcgccac cgcgacttgg agctgagtgg | 180 |
| cgaccgcggc tggagtgtgg gccacctcaa ggcccacctg agccgcgtct accccgagcg | 240 |
| tccgcgtcca gaggaccaga ggttaattta ttctgggaag ctgttgttgg atcaccaatg | 300 |
| tctcagggac ttgcttccaa agcaggaaaa acggcatgtt ttgcatctgg tgtgcaatgt | 360 |
| gaagagtcct tcaaaaatgc cagaaatcaa cgccaaggtg gctgaatcca cagaggagcc | 420 |
| tgctggttct aatcggggac agtatcctga ggattcctca agtgatggtt taaggcaaag | 480 |
| ggaagttctt cggaaccttt cttcccctgg atgggaaaac atctcaaggc ctgaagctgc | 540 |
| ccagcaggca ttccaaggcc tgggtcctgg tttctccggt tacacaccct atgggtggct | 600 |
| tcagcttttcc tggttccagc agatatatgc acgacagtac tacatgcaat atttagcagc | 660 |
| cactgctgca tcagggggctt tgttccacc accaagtgca caagagatac ctgtggtctc | 720 |
| tgcacctgct ccagccccta ttcacaacca gtttccagct gaaaaccagc ctgccaatca | 780 |
| gaatgctgct cctcaagtgg ttgttaatcc tggagccaat caaaatttgc ggatgaatgc | 840 |
| acaaggtggc cctattgtgg aagaagatga tgaaataaat cgagattggt tggattggac | 900 |
| ctattcagca gctacatttt ctgttttttct cagtatcctc tacttctact cctcccctgag | 960 |
| cagattcctc atggtcatgg gggccaccgt tgttatgtac ctgcatcacg ttgggtggtt | 1020 |
| tccatttaga ccgaggccgg ttcagaactt cccaaatgat ggtcctcctc ctgacgttgt | 1080 |
| aaatcaggac cccaacaata acttacagga aggcactgat cctgaaactg aagaccccaa | 1140 |
| ccacctccct ccagacaggg atgtactaga tggcgagcag accagcccct cctttatgag | 1200 |
| cacagcatgg cttgtcttca agactttctt tgcctctctt cttccagaag gccccccagc | 1260 |
| catcgcaaac tgatggtgtt tgtgctgtag ctgttggagg ctttgacagg aatggactgg | 1320 |
| atcacctgac tccagctaga ttgcctctcc tggacatggc aatgatgagt ttttaaaaaa | 1380 |
| cagtgtggat gatgatatgc ttttgtgagc aagcaaagca gaaacgtgaa gccgtgatac | 1440 |
| aaattggtga acaaaaaatg cccaaggctt ctcatgtctt tattctgaag agctttaata | 1500 |
| tatactctat gtagtttaat aagcactgta cgtagaaggc cttaggtgtt gcatgtctat | 1560 |
| gcttgaggaa cttttccaaa tgtgtgtgtc tgcatgtgtg tttgtacata gaagtcatag | 1620 |
| atgcagaagt ggttctgctg gtacgatttg attcctgttg gaatgtttaa attacactaa | 1680 |
| gtgtactact ttatataatc aatgaaattg ctagacatgt tttagcagga cttttctagg | 1740 |
| aaagacttat gtataattgc tttttaaaat gcagtgcttt actttaaact aaggggaact | 1800 | ttgcggaggt gaaaaccttt gctgggtttt ctgttcaata aagttttact atgaatgacc    1860 ctgaaaaaaa aaaaaaaa    1878

<210> SEQ ID NO 6
<211> LENGTH: 1864
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
aacggtcgtt gcagagattg cgggcggctg agacgccgcc tgcctggcac ctaggagcgc    60
agcggagccc cgacaccgcc gccgccgcca tggagtccga gaccgaaccc gagcccgtca    120
cgctcctggt gaagagcccc aaccagcgcc accgcgactt ggagctgagt ggcgaccgcg    180
gctggagtgt gggccacctc aaggccacct gagccgcgt ctaccccgag cgtccgcgtc    240
cagaggacca gaggttaatt tattctggga agctgttgtt ggatcaccaa tgtctcaggg    300
acttgcttcc aaagcaggaa aaacggcatg ttttgcatct ggtgtgcaat gtgaagagtc    360
cttcaaaaat gccagaaatc aacgccaagg tggctgaatc cacagaggag cctgctggtt    420
ctaatcgggg acagtatcct gaggattcct caagtgatgg tttaaggcaa agggaagttc    480
ttcggaacct ttcttcccct ggatgggaaa acatctcaag gcctgaagct gcccagcagg    540
cattccaagg cctgggtcct ggtttctccg gttacacacc ctatgggtgg cttcagcttt    600
cctggttcca gcagatatat gcacgacagt actacatgca atatttagca gccactgctg    660
catcaggggc ttttgttcca ccaccaagtg cacaagagat acctgtggtc tctgcacctg    720
ctccagcccc tattcacaac cagtttccag ctgaaaacca gctgccaat cagaatgctg    780 ctcctcaagt ggttgttaat cctggagcca atcaaaattt gcggatgaat gcacaaggtg    840
gccctattgt ggaagaagat gatgaaataa atcgagattg gttggattgg acctattcag    900
cagctacatt ttctgttttt ctcagtatcc tctacttcta ctcctccctg agcagattcc    960
tcatggtcat gggggccacc gttgttatgt acctgcatca cgttgggtgg tttccattta    1020
gaccgaggcc ggttcagaac ttcccaaatg atggtcctcc tcctgacgtt gtaaatcagg    1080
accccaacaa taacttacag gaaggcactg atcctgaaac tgaagacccc aaccacctcc    1140
ctccagacag ggatgtacta gatggcgagc agaccagccc ctcctttatg agcacagcat    1200
ggcttgtctt caagactttc tttgcctctc ttcttccaga aggcccccca gccatcgcaa    1260
actgatggtg tttgtgctgt agctgttgga ggctttgaca ggaatggact ggatcacctg    1320
actccagcta gattgcctct cctggacatg gcaatgatga gttttaaaa acagtgtgg    1380 atgatgatat gcttttgtga gcaagcaaaa gcagaaacgt gaagccgtga tacaaattgg    1440
tgaacaaaaa atgcccaagg cttctcatgt ctttattctg aagagcttta atatatactc    1500
tatgtagttt aataagcact gtacgtagaa ggccttaggt gttgcatgtc tatgcttgag    1560
gaacttttcc aaatgtgtgt gtctgcatgt gtgtttgtac atagaagtca tagatgcaga    1620
agtggttctg ctggtacgat tgattcctg ttggaatgtt taaattacac taagtgtact    1680
actttatata atcaatgaaa ttgctagaca tgttttagca ggactttct aggaaagact    1740 tatgtataat tgcttttta aatgcagtgc tttactttaa actaaggga actttgcgga    1800 ggtgaaaacc tttgctgggt tttctgttca ataaagtttt actatgaaaa aaaaaaaaa    1860 aaaa    1864

<210> SEQ ID NO 7
<211> LENGTH: 1871
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 7

| | | |
|---|---|---|
| gaactgtcgt tgcagagatt gcgggcggct gagacgccgc ctgcctggca cctaggagcg | 60 |
| cagcggagcc ccgacaccgc cgccgccgcc atggagtccg agaccgaacc cgagcccgtc | 120 |
| acgctcctgg tgaagagccc caaccagcgc caccgcgact ggagctgag tggcgaccgc | 180 |
| ggctggagtg tgggccacct caaggccac ctgagccgcg tctaccccga cgtccgcgt | 240 |
| ccagaggacc agaggttaat ttattctggg aagctgttgt tggatcacca atgtctcagg | 300 |
| gacttgcttc caaagcagga aaacggcat gttttgcatc tggtgtgcaa tgtgaagagt | 360 |
| ccttcaaaaa tgccagaaat aacgccaag gtggctgaat ccacagagga gcctgctggt | 420 |
| tctaatcggg gacagtatcc tgaggattcc tcaagtgatg gtttaaggca agggaagtt | 480 |
| cttcggaacc tttcttcccc tggatgggaa acatctcaa ggcctgaagc tgcccagcag | 540 |
| gcattccaag gcctgggtcc tggtttctcc ggttacacac cctatgggtg cttcagctt | 600 |
| tcctggttcc agcagatata tgcacgacag tactacatgc aatatttagc agccactgct | 660 |
| gcatcagggg cttttgttcc accaccaagt gcacaagaga tacctgtggt ctctgcacct | 720 |
| gctccagccc ctattcacaa ccagtttcca gctgaaaacc agcctgccaa tcagaatgct | 780 |
| gctcctcaag tggttgttaa tcctggagcc aatcaaaatt gcggatgaa tgcacaaggt | 840 |
| ggccctattg tggaagaaga tgatgaaata atcgagatt ggttggattg gacctattca | 900 |
| gcagctacat tttctgtttt tctcagtatc ctctacttct actcctccct gagcagattc | 960 |
| ctcatggtca tggggccac cgttgttatg tacctgcatc acgttgggtg gtttccattt | 1020 |
| agaccgaggc cggttcagaa cttcccaaat gatggtcctc ctcctgacgt tgtaaatcag | 1080 |
| gaccccaaca taacttaca ggaaggcact gatcctgaaa ctgaagaccc caaccacctc | 1140 |
| cctccagaca gggatgtact agatggcgag cagaccagcc cctccttat gagcacagca | 1200 |
| tggcttgtct tcaagacttt ctttgcctct cttcttccag aaggccccc agccatcgca | 1260 |
| aactgatggt gtttgtgctg tagctgttgg aggctttgac aggaatggac tggatcacct | 1320 |
| gactccagct agattgcctc tcctggacat ggcaatgatg agtttttaaa aaacagtgtg | 1380 |
| gatgatgata tgcttttgtg agcaagcaaa agcagaaacg tgaagccgtg atacaaattg | 1440 |
| gtgaacaaaa aatgcccaag gcttctcatg tctttattct gaagagcttt aatatatact | 1500 |
| ctatgtagtt taataagcac tgtacgtaga aggcctagg tgttgcatgt ctatgcttga | 1560 |
| ggaacttttc caaatgtgtg tgtctgcatg tgtgtttgta catagaagtc atagatgcag | 1620 |
| aagtggttct gctggtacga tttgattcct gttggaatgt ttaaattaca ctaagtgtac | 1680 |
| tactttatat aatcaatgaa attgctagac atgttttagc aggacttttc taggaaagac | 1740 |
| ttatgtataa ttgcttttta aaatgcagtg ctttacttta aactaagggg aactttgcgg | 1800 |
| aggtgaaaac ctttgctggg ttttctgttc aataaagttt tactatgaat gaaaaaaaaa | 1860 |
| aaaaaaaaa a | 1871 |

<210> SEQ ID NO 8
<211> LENGTH: 1865
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 8

| | | | | | |
|---|---|---|---|---|---|
| agagacgtga | actgtcgttg | cagagattgc | gggcggctga | gacgccgcct | gcctggcacc | 60 |
| taggagcgca | gcggagcccc | gacaccgccg | ccgccgccat | ggagtccgag | accgaacccg | 120 |
| agcccgtcac | gctcctggtg | aagagcccca | accagcgcca | ccgcgacttg | gagctgagtg | 180 |
| gcgaccgcgg | ctggagtgtg | ggccacctca | aggcccacct | gagccgcgtc | taccccgagc | 240 |
| gtccgcgtcc | agaggaccag | aggttaattt | attctgggaa | gctgttgttg | gatcaccaat | 300 |
| gtctcaggga | cttgcttcca | aagcaggaaa | aacggcatgt | tttgcatctg | gtgtgcaatg | 360 |
| tgaagagtcc | ttcaaaaatg | ccagaaatca | acgccaaggt | ggctgaatcc | acagaggagc | 420 |
| ctgctggttc | taatcgggga | cagtatcctg | aggattcctc | aagtgatggt | ttaaggcaaa | 480 |
| gggaagttct | tcggaacctt | tcttcccctg | gatgggaaaa | catctcaagg | cctgaagctg | 540 |
| cccagcaggc | attccaaggc | ctgggtcctg | gtttctccgg | ttacacaccc | tatgggtggc | 600 |
| ttcagctttc | ctggttccag | cagatatatg | cacgacagta | ctacatgcaa | tatttagcag | 660 |
| ccactgctgc | atcaggggct | tttgttccac | caccaagtgc | acaagagata | cctgtggtct | 720 |
| ctgcacctgc | tccagcccct | attcacaacc | agtttccagc | tgaaaaccag | cctgccaatc | 780 |
| agaatgctgc | tcctcaagtg | gttgttaatc | ctggagccaa | tcaaaatttg | cggatgaatg | 840 |
| cacaaggtgg | ccctattgtg | gaagaagatg | atgaaataaa | tcgagattgg | ttggattgga | 900 |
| cctattcagc | agctacattt | tctgtttttc | tcagtatcct | ctacttctac | tcctccctga | 960 |
| gcagattcct | catggtcatg | ggggccaccg | ttgttatgta | cctgcatcac | gttgggtggt | 1020 |
| ttccatttag | accgaggccg | gttcagaact | tcccaaatga | tggtcctcct | cctgacgttg | 1080 |
| taaatcagga | ccccaacaat | aacttacagg | aaggcactga | tcctgaaact | gaagacccca | 1140 |
| accacctccc | tccagacagg | gatgtactag | atggcgagca | gaccagcccc | tcctttatga | 1200 |
| gcacagcatg | gcttgtcttc | aagactttct | ttgcctctct | tcttccagaa | ggccccccag | 1260 |
| ccatcgcaaa | ctgatggtgt | tgtgctgta | gctgttggag | gctttgacag | gaatggactg | 1320 |
| gatcacctga | ctccagctag | attgcctctc | ctggacatgg | caatgatgag | ttttaaaaa | 1380 |
| acagtgtgga | tgatgatatg | cttttgtgag | caagcaaaag | cagaaacgtg | aagccgtgat | 1440 |
| acaaattggt | gaacaaaaaa | tgcccaaggc | ttctcatgtc | tttattctga | agagctttaa | 1500 |
| tatatactct | atgtagttta | ataagcactg | tacgtagaag | gccttaggtg | ttgcatgtct | 1560 |
| atgcttgagg | aacttttcca | aatgtgtgtg | tctgcatgtg | tgtttgtaca | tagaagtcat | 1620 |
| agatgcagaa | gtggtctgc | tggtacgatt | tgattcctgt | tggaatgttt | aaattacact | 1680 |
| aagtgtacta | ctttatataa | tcaatgaaat | tgctagacat | gttttagcag | gacttttcta | 1740 |
| ggaaagactt | atgtataatt | gcttttttaaa | atgcagtgct | ttactttaaa | ctaaggggaa | 1800 |
| ctttgcggag | gtgaaaacct | ttgctgggtt | ttctgttcaa | taaagtttta | ctatgaatga | 1860 |
| ccctg | | | | | 1865 |

<210> SEQ ID NO 9
<211> LENGTH: 1884
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 9

```
gacgtgaacg tcgttgcag agattgcggg cggctgagac gccgcctgcc tggcacctag      60
gagcgcagcg gagccccgac accgccgccg ccgccatgga gtccgagacc gaacccgagc    120
ccgtcacgct cctggtgaag agccccaacc agcgccaccg cgacttggag ctgagtggcg    180
accgcggctg gagtgtgggc cacctcaagg cccacctgag ccgcgtctac cccgagcgtc    240
cgcgtccaga ggaccagagg ttaatttatt ctgggaagct gttgttggat caccaatgtc    300
tcagggactt gcttccaaag caggaaaaac ggcatgtttt gcatctggtg tgcaatgtga    360
agagtccttc aaaaatgcca gaaatcaacg ccaaggtggc tgaatccaca gaggagcctg    420
ctggttctaa tcggggacag tatcctgagg attcctcaag tgatggttta aggcaaaggg    480
aagttcttcg gaacctttct tccctggat gggaaaacat ctcaaggcct gaagctgccc    540
agcaggcatt ccaaggcctg gtcctggtt tctccggtta cacaccctat gggtggcttc    600
agctttcctg gttccagcag atatatgcac gacagtacta catgcaatat ttagcagcca    660
ctgctgcatc agggcttttt gttccaccac caagtgcaca agagatacct gtggtctctg    720
cacctgctcc agccctatt cacaaccagt ttccagctga aaaccagcct gccaatcaga    780
atgctgctcc tcaagtggtt gttaatcctg agccaatca aaatttgcgg atgaatgcac    840
aaggtggccc tattgtggaa gaagatgatg aaataaatcg agattggttg gattggacct    900
attcagcagc tacattttct gtttttctca gtatcctcta cttctactcc tccctgagca    960
gattcctcat ggtcatgggg gccaccgttg ttatgtacct gcatcacgtt gggtggtttc   1020
catttagacc gaggccggtt cagaacttcc caaatgatgg tcctcctcct gacgttgtaa   1080
atcaggaccc caacaataac ttacaggaag gcactgatcc tgaaactgaa gaccccaacc   1140
acctccctcc agacagggat gtactagatg gcgagcagac cagcccctcc tttatgagca   1200
cagcatggct tgtcttcaag actttctttg cctctcttct tccagaaggc cccccagcca   1260
tcgcaaactg atggtgtttg tgctgtagct gttggaggct ttgacaggaa tggactggat   1320
cacctgactc cagctagatt gcctctcctg gacatggcaa tgatgagttt ttaaaaaaca   1380
gtgtggatga tgatatgctt ttgtgagcaa gcaaaagcag aaacgtgaag ccgtgataca   1440
aattggtgaa caaaaaatgc ccaaggcttc tcatgtcttt attctgaaga gctttaatat   1500
atactctatg tagtttaata agcactgtac gtagaaggcc ttaggtgttg catgtctatg   1560
cttgaggaac ttttccaaat gtgtgtgtct gcatgtgtgt ttgtacatag aagtcataga   1620
tgcagaagtg gttctgctgg tacgatttga ttcctgttgg aatgttaa ttacactaag    1680 tgtactactt tatataatca atgaaattgc tagacatgtt ttagcaggac tttctagga    1740 aagacttatg tataattgct tttaaaatg cagtgctta ctttaaacta aggggaactt     1800
tgcggaggtg aaaacctttg ctgggtttc tgttcaataa agttttacta tgaatgaccc    1860
tgaaaaaaaa aaaaaaaaa aaaa                                             1884

<210> SEQ ID NO 10
<211> LENGTH: 1860
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10
cgtgaacggt cgttgcagag attgcgggcg gctgagacgc cgcctgcctg gcacctagga     60
gcgcagcgga gccccgacac cgccgccgcc gccatggagt ccgagaccga acccgagccc    120
```

```
gtcacgctcc tggtgaagag ccccaaccag cgccaccgcg acttggagct gagtggcgac      180
cgcggctgga gtgtgggcca cctcaaggcc cacctgagcc gcgtctaccc cgagcgtccg      240
cgtccagagg accagaggtt aatttattct gggaagctgt tgttggatca ccaatgtctc      300
agggacttgc ttccaaagca ggaaaaacgg catgttttgc atctggtgtg caatgtgaag      360
agtccttcaa aaatgccaga atcaacgcc aaggtggctg aatccacaga ggagcctgct       420
ggttctaatc ggggacagta tcctgaggat tcctcaagtg atggtttaag gcaaagggaa      480
gttcttcgga accttttcttc ccctggatgg gaaaacatct caaggcctga agctgcccag     540
caggcattcc aaggcctggg tcctggtttc tccggttaca cacccttatgg gtggcttcag    600 ctttcctggt tccagcagat atatgcacga cagtactaca tgcaatattt agcagccact     660
gctgcatcag gggcttttgt tccaccacca agtgcacaag agatacctgt ggtctctgca    720
cctgctccag cccctattca caaccagttt ccagctgaaa accagcctgc caatcagaat    780
gctgctcctc aagtggttgt taatcctgga gccaatcaaa atttgcggat gaatgcacaa    840
ggtggcccta ttgtggaaga agatgatgaa ataaatcgag attggttgga ttggacctat    900
tcagcagcta cattttctgt ttttctcagt atcctctact tctactcctc cctgagcaga    960
ttcctcatgg tcatggggc caccgttgtt atgtacctgc atcacgttgg gtggtttcca    1020
tttagaccga ggccggttca gaacttccca aatgatggtc ctcctcctga cgttgtaaat    1080
caggacccca acaataactt acaggaaggc actgatcctg aaactgaaga ccccaaccac    1140
ctccctccag acagggatgt actagatggc gagcagacca gccccctccct tatgagcaca   1200 gcatggcttg tcttcaagac tttctttgcc tctcttcttc cagaaggccc cccagccatc    1260
gcaaactgat ggtgttttgtg ctgtagctgt tggaggcttt gacaggaatg gactggatca   1320
cctgactcca gctagattgc ctctcctgga catggcaatg atgagttttt aaaaaacagt    1380
gtggatgatg atatgctttt gtgagcaagc aaaagcagaa acgtgaagcc gtgatacaaa    1440
ttggtgaaca aaaaatgccc aaggcttctc atgtgtttat tctgaagagc tttaatatat    1500
actctatgta gtttaataag cactgtacgt agaaggcctt aggtgttgca tgtctatgct    1560
tgaggaactt ttccaaatgt gtgtgtctgc atgtgtgttt gtacatagaa gtcatagatg    1620
cagaagtggt tctgctggta agatttgatt cctgttggaa tgtttaaatt acactaagtg    1680
tactacttta tataatcaat gaaattgcta gacatgtttt agcaggactt ttctaggaaa    1740
gacttatgta taattgcttt ttaaaatgca gtgctttact ttaaactaag gggaactttg    1800
cggaggtgaa aacctttgct gggttttctg ttcaataaag ttttactatg aatgaccctg    1860
```

<210> SEQ ID NO 11
<211> LENGTH: 1884
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11

```
gacgtgaacg gtcgttgcag agattgcggg cggctgagac gccgcctgcc tggcacctag       60
gagcgcagcg gagccccgac accgccgccg ccgccatgga gtccgagacc gaacccgagc     120
ccgtcacgct cctggtgaag agccccaacc agcgccaccg cgacttggag ctgagtggcg     180
accgcggctg gagtgtgggc cacctcaagg cccacctgag ccgcgtctac cccgagcgtc     240
cgcgtccaga ggaccagagg ttaatttatt ctggaagct gttgttggat caccaatgtc     300
tcagggactt gcttccaaag caggaaaaac ggcatgtttt gcatctggtg tgcaatgtga    360
```

```
agagtccttc aaaaatgcca gaaatcaacg ccaaggtggc tgaatccaca gaggagcctg    420
ctggttctaa tcggggacag tatcctgagg attcctcaag tgatggttta aggcaaaggg    480
aagttcttcg gaacctttct tcccctggat gggaaaacat ctcaaggcct gaagctgccc    540
agcaggcatt ccaaggcctg gtcctggttt ctccggttta cacccctat gggtggcttc     600 agctttcctg gttccagcag atatatgcac gacagtacta catgcaatat ttagcagcca    660
ctgctgcatc agggcttttt gttccaccac caagtgcaca agagatacct gtggtctctg    720
cacctgctcc agcccctatt cacaaccagt ttccagctga aaaccagcct gccaatcaga    780
atgctgctcc tcaagtggtt gttaatcctg agccaatca aaatttgcgg atgaatgcac     840
aaggtggccc tattgtggaa gaagatgatg aaataaatcg agattggttg gattggacct    900
attcagcagc tacattttct gttttctca gtatcctcta cttctactcc tcctgagca     960 gattcctcat ggtcatgggg gccaccgttg ttatgtacct gcatcacgtt gggtggtttc   1020
catttagacc gaggccggtt cagaacttcc caaatgatgg tcctcctcct gacgttgtaa   1080
atcaggaccc caacaataac ttacaggaag gcactgatcc tgaaactgaa gaccccaacc   1140
acctccctcc agacagggat gtactagatg gcgagcagca cagcccctcc tttatgagca   1200
cagcatggct tgtcttcaag actttctttg cctctcttct tccagaaggc cccccagcca   1260
tcgcaaactg atggtgtttg tgctgtagct gttggaggct tgacaggaa tggactggat    1320 cacctgactc cagctagatt gcctctcctg gacatggcaa tgatgagttt ttaaaaaaca   1380
gtgtggatga tgatatgctt ttgtgagcaa gcaaaagcag aaacgtgaag ccgtgataca   1440
aattggtgaa caaaaaatgc ccaaggcttc tcatgtcttt attctgaaga gctttaatat   1500
atactctatg tagtttaata agcactgtac gtagaaggcc ttaggtgttg catgtctatg   1560
cttgaggaac ttttccaaat gtgtgtgtct gcatgtgtgt ttgtacatag aagtcataga   1620
tgcagaagtg gttctgctgg tacgatttga ttcctgttgg aatgtttaaa ttacactaag   1680
tgtactactt tatataatca atgaaattgc tagacatgtt ttagcaggac ttttctagga   1740
aagacttatg tataattgct ttttaaaatg cagtgcttta cttaaaacta aggggaactt   1800
tgcggaggtg aaaacctttg ctgggttttc tgttcaataa agttttacta tgaatgaccc   1860
tgaaaaaaaa aaaaaaaaaa aaaa                                          1884
```

<210> SEQ ID NO 12
<211> LENGTH: 232
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

```
Met Glu Ser Glu Thr Glu Pro Glu Pro Val Thr Leu Leu Val Lys Ser
1               5                   10                  15

Pro Asn Gln Arg His Arg Asp Leu Glu Leu Ser Gly Asp Arg Gly Trp
            20                  25                  30

Ser Val Gly His Leu Lys Ala His Leu Ser Arg Val Tyr Pro Glu Arg
        35                  40                  45

Pro Arg Pro Glu Asp Gln Arg Leu Ile Tyr Ser Gly Lys Leu Leu Leu
    50                  55                  60

Asp His Gln Cys Leu Arg Asp Leu Leu Pro Lys Glu Lys Arg His Val
65                  70                  75                  80

Leu His Leu Val Cys Asn Val Lys Ser Pro Ser Lys Met Pro Glu Ile
```

```
                    85                  90                  95
Asn Ala Lys Val Ala Glu Ser Thr Glu Pro Ala Gly Ser Asn Arg
            100                 105                 110

Gly Gln Tyr Pro Glu Asp Ser Ser Asp Gly Leu Arg Gln Arg Glu
            115                 120                 125

Val Leu Arg Asn Leu Ser Ser Pro Gly Trp Glu Asn Ile Ser Arg His
        130                 135                 140

His Val Gly Trp Phe Pro Phe Arg Pro Arg Pro Val Gln Asn Phe Pro
145                 150                 155                 160

Asn Asp Gly Pro Pro Asp Val Val Asn Gln Asp Pro Asn Asn Asn
                165                 170                 175

Leu Gln Glu Gly Thr Asp Pro Glu Thr Glu Asp Pro Asn His Leu Pro
            180                 185                 190

Pro Asp Arg Asp Val Leu Asp Gly Glu Gln Thr Ser Pro Ser Phe Met
            195                 200                 205

Ser Thr Ala Trp Leu Val Phe Lys Thr Phe Phe Ala Ser Leu Leu Pro
        210                 215                 220

Glu Gly Pro Pro Ala Ile Ala Asn
225                 230

<210> SEQ ID NO 13
<211> LENGTH: 209
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Met Gln Tyr Leu Ala Ala Thr Ala Ala Ser Gly Ala Phe Val Pro Pro
1               5                   10                  15

Pro Ser Ala Gln Glu Ile Pro Val Val Ser Ala Pro Ala Pro
            20                  25                  30

Ile His Asn Gln Phe Pro Ala Glu Asn Gln Pro Ala Asn Gln Asn Ala
        35                  40                  45

Ala Pro Gln Val Val Asn Pro Gly Ala Asn Gln Asn Leu Arg Met
50                  55                  60

Asn Ala Gln Gly Gly Pro Ile Val Glu Glu Asp Glu Ile Asn Arg
65                  70                  75                  80

Asp Trp Leu Asp Trp Thr Tyr Ser Ala Ala Thr Phe Ser Val Phe Leu
                85                  90                  95

Ser Ile Leu Tyr Phe Tyr Ser Ser Leu Ser Arg Phe Leu Met Val Met
            100                 105                 110

Gly Ala Thr Val Val Met Tyr Leu His His Val Gly Trp Phe Pro Phe
        115                 120                 125

Arg Pro Arg Pro Val Gln Asn Phe Pro Asn Asp Gly Pro Pro Asp
130                 135                 140

Val Val Asn Gln Asp Pro Asn Asn Leu Gln Glu Gly Thr Asp Pro
145                 150                 155                 160

Glu Thr Glu Asp Pro Asn His Leu Pro Pro Asp Arg Asp Val Leu Asp
            165                 170                 175

Gly Glu Gln Thr Ser Pro Ser Phe Met Ser Thr Ala Trp Leu Val Phe
            180                 185                 190

Lys Thr Phe Phe Ala Ser Leu Leu Pro Glu Gly Pro Pro Ala Ile Ala
        195                 200                 205

Asn
```

```
<210> SEQ ID NO 14
<211> LENGTH: 356
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Gly His Leu Lys Ala His Leu Ser Arg Val Tyr Pro Glu Arg Pro Arg
1               5                   10                  15

Pro Glu Asp Gln Arg Leu Ile Tyr Ser Gly Lys Leu Leu Leu Asp His
                20                  25                  30

Gln Cys Leu Arg Asp Leu Leu Pro Lys Glu Lys Arg His Val Leu His
        35                  40                  45

Leu Val Cys Asn Val Lys Ser Pro Ser Lys Met Pro Glu Ile Asn Ala
    50                  55                  60

Lys Val Ala Glu Ser Thr Glu Glu Pro Ala Gly Ser Asn Arg Gly Gln
65                  70                  75                  80

Tyr Pro Glu Asp Ser Ser Asp Gly Leu Arg Gln Arg Glu Val Leu
                85                  90                  95

Arg Asn Leu Ser Ser Pro Gly Trp Glu Asn Ile Ser Arg Pro Glu Ala
                100                 105                 110

Ala Gln Gln Ala Phe Gln Gly Leu Gly Pro Gly Phe Ser Gly Tyr Thr
            115                 120                 125

Pro Tyr Gly Trp Leu Gln Leu Ser Trp Phe Gln Gln Ile Tyr Ala Arg
        130                 135                 140

Gln Tyr Tyr Met Gln Tyr Leu Ala Ala Thr Ala Ala Ser Gly Ala Phe
145                 150                 155                 160

Val Pro Pro Pro Ser Ala Gln Glu Ile Pro Val Val Ser Ala Pro Ala
                165                 170                 175

Pro Ala Pro Ile His Asn Gln Phe Pro Ala Glu Asn Gln Pro Ala Asn
                180                 185                 190

Gln Asn Ala Ala Pro Gln Val Val Val Asn Pro Gly Ala Asn Gln Asn
            195                 200                 205

Leu Arg Met Asn Ala Gln Gly Gly Pro Ile Val Glu Glu Asp Asp Glu
    210                 215                 220

Ile Asn Arg Asp Trp Leu Asp Trp Thr Tyr Ser Ala Ala Thr Phe Ser
225                 230                 235                 240

Val Phe Leu Ser Ile Leu Tyr Phe Tyr Ser Ser Leu Ser Arg Phe Leu
                245                 250                 255

Met Val Met Gly Ala Thr Val Val Met Tyr Leu His His Val Gly Trp
                260                 265                 270

Phe Pro Phe Arg Pro Arg Pro Val Gln Asn Phe Pro Asn Asp Gly Pro
            275                 280                 285

Pro Pro Asp Val Val Asn Gln Asp Pro Asn Asn Asn Leu Gln Glu Gly
        290                 295                 300

Thr Asp Pro Glu Thr Glu Asp Pro Asn His Leu Pro Pro Asp Arg Asp
305                 310                 315                 320

Val Leu Asp Gly Glu Gln Thr Ser Pro Ser Phe Met Ser Thr Ala Trp
                325                 330                 335

Leu Val Phe Lys Thr Phe Phe Ala Ser Leu Leu Pro Glu Gly Pro Pro
                340                 345                 350

Ala Ile Ala Asn
            355
```

<210> SEQ ID NO 15
<211> LENGTH: 391
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 15

```
Met Glu Ser Glu Thr Glu Pro Glu Pro Val Thr Leu Leu Val Lys Ser
1               5                   10                  15

Pro Asn Gln Arg His Arg Asp Leu Glu Leu Ser Gly Asp Arg Gly Trp
            20                  25                  30

Ser Val Gly His Leu Lys Ala His Leu Ser Arg Val Tyr Pro Glu Arg
        35                  40                  45

Pro Arg Pro Glu Asp Gln Arg Leu Ile Tyr Ser Gly Lys Leu Leu Leu
    50                  55                  60

Asp His Gln Cys Leu Arg Asp Leu Leu Pro Lys Gln Glu Lys Arg His
65                  70                  75                  80

Val Leu His Leu Val Cys Asn Val Lys Ser Pro Ser Lys Met Pro Glu
                85                  90                  95

Ile Asn Ala Lys Val Ala Glu Ser Thr Glu Glu Pro Ala Gly Ser Asn
            100                 105                 110

Arg Gly Gln Tyr Pro Glu Asp Ser Ser Asp Gly Leu Arg Gln Arg
        115                 120                 125

Glu Val Leu Arg Asn Leu Ser Ser Pro Gly Trp Glu Asn Ile Ser Arg
    130                 135                 140

Pro Glu Ala Ala Gln Gln Ala Phe Gln Gly Leu Gly Pro Gly Phe Ser
145                 150                 155                 160

Gly Tyr Thr Pro Tyr Gly Trp Leu Gln Leu Ser Trp Phe Gln Gln Ile
                165                 170                 175

Tyr Ala Arg Gln Tyr Tyr Met Gln Tyr Leu Ala Ala Thr Ala Ala Ser
            180                 185                 190

Gly Ala Phe Val Pro Pro Ser Ala Gln Glu Ile Pro Val Val Ser
        195                 200                 205

Ala Pro Ala Pro Ala Pro Ile His Asn Gln Phe Pro Ala Glu Asn Gln
    210                 215                 220

Pro Ala Asn Gln Asn Ala Ala Pro Gln Val Val Asn Pro Gly Ala
225                 230                 235                 240

Asn Gln Asn Leu Arg Met Asn Ala Gln Gly Gly Pro Ile Val Glu Glu
                245                 250                 255

Asp Asp Glu Ile Asn Arg Asp Trp Leu Asp Trp Thr Tyr Ser Ala Ala
            260                 265                 270

Thr Phe Ser Val Phe Leu Ser Ile Leu Tyr Phe Tyr Ser Ser Leu Ser
        275                 280                 285

Arg Phe Leu Met Val Met Gly Ala Thr Val Val Met Tyr Leu His His
    290                 295                 300

Val Gly Trp Phe Pro Phe Arg Pro Arg Pro Val Gln Asn Phe Pro Asn
305                 310                 315                 320

Asp Gly Pro Pro Asp Val Val Asn Gln Asp Pro Asn Asn Leu
                325                 330                 335

Gln Glu Gly Thr Asp Pro Glu Thr Glu Asp Pro Asn His Leu Pro Pro
            340                 345                 350

Asp Arg Asp Val Leu Asp Gly Glu Gln Thr Ser Pro Ser Phe Met Ser
        355                 360                 365
```

Thr Ala Trp Leu Val Phe Lys Thr Phe Phe Ala Ser Leu Leu Pro Glu
    370                 375                 380

Gly Pro Pro Ala Ile Ala Asn
385                 390

<210> SEQ ID NO 16
<211> LENGTH: 1857
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16

| | | | | | |
|---|---|---|---|---|---|
| aagacaccaa | gtgtcgttgt | ggggtcgcag | acggctgcgt | cgccgcccgt | tcggcatccc | 60 |
| tgagcgcagt | cgagcctcca | gcgccgcaga | catggagccc | gagccacagc | ccgagccggt | 120 |
| cacgctgctg | gtgaagagcc | ccaatcagcg | ccaccgcgac | ttggagctga | gtggcgaccg | 180 |
| cggttggagt | gtgagtcgcc | tcaaggccca | cctgagccga | gtctaccccg | aacgcccgcg | 240 |
| cccagaggac | cagaggttaa | tttattctgg | gaagctgctg | tttggatcac | caatgtctcc a | 300 |
| agacttgctt | ccaaagcagg | aaaagcgaca | tgttttgcac | ctcgtgtgca | atgtgaggag | 360 |
| tccctcaaaa | aagccagaag | ccagcacaaa | gggtgctgag | tccacagagc | agccggacaa | 420 |
| cactagtcag | gcacagtatc | ctggggattc | ctcaagcgat | ggcttacggg | aaagggaagt | 480 |
| ccttcggaac | cttcctccct | ctggatggga | gaacgtctct | aggcctgaag | ccgtccagca | 540 |
| gactttccaa | ggcctcgggc | ccggcttctc | tggctacacc | acctacgggt | ggctgcagct | 600 |
| ctcctggttc | cagcagatct | atgcaagaca | gtactacatg | caatacttgg | ctgccactgc | 660 |
| tgcttcagga | gcttttggcc | ctacaccaag | tgcacaagaa | atacctgtgg | tctctacacc | 720 |
| ggctcccgcc | cctatacaca | accagttccc | ggcagaaaac | cagccggcca | atcagaatgc | 780 |
| agccgctcaa | gcggttgtta | atcccggagc | caatcagaac | ttgcggatga | atgcacaagg | 840 |
| cggccctctg | gtggaagaag | atgatgagat | aaaccgagac | tggttggatt | ggacctactc | 900 |
| agcagcgaca | ttttccgttt | tcctcagcat | tctttacttc | tactcctccc | tgagcagatt | 960 |
| cctcatggtc | atgggcgcca | ccgtagtcat | gtacctgcac | acgtcgggt | ggtttccatt | 1020 |
| cagacagagg | ccagttcaga | acttcccaga | tgacggtccc | cctcaggaag | ctgccaacca | 1080 |
| ggacccccaac | aataacctcc | agggaggttt | ggaccctgaa | atggaagacc | ccaaccgcct | 1140 |
| ccccgtaggc | cgtgaagtgc | tggacccctga | gcataccagc | ccctcgttca | tgagcacagc | 1200 |
| atggctagtc | ttcaagactt | tctttgcctc | tcttcttccg | gaaggcccac | cagccctagc | 1260 |
| aaactgatgg | cccctgtgct | ctgttgctgg | aggctttcac | agcttggact | ggatcgtccc | 1320 |
| ctggcgtgga | ctcgagagag | tcattgaaaa | cccacaggat | gacgatgtgc | ttctgtgcca | 1380 |
| agcaaaagca | caaactaaga | catgaagccg | tggtacaaac | tgaacagggc | ccctcatgtc | 1440 |
| gttattctga | agagctttaa | tgtatactgt | atgtagtctc | ataggcactg | taaacagaag | 1500 |
| gcccagggtc | gcatgttctg | cctgagcacc | tccccagacg | tgtgtgcatg | tgtgccgtac | 1560 |
| atggaagtca | tagacgtgtg | tgcatgtgtg | ctctacatgg | aagtcataga | tgcagaaacg | 1620 |
| gttctgctgg | ttcgatttga | ttcctgttgg | aatgttgcaa | ttcactaag | tgtactactt | 1680 |
| tatataatca | gtgacttgct | agacatgtta | gcaggacttt | tctaggagag | acttattgta | 1740 |
| tcattgcttt | ttaaaacgca | gtgcttactt | actgagggcg | gcgacttggc | acaggtaaag | 1800 |
| cctttgccgg | gttttctgtt | caataaagtt | ttgctatgaa | cgacaaaaaa | aaaaaaa | 1857 |

<210> SEQ ID NO 17
<211> LENGTH: 391
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 17

Met Glu Pro Glu Pro Gln Pro Glu Pro Val Thr Leu Leu Val Lys Ser
1               5                   10                  15

Pro Asn Gln Arg His Arg Asp Leu Glu Leu Ser Gly Asp Arg Gly Trp
            20                  25                  30

Ser Val Ser Arg Leu Lys Ala His Leu Ser Arg Val Tyr Pro Glu Arg
        35                  40                  45

Pro Arg Pro Glu Asp Gln Arg Leu Ile Tyr Ser Gly Lys Leu Leu Leu
    50                  55                  60

Asp His Gln Cys Leu Gln Asp Leu Leu Pro Lys Gln Glu Lys Arg His
65                  70                  75                  80

Val Leu His Leu Val Cys Asn Val Arg Ser Pro Ser Lys Lys Pro Glu
                85                  90                  95

Ala Ser Thr Lys Gly Ala Glu Ser Thr Glu Gln Pro Asp Asn Thr Ser
            100                 105                 110

Gln Ala Gln Tyr Pro Gly Asp Ser Ser Asp Gly Leu Arg Glu Arg
        115                 120                 125

Glu Val Leu Arg Asn Leu Pro Pro Ser Gly Trp Glu Asn Val Ser Arg
    130                 135                 140

Pro Glu Ala Val Gln Gln Thr Phe Gln Gly Leu Gly Pro Gly Phe Ser
145                 150                 155                 160

Gly Tyr Thr Thr Tyr Gly Trp Leu Gln Leu Ser Trp Phe Gln Gln Ile
                165                 170                 175

Tyr Ala Arg Gln Tyr Tyr Met Gln Tyr Leu Ala Ala Thr Ala Ala Ser
            180                 185                 190

Gly Ala Phe Gly Pro Thr Pro Ser Ala Gln Glu Ile Pro Val Val Ser
        195                 200                 205

Thr Pro Ala Pro Ala Pro Ile His Asn Gln Phe Pro Ala Glu Asn Gln
    210                 215                 220

Pro Ala Asn Gln Asn Ala Ala Gln Ala Val Asn Pro Gly Ala
225                 230                 235                 240

Asn Gln Asn Leu Arg Met Asn Ala Gln Gly Gly Pro Leu Val Glu Glu
                245                 250                 255

Asp Asp Glu Ile Asn Arg Asp Trp Leu Asp Trp Thr Tyr Ser Ala Ala
            260                 265                 270

Thr Phe Ser Val Phe Leu Ser Ile Leu Tyr Phe Tyr Ser Ser Leu Ser
        275                 280                 285

Arg Phe Leu Met Val Met Gly Ala Thr Val Val Met Tyr Leu His His
    290                 295                 300

Val Gly Trp Phe Pro Phe Arg Gln Arg Pro Val Gln Asn Phe Pro Asp
305                 310                 315                 320

Asp Gly Pro Pro Gln Glu Ala Ala Asn Gln Asp Pro Asn Asn Asn Leu
                325                 330                 335

Gln Gly Gly Leu Asp Pro Glu Met Glu Asp Pro Asn Arg Leu Pro Val
            340                 345                 350

Gly Arg Glu Val Leu Asp Pro Glu His Thr Ser Pro Ser Phe Met Ser
        355                 360                 365

Thr Ala Trp Leu Val Phe Lys Thr Phe Phe Ala Ser Leu Leu Pro Glu
    370                 375                 380

Gly Pro Pro Ala Leu Ala Asn
385                 390

<210> SEQ ID NO 18
<211> LENGTH: 1871
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18

| | | |
|---|---|---|
| aaagacgcca agtgtcgttg tgtggtctca dacggctgcg tcgccgcccg ttcggcatcc | 60 |
| ctgagcgcag tcgagccgcc agcgacgcag acatggagcc cgagccacag cccgagccgg | 120 |
| tcacgctgct ggtgaagagt cccaatcagc gccaccgcga cttggagctg agtggcgacc | 180 |
| gcagttggag tgtgagtcgc ctcaaggccc acctgagccg agtctacccc gagcgcccgc | 240 |
| gtccagagga ccagaggtta atttattctg ggaagctgct gttggatcac cagtgtctcc | 300 |
| aagatttgct tccaaagcag gaaaagcgac atgttttgca ccttgtgtgc aatgtgaaga | 360 |
| atccctccaa aatgccagaa accagcacaa agggtgctga atccacagag cagccggaca | 420 |
| actctaatca gacacagcat cctggggact cctcaagtga tggtttacgg caaagagaag | 480 |
| ttcttcggaa cctttctccc tccggatggg agaacatctc taggcctgag gctgtccagc | 540 |
| agactttcca aggcctgggg cctggcttct ctggctacac aacgtatggg tggctgcagc | 600 |
| tctcctggtt ccagcagatc tatgcaaggc agtactacat gcaatactta gctgccactg | 660 |
| ctgcatcagg aactttttgtc ccgacaccaa gtgcacaaga gatacctgtg gtctctacac | 720 |
| ctgctccggc tcctatacac aaccagtttc cggcagaaaa ccagccggcc aatcagaatg | 780 |
| cagctgctca agcggttgtc aatcccggag ccaatcagaa cttgcggatg aatgcacaag | 840 |
| gtggcccccct ggtggaggaa gatgatgaga taaaccgaga ctggttggat tggacctatt | 900 |
| ccgcagcgac gttttctgtt ttcctcagca tcctttactt ctactcctcg ctgagcagat | 960 |
| ttctcatggt catgggtgcc actgtagtca tgtacctgca ccacgtcggg tggtttccgt | 1020 |
| tcagacagag gccagttcag aacttcccgg atgatggtgg tcctcgagat gctgccaacc | 1080 |
| aggaccccaa caataacctc cagggaggta tggacccaga aatggaagac cccaaccgcc | 1140 |
| tcccccccaga ccgcgaagtg ctggaccctg agcacaccag cccctcgttt atgagcacag | 1200 |
| catggctagt cttcaagact ttctttgcct ctcttcttcc agaaggccca ccagccctag | 1260 |
| ccaactgatg gcccttgtgc tctgtcgctg gtggctttga cagctcggac tggatcgtct | 1320 |
| ggctccggct ccttttcctc ccctggcgtg gactcgacag agtcattgaa aacccacagg | 1380 |
| atgacatgtg cttctgtgcc aagcaaaagc acaaactaag acatgaagcc gtggtacaaa | 1440 |
| ctgaacaggg cccctcatgt cgttattctg aagagcttta atgtatactg tatgtagttt | 1500 |
| cataggcact gtaagcagaa ggcccagggt cgcatgttct gcctgagcac ctccccagat | 1560 |
| gtgtgtgcat gtgtgctgta catggaagtc atagacgtgt gtgcatgtgt gctctacatg | 1620 |
| gaagtcatag atgcagaaac ggttctgctg gttcgatttg attcctgttg gaatgttcaa | 1680 |
| attacactaa gtgtactact ttatataatc agtgaattgc tagacatgtt agcaggactt | 1740 |
| ttctaggaga gacttatgta taattgcttt ttaaaatgca gtgctttcct ttaaaccgag | 1800 |
| ggtggcgact tggcagaggt aaaacctttg ccgagttttc tgttcaataa agttttgcta | 1860 |
| tgaatgactg t | 1871 |

<210> SEQ ID NO 19
<211> LENGTH: 391
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 19

Met Glu Pro Glu Pro Gln Pro Glu Pro Val Thr Leu Leu Val Lys Ser
1               5                   10                  15

Pro Asn Gln Arg His Arg Asp Leu Glu Leu Ser Gly Asp Arg Ser Trp
            20                  25                  30

Ser Val Ser Arg Leu Lys Ala His Leu Ser Arg Val Tyr Pro Glu Arg
        35                  40                  45

Pro Arg Pro Glu Asp Gln Arg Leu Ile Tyr Ser Gly Lys Leu Leu Leu
    50                  55                  60

Asp His Gln Cys Leu Gln Asp Leu Leu Pro Lys Gln Glu Lys Arg His
65                  70                  75                  80

Val Leu His Leu Val Cys Asn Val Lys Asn Pro Ser Lys Met Pro Glu
                85                  90                  95

Thr Ser Thr Lys Gly Ala Glu Ser Thr Glu Gln Pro Asp Asn Ser Asn
            100                 105                 110

Gln Thr Gln His Pro Gly Asp Ser Ser Asp Gly Leu Arg Gln Arg
        115                 120                 125

Glu Val Leu Arg Asn Leu Ser Pro Ser Gly Trp Glu Asn Ile Ser Arg
    130                 135                 140

Pro Glu Ala Val Gln Gln Thr Phe Gln Gly Leu Gly Pro Gly Phe Ser
145                 150                 155                 160

Gly Tyr Thr Thr Tyr Gly Trp Leu Gln Leu Ser Trp Phe Gln Gln Ile
                165                 170                 175

Tyr Ala Arg Gln Tyr Tyr Met Gln Tyr Leu Ala Ala Thr Ala Ala Ser
            180                 185                 190

Gly Thr Phe Val Pro Thr Pro Ser Ala Gln Glu Ile Pro Val Val Ser
        195                 200                 205

Thr Pro Ala Pro Ala Pro Ile His Asn Gln Phe Pro Ala Glu Asn Gln
    210                 215                 220

Pro Ala Asn Gln Asn Ala Ala Gln Ala Val Val Asn Pro Gly Ala
225                 230                 235                 240

Asn Gln Asn Leu Arg Met Asn Ala Gln Gly Gly Pro Leu Val Glu Glu
                245                 250                 255

Asp Asp Glu Ile Asn Arg Asp Trp Leu Asp Trp Thr Tyr Ser Ala Ala
            260                 265                 270

Thr Phe Ser Val Phe Leu Ser Ile Leu Tyr Phe Tyr Ser Ser Leu Ser
        275                 280                 285

Arg Phe Leu Met Val Met Gly Ala Thr Val Val Met Tyr Leu His His
    290                 295                 300

Val Gly Trp Phe Pro Phe Arg Gln Arg Pro Val Gln Asn Phe Pro Asp
305                 310                 315                 320

Asp Gly Pro Arg Asp Ala Ala Asn Gln Asp Pro Asn Asn Asn Leu
                325                 330                 335

Gln Gly Gly Met Asp Pro Glu Met Glu Asp Pro Asn Arg Leu Pro Pro
            340                 345                 350

Asp Arg Glu Val Leu Asp Pro Glu His Thr Ser Pro Ser Phe Met Ser
        355                 360                 365